(12) United States Patent
Ono et al.

(10) Patent No.: US 7,964,293 B2
(45) Date of Patent: Jun. 21, 2011

(54) ELECTRON TRANSPORT MATERIAL AND ORGANIC ELECTROLUMINESCENT DEVICE USING THE SAME

(75) Inventors: Youhei Ono, Chiba (JP); Hiroshi Yamada, Chiba (JP); Akiko Kageyama, Chiba (JP); Manabu Uchida, Chiba (JP)

(73) Assignee: JNC Corporation, Tokyo (JP)

( * ) Notice: Subject to any disclaimer, the term of this patent is extended or adjusted under 35 U.S.C. 154(b) by 230 days.

(21) Appl. No.: 11/991,454

(22) PCT Filed: Sep. 5, 2006

(86) PCT No.: PCT/JP2006/317545
§ 371 (c)(1),
(2), (4) Date: Jun. 5, 2008

(87) PCT Pub. No.: WO2007/029696
PCT Pub. Date: Mar. 15, 2007

(65) Prior Publication Data
US 2009/0134780 A1    May 28, 2009

(30) Foreign Application Priority Data
Sep. 5, 2005 (JP) .................. 2005-255794

(51) Int. Cl.
*H01J 1/63* (2006.01)
(52) U.S. Cl. .................. 428/690; 313/504; 546/257
(58) Field of Classification Search .................. None
See application file for complete search history.

(56) References Cited

U.S. PATENT DOCUMENTS

| | | | |
|---|---|---|---|
| 6,352,791 | B1 | 3/2002 | Fink et al. |
| 2002/0034658 | A1 | 3/2002 | Yamada et al. |
| 2006/0186797 | A1 | 8/2006 | Nishiyama et al. |

FOREIGN PATENT DOCUMENTS

| | | |
|---|---|---|
| EP | 1 690 847 | 8/2006 |
| EP | 1690847 | * 8/2006 |
| JP | 7-325329 | 12/1995 |
| JP | 2003-123983 | 4/2003 |

OTHER PUBLICATIONS

Fu et.al., Electro. Propeties of . . . quinquepyridine, 2001,Chemical Physics Letters 343, pp. 201-204.*
Tabatake, Low Operational . . . Conducting Silole derivative, 2002, Jpn. J. Appl. Phys. vol. 41, pp. 6582-6585.*
Sauer et. al., . . . Branched Oligopyridines, 1998, Tetrahedron Letters vol. 38, No. 39 pp. 6691-6694.*
Sauer et. al., . . . Branched Oligopyridines, 1998, Tetrahedron Letters vol. 38, No. 48 pp. 8817-8820.*
International Search Report issued Nov. 7, 2006 in the International (PCT) Application PCT/JP2006/317545 of which the present application is the U.S. National Stage.
Manabu Uchida et al., "Relationships between the Structures of Pyridylsilole Derivatives and the Performance for Organic Electroluminescent Device", Yokohama Research Center, Chisso Corporation, Proceedings of the 10th International Workshop on Inorganic and Organic Electroluminescence, pp. 241-244, Dec. 2000.
Gunther R. Pabst et al., "The New and Simple 'Lego' System: Its Application to the Synthesis of Superbranched Oligopyridines", Tetrahedron Letters, 39, pp. 8817-8820, 1998.
Gunther R. Pabst et al., "The New and Simple 'LEGO' System for the Synthesis of Branched Oligopyridines", Tetrahedron Letters, 39, pp. 6691-6694, 1998.
Rafat Mohamed Shaker et al., "Synthesis of 4,4'-(1,4-Phenylene)dipyridine and -pyrimidine Derivatives", J. Chem. Research (S), pp. 294-295, 1997.

* cited by examiner

*Primary Examiner* — D. Lawrence Tarazano
*Assistant Examiner* — Gregory Clark
(74) *Attorney, Agent, or Firm* — Wenderoth, Lind & Ponack, L.L.P.

(57) ABSTRACT

A compound represented by the following Formula (1) is useful as an electron transport material of an organic EL device, and an organic EL device comprising the compound in the electron transport layer is long in life, and low in drive voltage:

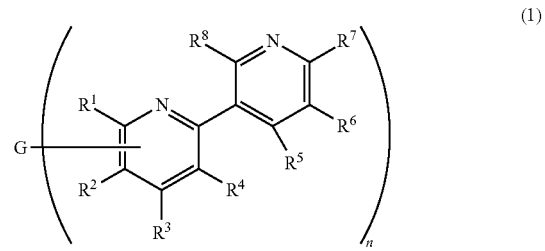

(1)

wherein G is an n-valent link, n is an integer of 2 to 4; $R^1$ to $R^4$ are each independently hydrogen, a monovalent group, or a free valency bonded with G, and $R^5$ to $R^8$ are each independently hydrogen or a monovalent group, and one of $R^1$ to $R^4$ is a free valency bonded with G; and n groups of 2,3'-bipyridyl may be the same or different with each other.

15 Claims, No Drawings

ELECTRON TRANSPORT MATERIAL AND ORGANIC ELECTROLUMINESCENT DEVICE USING THE SAME

BACKGROUND OF THE INVENTION

1. Field of the Invention

The invention relates to a novel electron transport material having a 2,3'-bipyridyl group, and an organic electroluminescent device (hereinafter abbreviated as an organic EL device, or merely as a device occasionally) using the above electron transport material.

2. Related Art

In recent years, attentions are paid to an organic EL device as a full color flat panel display in the subsequent generation, and the organic EL device has been actively researched. In order to accelerate practical use of the organic EL device, reduction of voltage for driving a device and long life are an essential element, and a new electron transport material has been developed to achieve the above performances. In JP 2003-123983 A/2003 (Patent document 1), an art is described that an organic EL device can be driven at low voltage by using a phenanthroline derivative for an electron transport material, and that an organic EL device can be driven at low voltage also by using a 2,2'-bipyridyl compound as an analog of the phenanthroline for an electron transport material in a similar manner. However, characteristics (e.g. drive voltage, emission efficiency) of the device which are reported in Examples of the above document are only a relative value based on Comparative example, and an actual measurement which can be judged to be a practically applicable value is not described. Additionally, an example where a 2,2'-bipyridyl compound is used for an electron transport material is disclosed in Proceedings of the 10$^{th}$ International Workshop on Inorganic and Organic Electroluminescence (Non-patent document 1), JP 2002-158093 A/2002 (Patent document 2), and JP H11-514143 A/1999 (Patent document 3). The 2,2'-bipyridyl compound described in Non-patent document 1 is low in glass transition temperature (hereinafter abbreviated as Tg), and not practically applicable. When the 2,2'-bipyridyl compound described in Patent document 2 is used for an organic EL device, the organic EL device can be driven at relatively low voltage, however, further decrease in voltage is desired for practical use. A specific compound is not shown in Patent document 3.

Patent document 1: JP 2003-123983 A/2003

Patent document 2: JP 2002-158093 A/2002

Patent document 3: JP H11-514143 A/1999

Non-patent document 1: Proceedings of the 10$^{th}$ International Workshop on Inorganic and Organic Electroluminescence.

DISCLOSURE OF THE INVENTION

Problems to be Solved by the Invention

The present invention has been made in light of the problems involved in such conventional techniques as described above, and an object of the present invention is to provide an electron transport material contributing to reduction of drive voltage and long life in an organic EL device. Further, an object of the present invention is to provide an organic EL device using the above electron transport material.

Means for Solving the Problems

Intensive investigations repeated by the present inventors have resulted in finding that an organic EL device which has high luminance and long life and which can be driven at low voltage can be obtained by using a compound having 2,3'-bipyridyl for an electron transport layer of the organic EL device, and they have completed the present invention based on the above knowledge.

The problems described above are solved by the respective items shown below.

[1] A compound represented by the following Formula (1):

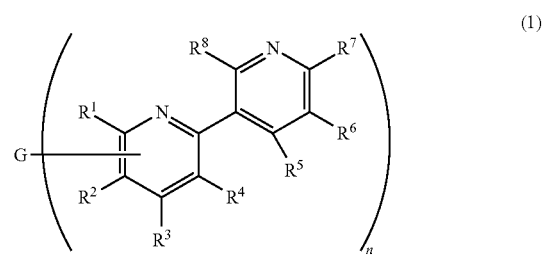

(1)

wherein G is an n-valent link, not a single bond, n is an integer of 2 to 4;
$R^1$ to $R^4$ are each independently hydrogen, a monovalent group, or a free valency bonded with G, $R^5$ to $R^8$ are each independently hydrogen or a monovalent group, and one of $R^1$ to $R^4$ is a free valency bonded with G; and n groups of 2,3'-bipyridyl may be the same or different with each other.

[2] The compound as described in the above item 1, wherein one of $R^1$ to $R_4$ is a free valency bonded with G, and others are hydrogen, and $R^5$ to $R^8$ are each independently hydrogen.

[3] The compound as described in the above item 2, wherein the compound is represented by the following Formula (2):

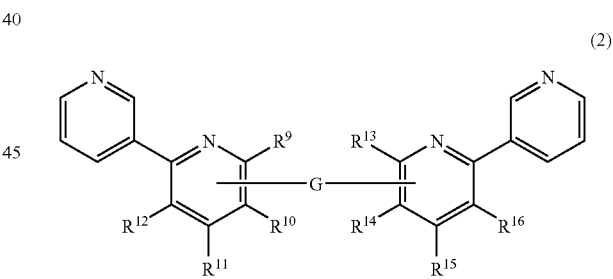

(2)

wherein G is one selected from a group consisting of groups represented by the following Formulas (G1) to (G3); one of $R^9$ to $R^{12}$ is a free valency bonded with G, and others are hydrogen; and one of $R^{13}$ to $R^{16}$ is a free valency bonded with G, and others are hydrogen:

(G1)

(G2)

(G3)

wherein $G^1$ is independently a divalent group derived from one selected from a group consisting of compounds represented by the following Formulas (A-1) to (A-20) and Formulas (B-1) to (B-42):

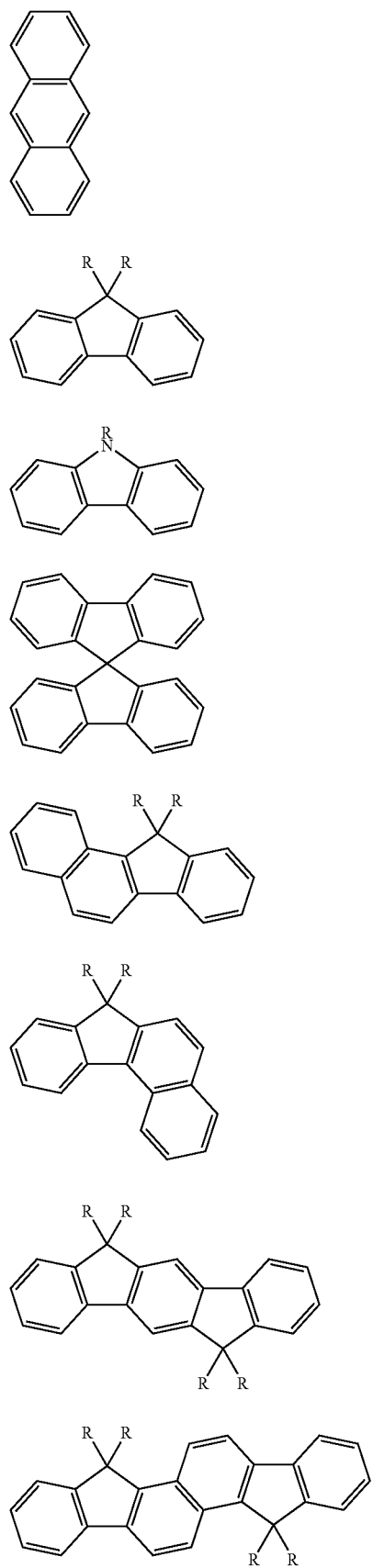
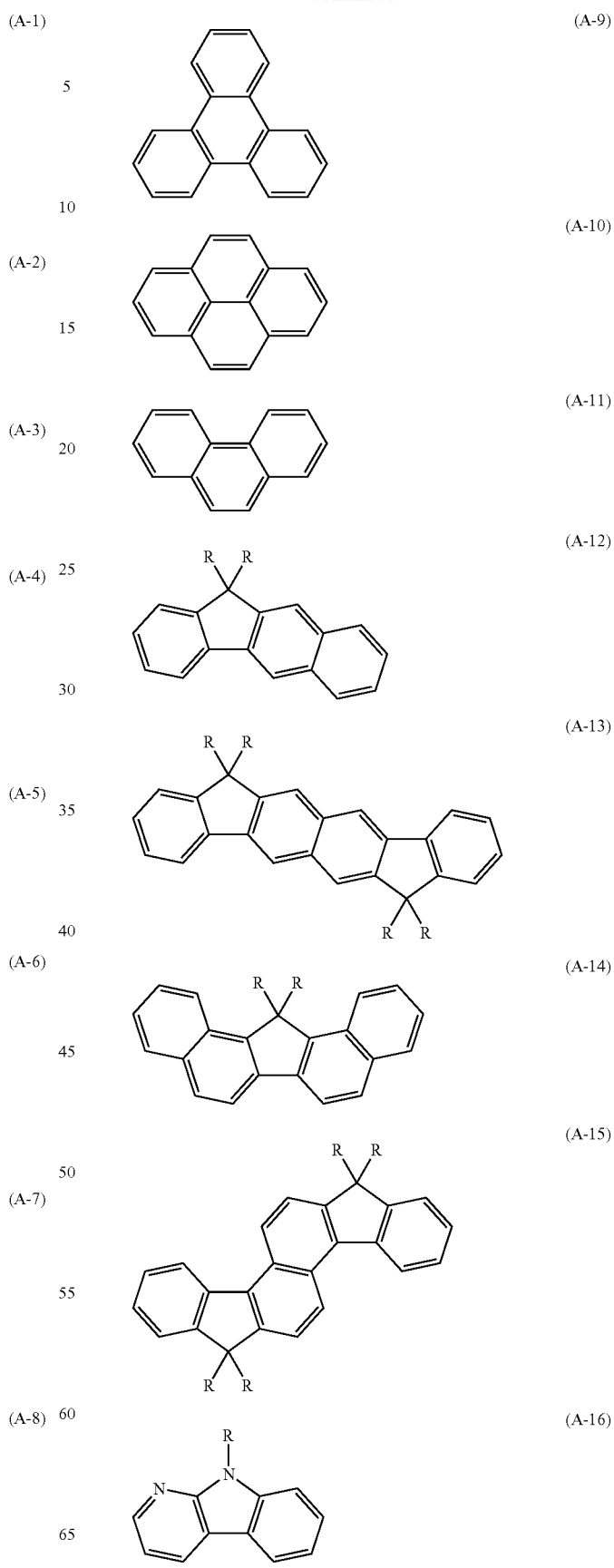

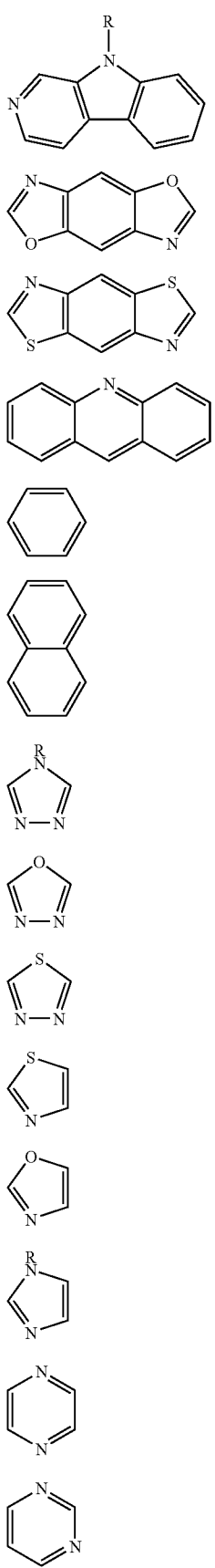
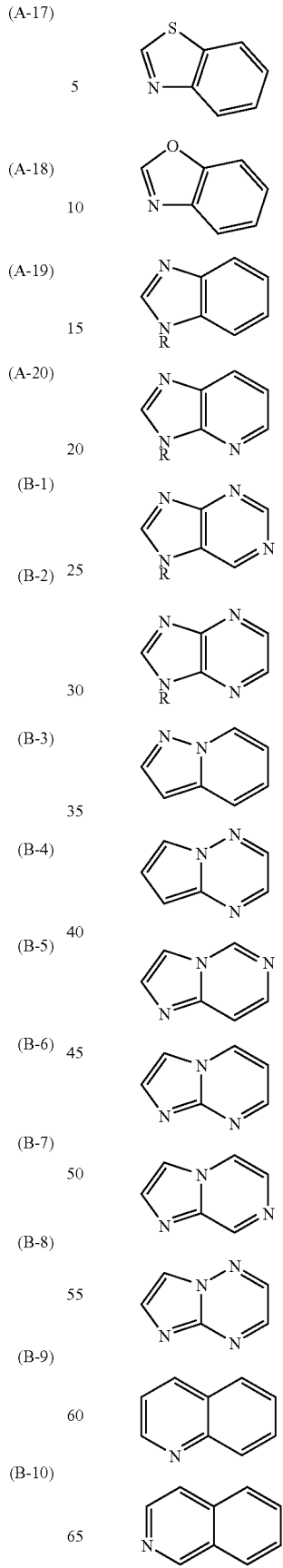

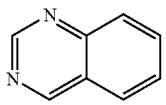
(B-25)

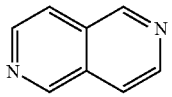
(B-26)

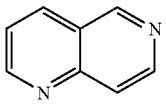
(B-27)

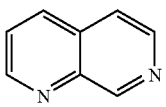
(B-28)

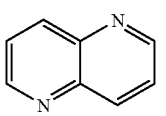
(B-29)

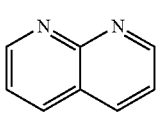
(B-30)

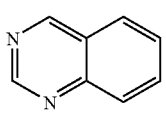
(B-31)

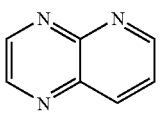
(B-32)

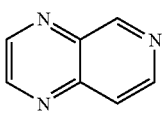
(B-33)

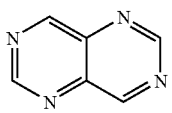
(B-34)

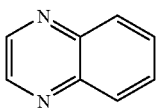
(B-35)

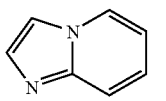
(B-36)

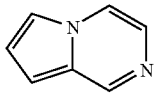
(B-37)

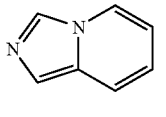
(B-38)

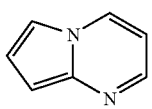
(B-39)

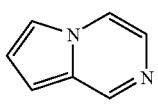
(B-40)

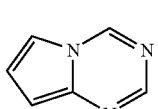
(B-41)

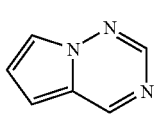
(B-42)

wherein R is independently hydrogen, methyl, ethyl, hexyl, cyclohexyl, phenyl, 1-naphthyl, or 2-naphthyl; and a divalent group derived from one selected from a group consisting of compounds represented by Formulas (A-1) to (A-20) and Formulas (B-1) to (B-42) may have a substituent on a position other than an atom having a free valency.

[4] The compound as described in the above item 3, wherein the compound is represented by the following Formula (2-1):

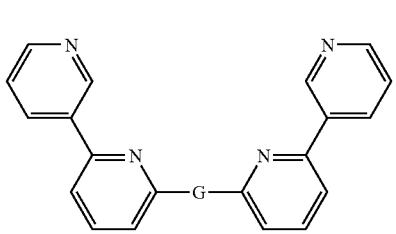

(2-1)

wherein a definition of G is the same with the definition of G in the Formula (2).

[5] The compound as described in the above item 4, wherein G is a link represented by Formula (G1), wherein $G^1$ is a divalent group derived from one selected from a group consisting of compounds represented by Formulas (A-1) to (A-20), and the above divalent group may have a substituent.

[6] The compound as described in the above item 4, wherein G is a link represented by Formula (G1), wherein $G^1$ is a divalent group derived from one selected from a group consisting of compounds represented by Formulas (A-1) to (A-10), and the above divalent group may have a substituent.

[7] The compound as described in the above item 4, wherein G is a link represented by Formula (G1), wherein $G^1$ is one selected from a group consisting of divalent groups represented by the following Formulas (C-1) to (C-15):

(C-1) 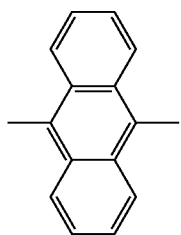
(C-2) 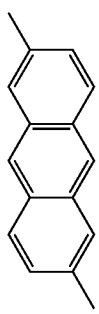
(C-3) 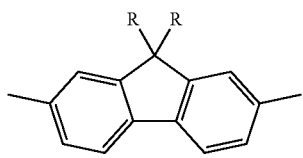
(C-4) 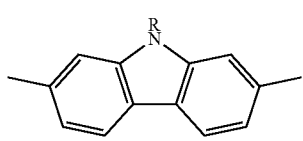
(C-5) 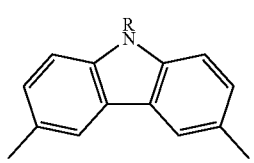
(C-6) 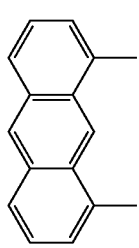
(C-7) 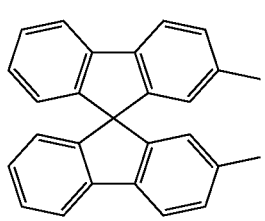
(C-8) 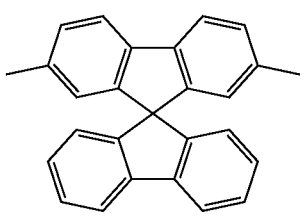
(C-9) 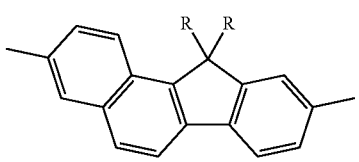
(C-10) 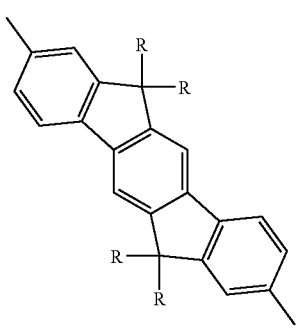
(C-11) 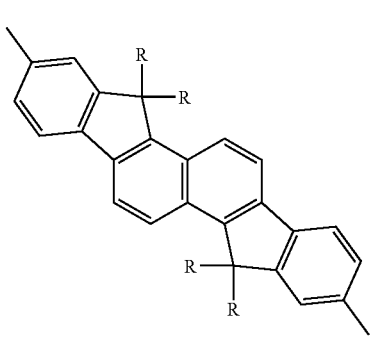
(C-12) 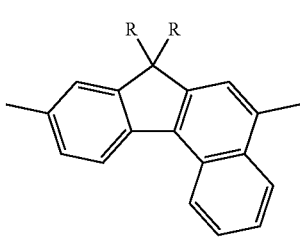
(C-13) 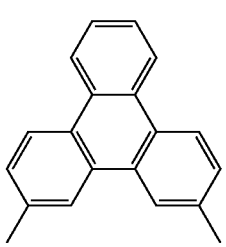

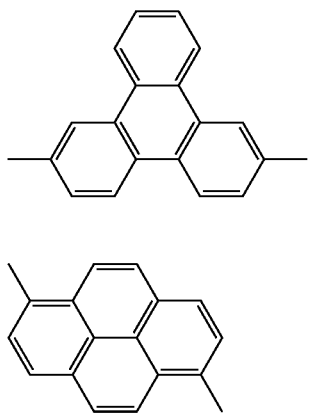

(C-14)

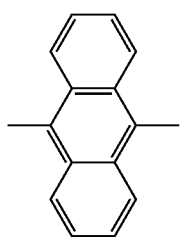

(C-15)

wherein R is independently hydrogen, methyl, ethyl, hexyl, cyclohexyl, phenyl, 1-naphthyl, or 2-naphthyl; and a divalent group represented by Formulas (C-1) to (C-15) may have a substituent on a position other than an atom having a free valency.

[8] The compound as described in the above item 4, wherein G is a link represented by Formula (G2), wherein $G^1$ is a same divalent group derived from one selected from a group consisting of compounds represented by Formulas (A-1) to (A-20) and Formulas (B-1) to (B-42), and the above divalent group may have a substituent.

[9] The compound as described in the above item 4, wherein G is a link represented by Formula (G2), wherein $G^1$ is a same divalent group derived from one selected from a group consisting of compounds represented by Formulas (A-1) to (A-10), and the above divalent group may have a substituent.

[10] The compound as described in the above item 4, wherein G is a link represented by Formula (G2), wherein G1 is a same group selected from a group consisting of divalent groups represented by the following Formulas (C-1) to (C-5):

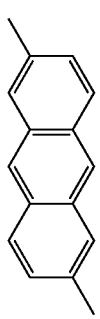

(C-1)

(C-2)

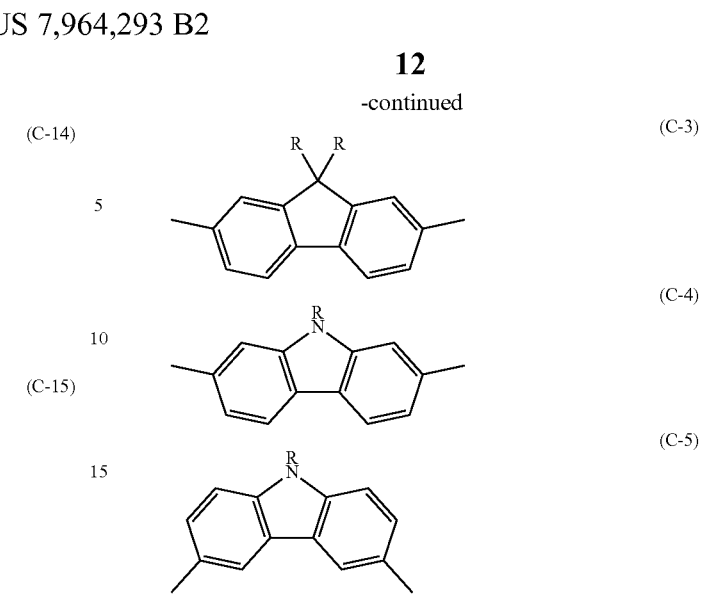

wherein R is independently hydrogen, methyl, ethyl, hexyl, cyclohexyl, phenyl, 1-naphthyl, or 2-naphthyl; and a divalent group represented by Formulas (C-1) to (C-5) may have a substituent on a position other than an atom having a free valency.

[11] The compound as described in the above item 4, wherein G is a link represented by the following Formulas (G3-1) to (G-3-3):

$$-G^{1B}-G^{1B}-G^{1B}-$$ (G3-1)

$$-G^{1A}-G^{1B}-G^{1A}-$$ (G3-2)

$$-G^{1B}-G^{1A}-G^{1B}-$$ (G3-3)

wherein $G^{1A}$ is independently a divalent group derived from one selected from a group consisting of compounds represented by Formulas (A-1) to (A-20), and the above divalent group may have a substituent; and $G^{1B}$ is independently a divalent group derived from one selected from a group consisting of compounds represented by Formulas (B-1) to (B-42), and the above divalent group may have a substituent.

[12] The compound as described in the above item 11, wherein G is a link represented by Formula (G3-1); and $G^{1B}$ is a same group selected from a group consisting of divalent groups represented by the following Formulas (D-1) to (D-15):

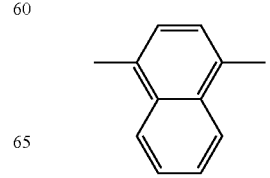

(D-1)

(D-2)

(D-3)

-continued

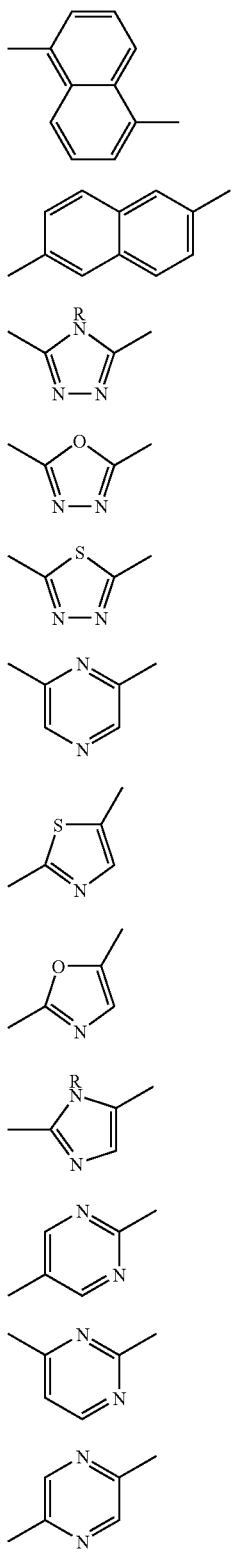

(D-4)
(D-5)
(D-6)
(D-7)
(D-8)
(D-9)
(D-10)
(D-11)
(D-12)
(D-13)
(D-14)
(D-15)

wherein R is independently hydrogen, methyl, ethyl, hexyl, cyclohexyl, phenyl, 1-naphthyl, or 2-naphthyl; and a divalent group represented by Formulas (D-1) to (D-15) may have a substituent on a position other than an atom having a free valency.

[13] The compound as described in the above item 11, wherein G is a link represented by Formula (G3-2); and $G^{1A}$ is a same group selected from a group consisting of divalent groups represented by Formulas (C-1) to (C-5), and $G^{1B}$ is a same group selected from a group consisting of divalent groups represented by Formulas (D-1) to (D-15).

[14] The compound as described in the above item 11, wherein G is a link represented by Formula (G3-3); and $G^{1A}$ is one selected from a group consisting of divalent groups represented by Formulas (C-1) to (C-5), and $G^{1B}$ is a same group selected from a group consisting of divalent groups represented by Formulas (D-1) to (D-15).

[15] The compound as described in the above item 11, wherein G is a link represented by the following Formula (G3-4):

$$-G^{1B2}-G^{1B1}-G^{1B2}-\qquad(G34)$$

wherein $G^{1B1}$ is one selected from a group consisting of divalent groups represented by Formulas (D-1) to (D-9), and $G^{1B2}$ is a same group selected from a group consisting of divalent groups represented by Formulas (D-1) to (D-15).

[16] The compound as described in the above item 3, wherein the compound is represented by the following Formula (2-2):

(2-2)

wherein a definition of G is the same with the definition of G in Formula (2).

[17] The compound as described in the above item 16, wherein G is a link represented by Formula (G1), wherein $G^1$ is a divalent group derived from one selected from a group consisting of compounds represented by Formulas (A-1) to (A-20), and the above divalent group may have a substituent.

[18] The compound as described in the above item 16, wherein G is a link represented by Formula (G1), wherein $G^1$ is a divalent group derived from one selected from a group consisting of compounds represented by Formulas (A-1) to (A-10), and the above divalent group may have a substituent.

[19] The compound as described in the above item 16, wherein G is a link represented by Formula (G1), wherein $G^1$ is one selected from a group consisting of divalent groups represented by Formulas (C-1) to (C-15).

[20] The compound as described in the above item 16, wherein G is a link represented by Formula (G2), wherein $G^1$ is a same divalent group derived from one selected from a group consisting of compounds represented by Formulas (A-1) to (A-20) and Formulas (B-1) to (B-42), and the above divalent group may have a substituent.

[21] The compound as described in the above item 16, wherein G is a link represented by Formula (G2), wherein $G^1$ is a same divalent group derived from one selected from a group consisting of compounds represented by Formulas (A-1) to (A-10), and the above divalent group may have a substituent.

[22] The compound as described in the above item 16, wherein G is a link represented by Formula (G2), wherein G1 is a same group selected from a group consisting of divalent groups represented by Formulas (C-1) to (C-5).

[23] The compound as described in the above item 16, wherein G is a link represented by the following Formulas (G3-1) to (G3-3):

  (G3-1)

  (G3-2)

  (G3-3)

wherein $G^{1A}$ is independently a divalent group derived from one selected from a group consisting of compounds represented by Formulas (A-1) to (A-20), and the above divalent group may have a substituent; and $G^{1B}$ is independently a divalent group derived from one selected from a group consisting of compounds represented by Formulas (B-1) to (B-42), and the above divalent group may have a substituent.

[24] The compound as described in the above item 23, wherein G is a link represented by Formula (G3-1); and $G^{1B}$ is a same group selected from a group consisting of divalent groups represented by Formulas (D-1) to (D-15).

[25] The compound as described in the above item 23, wherein G is a link represented by Formula (G3-2); and $G^{1A}$ is a same group selected from a group consisting of divalent groups represented by Formulas (C-1) to (C-5), and $G^{1B}$ is one selected from a group consisting of divalent groups represented by Formulas (D-1) to (D-15).

[26] The compound as described in the above item 23, wherein G is a link represented by Formula (G3-3); and $G^{1A}$ is one selected from a group consisting of divalent groups represented by Formulas (C-1) to (C-5), and $G^{1B}$ is a same group selected from a group consisting of divalent groups represented by Formulas (D-1) to (D-15).

[27] The compound as described in the above item 23, wherein G is a link represented by the following Formula (G3-4):

  (G34)

wherein $G^{1B1}$ is one selected from a group consisting of divalent groups represented by Formulas (D-1) to (D-9), and $G^{1B2}$ is a same group selected from a group consisting of divalent groups represented by Formulas (D-1) to (D-15).

[28] The compound as described in the above item 3, wherein the compound is represented by the following Formula (2-3):

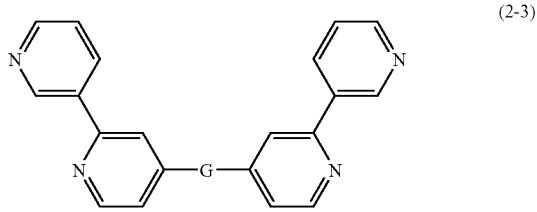  (2-3)

wherein a definition of G is the same with the definition of G in Formula (2).

[29] The compound as described in the above item 28, wherein G is a link represented by Formula (G1), wherein $G^1$ is a divalent group derived from one selected from a group consisting of compounds represented by Formulas (A-1) to (A-20), and the above divalent group may have a substituent.

[30] The compound as described in the above item 28, wherein G is a link represented by Formula (G1), wherein $G^1$ is a divalent group derived from one selected from a group consisting of compounds represented by Formulas (A-1) to (A-10), and the above divalent group may have a substituent.

[31] The compound as described in the above item 28, wherein G is a link represented by Formula (G1), wherein $G^1$ is one selected from a group consisting of divalent groups represented by Formulas (C-1) to (C-15).

[32] The compound as described in the above item 28, wherein G is a link represented by Formula (G2), wherein $G^1$ is a same divalent group derived from one selected from a group consisting of compounds represented by Formulas (A-1) to (A-20) and Formulas (B-1) to (B-42), and the above divalent group may have a substituent.

[33] The compound as described in the above item 28, wherein G is a link represented by Formula (G2), wherein $G^1$ is a same divalent group derived from one selected from a group consisting of compounds represented by Formulas (A-1) to (A-10), and the above divalent group may have a substituent.

[34] The compound as described in the above item 28, wherein G is a link represented by Formula (G2), wherein $G^1$ is a same group selected from a group consisting of divalent groups represented by Formulas (C-1) to (C-5), and the above divalent group may have a substituent.

[35] The compound as described in the above item 28, wherein G is a link represented by the following Formulas (G3-1) to (G3-3):

  (G3-1)

  (G3-2)

  (G3-3)

wherein $G^{1A}$ is independently a divalent group derived from one selected from a group consisting of compounds represented by Formulas (A-1) to (A-20), and the above divalent group may have a substituent; and $G^{1B}$ is independently a divalent group derived from one selected from a group consisting of compounds represented by Formulas (B-1) to (B-42), and the above divalent group may have a substituent.

[36] The compound as described in the above item 35, wherein G is a link represented by Formula (G3-1); and $G^{1B}$ is a same group selected from a group consisting of divalent groups represented by Formulas (D-1) to (D-15).

[37] The compound as described in the above item 35, wherein G is a link represented by Formula (G3-2); and $G^{1A}$ is a same group selected from a group consisting of divalent groups represented by Formulas (C-1) to (C-5), and $G^{1B}$ is one selected from a group consisting of divalent groups represented by Formulas (D-1) to (D-15).

[38] The compound as described in the above item 35, wherein G is a link represented by Formula (G3-3); and $G^{1A}$ is one selected from a group consisting of divalent groups represented by Formulas (C-1) to (C-5), and $G^{1B}$ is a same group selected from a group consisting of divalent groups represented by Formulas (D-1) to (D-15).

[39] The compound as described in the above item 35, wherein G is a link represented by the following Formula (G3-4):

  (G34)

wherein $G^{1B}$ is one selected from a group consisting of divalent groups represented by Formulas (D-1) to (D-9), and $G^{1B2}$ is a same group selected from a group consisting of divalent groups represented by Formulas (D-1) to (D-15).

[40] The compound as described in the above item 3, wherein the compound is represented by the following Formula (2-4):

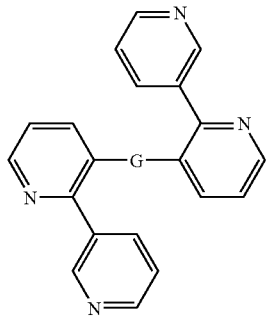
(2-4)

wherein a definition of G is the same with the definition of G in Formula (2).

[41] The compound as described in the above item 40, wherein G is a link represented by Formula (G1), wherein $G^1$ is a divalent group derived from one selected from a group consisting of compounds represented by Formulas (A-1) to (A-20), and the above divalent group may have a substituent.

[42] The compound as described in the above item 40, wherein G is a link represented by Formula (G1), wherein $G^1$ is a divalent group derived from one selected from a group consisting of compounds represented by Formulas (A-1) to (A-10), and the above divalent group may have a substituent.

[43] The compound as described in the above item 40, wherein G is a link represented by Formula (G1), wherein $G^1$ is one selected from a group consisting of divalent groups represented by Formulas (C-1) to (C-15).

[44] The compound as described in the above item 40, wherein G is a link represented by Formula (G2), wherein $G^1$ is a same divalent group derived from one selected from a group consisting of compounds represented by Formulas (A-1) to (A-20) and Formulas (B-1) to (B-42), and the above divalent group may have a substituent.

[45] The compound as described in the above item 40, wherein G is a link represented by Formula (G2), wherein $G^1$ is a same divalent group derived from one selected from a group consisting of compounds represented by Formulas (A-1) to (A-10), and the above divalent group may have a substituent.

[46] The compound as described in the above item 40, wherein G is a link represented by Formula (G2), wherein $G^1$ is a same group selected from a group consisting of divalent groups represented by Formulas (C-1) to (C-5).

[47] The compound as described in the above item 40, wherein G is a link represented by the following Formulas (G3-1) to (G3-3):

$-G^{1B}-G^{1B}-G^{1B}-$ (G3-1)

$-G^{1A}-G^{1B}-G^{1A}-$ (G3-2)

$-G^{1B}-G^{1A}-G^{1B}-$ (G3-3)

wherein $G^{1A}$ is independently a divalent group derived from one selected from a group consisting of compounds represented by Formulas (A-1) to (A-20), and the above divalent group may have a substituent; and $G^{1B}$ is independently a divalent group derived from one selected from a group consisting of compounds represented by Formulas (B-1) to (B-42), and the above divalent group may have a substituent.

[48] The compound as described in the above item 47, wherein G is a link represented by Formula (G3-1); and $G^{1B}$ is a same group selected from a group consisting of divalent groups represented by Formulas (D-1) to (D-15).

[49] The compound as described in the above item 47, wherein G is a link represented by Formula (G3-2); and $G^{1A}$ is one selected from a group consisting of divalent groups represented by Formulas (C-1) to (C-5), and $G^{1B}$ is a same group selected from a group consisting of divalent groups represented by Formulas (D-1) to (D-15).

[50] The compound as described in the above item 47, wherein G is a link represented by Formula (G3-3); and $G^{1A}$ is one selected from a group consisting of divalent groups represented by Formulas (C-1) to (C-5), and $G^{1B}$ is a same group selected from a group consisting of divalent groups represented by Formulas (D-1) to (D-15).

[51] The compound as described in the above item 47, wherein G is a link represented by the following Formula (G3-4):

$-G^{1B2}-G^{1B1}-G^{1B2}-$ (G34)

wherein $G^{1B1}$ is one selected from a group consisting of divalent groups represented by Formulas (D-1) to (D-9), and $G^{1B2}$ is a same group selected from a group consisting of divalent groups represented by Formulas (D-1) to (D-15).

[52] The compound as described in the above item 3, wherein the compound is represented by the following Formula (2-5):

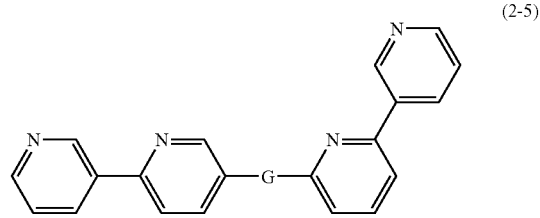
(2-5)

wherein a definition of G is the same with the definition of G in Formula (2).

[53] The compound as described in the above item 52, wherein G is a link represented by Formula (G1), wherein $G^1$ is a divalent group derived from one selected from a group consisting of compounds represented by Formulas (A-1) to (A-20), and the above divalent group may have a substituent.

[54] The compound as described in the above item 52, wherein G is a link represented by Formula (G1), wherein $G^1$ is a divalent group derived from one selected from a group consisting of compounds represented by Formulas (A-1) to (A-10), and the above divalent group may have a substituent.

[55] The compound as described in the above item 52, wherein G is a link represented by Formula (G1), wherein $G^1$ is one selected from a group consisting of divalent groups represented by Formulas (C-1) to (C-17).

[56] The compound as described in the above item 3, wherein the compound is represented by the following Formula (2-6):

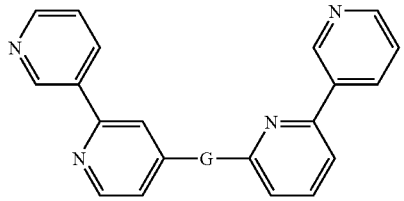

(2-6)

wherein a definition of G is the same with the definition of G in Formula (2).

[57] The compound as described in the above item 56, wherein. G is a link represented by Formula (G1), wherein $G^1$ is a divalent group derived from one selected from a group consisting of compounds represented by Formulas (A-1) to (A-20), and the above divalent group may have a substituent.

[58] The compound as described in the above item 56, wherein G is a link represented by Formula (G1), wherein $G^1$ is a divalent group derived from one selected from a group consisting of compounds represented by Formulas (A-1) to (A-10), and the above divalent group may have a substituent.

[59] The compound as described in the above item 56, wherein G is a link represented by Formula (G1), wherein $G^1$ is one selected from a group consisting of divalent groups represented by Formulas (C-1) to (C-17).

[60] The compound as described in the above item 3, wherein the compound is represented by the following Formula (2-7):

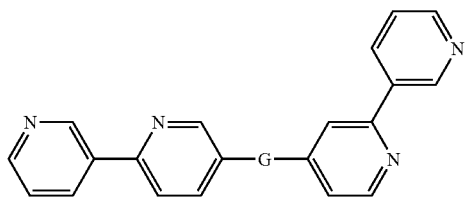

(2-7)

wherein a definition of G is the same with the definition of G in Formula (2).

[61] The compound as described in the above item 60, wherein G is a link represented by Formula (G1), wherein $G^1$ is a divalent group derived from one selected from a group consisting of compounds represented by Formulas (A-1) to (A-20), and the above divalent group may have a substituent.

[62] The compound as described in the above item 60, wherein G is a link represented by Formula (G1), wherein $G^1$ is a divalent group derived from one selected from a group consisting of compounds represented by Formulas (A-1) to (A-10), and the above divalent group may have a substituent.

[63] The compound as described in the above item 60, wherein G is a link represented by Formula (G1), wherein $G^1$ is one selected from a group consisting of divalent groups represented by Formulas (C-1) to (C-17).

[64] The compound as described in the above item 2, wherein the compound is represented by the following Formula (3):

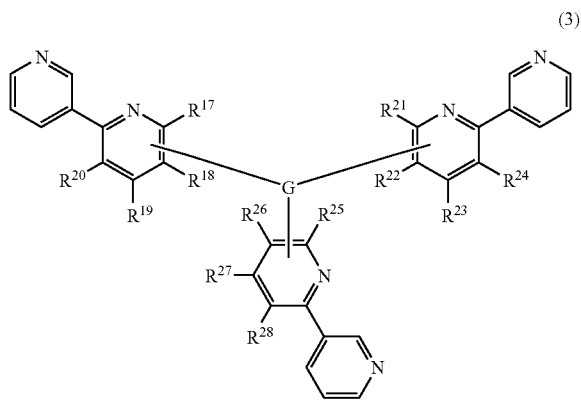

(3)

wherein G is a group represented by the following Formula (G4) or (G5); one of $R^{17}$ to $R^{20}$ is a free valency bonded with G, and others are hydrogen; one of $R^{21}$ to $R^{24}$ is a free valency bonded with G, and others are hydrogen; and one of $R^{25}$ to $R^{28}$ is a free valency bonded with G, and others are hydrogen,

(G4)

(G5)

wherein $G^1$ is independently a divalent group derived from one selected from a group consisting of compounds represented by Formulas (A-1) to (A-20) and Formulas (B-1) to (B-42); $G^{2A}$ is one selected from a group consisting of trivalent groups represented by the following Formulas (E-1) to (E-10), and $G^{2B}$ is boron, nitrogen, a phosphoryl group, or one selected from a group consisting of trivalent groups represented by Formulas (E-1) to (E-10):

(E-1)

(E-2)

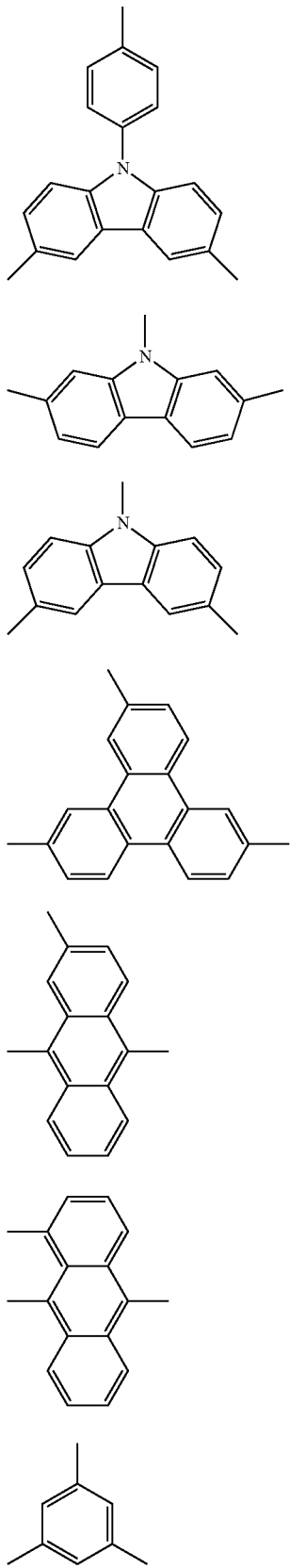

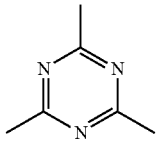

[65] The compound as described in the above item 64, wherein G is a link represented by Formula (G5), and $G^1$ is the same.

[66] The compound as described in the above item 2, wherein the compound is represented by the following Formula (4):

(4)

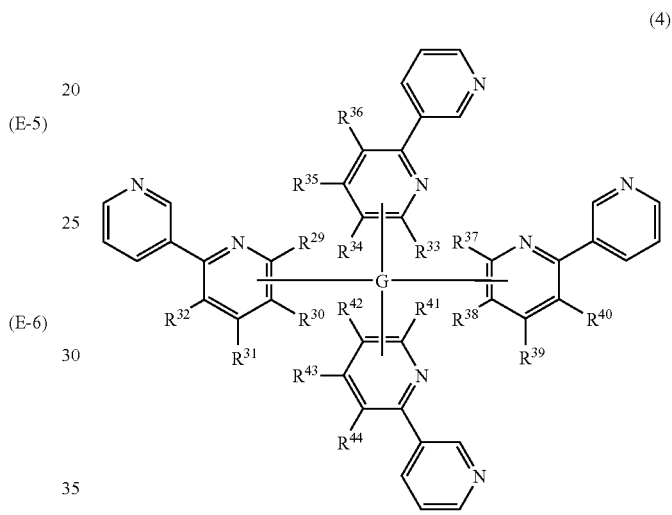

wherein G is a group represented by the following Formula (G6) or (G7); one of $R^{29}$ to $R^{32}$ is a free valency bonded with G, and others are hydrogen; one of $R^{33}$ to $R^{36}$ is a free valency bonded with G, and others are hydrogen; one of $R^{37}$ to $R^{40}$ is a free valency bonded with G, and others are hydrogen; and one of $R^{41}$ to $R^{44}$ is a free valency bonded with G, and others are hydrogen:

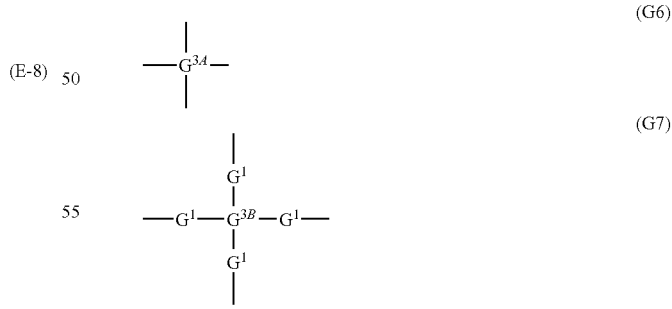

wherein $G^1$ is independently a divalent group derived from one selected from a group consisting of compounds represented by Formulas (A-1) to (A-20) and Formulas (B-1) to (B-42); $G^{3A}$ is one selected from a group consisting of tetravalent groups represented by the following Formulas (F-1) to (F-8); and $G^{3B}$ is carbon, silicon, or one selected from tetravalent groups represented by (F-1) to (F-8).

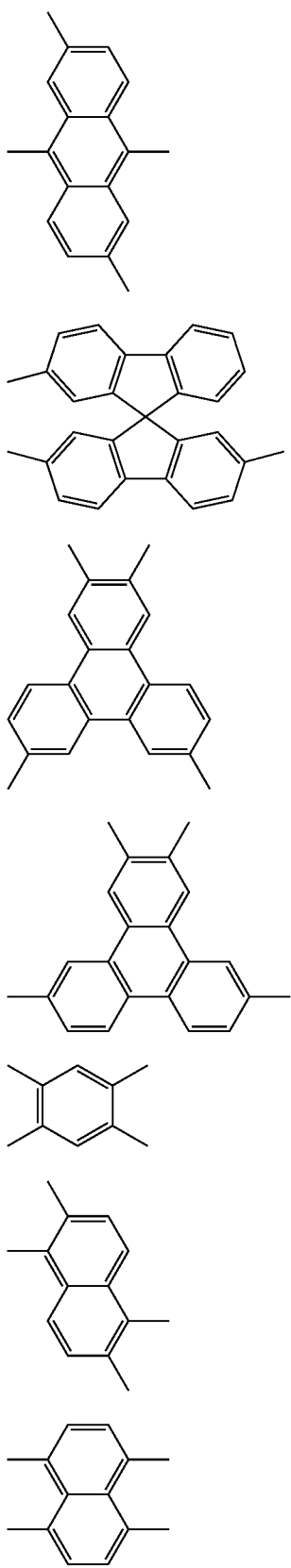

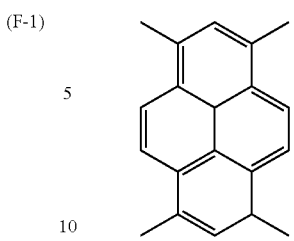

[67] The compound as described in the above item 66, wherein G is a link represented by Formula (G7), wherein $G^1$ is the same.

[68] The compound as described in the above item 4, wherein G is anthracene-9,10-diyl.

[69] The compound as described in the above item 16, wherein G is anthracene-9,10-diyl.

[70] The compound as described in the above item 4, wherein G is 2-phenylanthracene-9,10-diyl.

[71] The compound as described in the above item 16, wherein G is 2-phenylanthracene-9,10-diyl.

[72] The compound as described in the above item 4, wherein G is 2-t-butylanthracene-9,10-diyl.

[73] The compound as described in the above item 16, wherein G is 2-t-butylanthracene-9,10-diyl.

[74] The compound as described in the above item 4, wherein G is 2-methylanthracene-9,10-diyl.

[75] The compound as described in the above item 16, wherein G is 2-methylanthracene-9,10-diyl.

[76] The compound as described in the above item 4, wherein G is 7,7-diphenylbenzo[c]fluorene-5,9-diyl.

[77] The compound as described in the above item 16, wherein G is 7,7-diphenylbenzo[c]fluorene-5,9-diyl.

[78] An organic electroluminescent device comprising the compound as described in any one of the above items 1 to 77.

[79] An organic electroluminescent device comprising at least a hole transport layer, an emission layer, and an electron transport layer sandwiched between an anode and a cathode on a substrate, wherein the above electron transport layer comprises the compound as described in any one of the above items 1 to 77.

Effects of the Invention

A compound of the present invention is characteristic to be stable even when voltage is applied in a thin film state, and high in charge transport capacity. The compound of the present invention is suitable as a charge transport material in an organic EL device. An organic EL device which has long life and which can be driven at low voltage can be obtained by using the compound of the present invention for an electron transport layer of the organic EL device. A high performance display unit for full color display and so forth can be produced by using the organic EL device of the present invention.

BEST MODE FOR CARRYING OUT THE INVENTION

In the following, the present invention is explained in more detail.
<Explanation of a Compound>
The first present invention refers to a compound having a 2,3'-bipyridyl group represented by the following Formula (1):

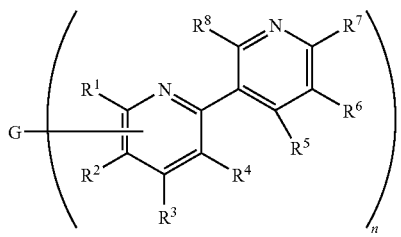

(1)

wherein G is an n-valent link, not a single bond. The n-valent link is a generic term that means an n-valent atom, an n-valent group, and a ring having n free valencies, and the n-valent link may be constituted by combining the above atom, group, and/or ring. Also when an n-valent link is unsymmetrical in structure, n groups of 2,3'-bipyridyl may be bonded to an optional position of the above link. Detailed explanation on the n-valent link G is described later.

In the present specification, a group formed by $R^1$ to $R^8$ and a 2,3'-bipyridyl nucleus is referred to as a 2,3'-bipyridyl group. One of $R^1$ to $R^4$ in the 2,3'-bipyridyl group is a free valency bonded with G, and others are each independently hydrogen or a monovalent group. $R^5$ to $R^8$ are each independently hydrogen or a monovalent group. N groups of 2,3'-bipyridyl may be the same or different with each other, preferably, the same. The description of "n free valencies" in the link G and the "free valency bonded with G" in the 2,3'-bipyridyl group as described above does not represent that G and the 2,3'-bipyridyl group exist in the form of a free radical (radical). The "free valency" means a so-called "bonding hand" which bonds with another group or atom through a covalent bond. More specifically, the description of "one of $R^1$ to $R^4$ in a 2,3'-bipyridyl group is a free valency bonded with G" represents a state where any one of $R^1$ to $R^4$ in the 2,3'-bipyridyl group bonds with an optional position of the link G.

A monovalent group in $R^1$ to $R^8$ is a nitro group, a cyano group, a dimesitylboryl group, aryl having 6 to 12 carbon atoms, or alkyl having 1 to 12 carbon atoms. The above alkyl may be a straight or branched chain, or in the form of a ring. A specific example of the monovalent group is phenyl, 2-biphenylyl, 3-biphenylyl, 4-biphenylyl, 1-naphthyl, 2-naphthyl, methyl, t-butyl, or cyclohexyl. $R^5$ to $R^8$ are each preferably hydrogen.

For a 2,3'-bipyridyl group, $R^1$, $R^2$, or $R^3$ preferably bonds with G. $R^1$ to $R^4$ which are not involved in bonding with G are preferably hydrogen.

In Formula (1), n is most preferably 2, more preferably, 3, preferably, 4. One of reasons thereof is easiness to produce a compound. A second reason is an expected advantage of facilitating to form a film during producing an organic EL device because a molecular weight does not extremely increase, and subliming ability is considered to be comparatively improved.

<Compound in which n is 2>

A compound in which n is 2 is represented by the following Formula (2) in detail:

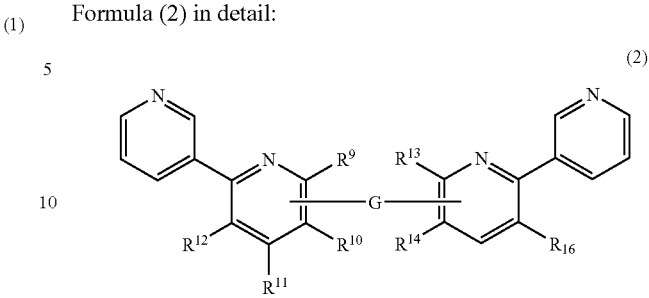

(2)

One of $R^9$ to $R^{12}$ is a free valency bonded with G, and others are hydrogen. In this case, $R^9$, $R^{10}$, or $R^{11}$ preferably bonds with G. One of $R^{13}$ to $R^{16}$ is a free valency bonded with G, and others are hydrogen. In this case, $R^{13}$, $R^{14}$, or $R^{15}$ preferably bonds with G. Two groups of 2,3'-bipyridyl may be the same or different with each other, preferably, the same.

G is one selected from a group consisting of links represented by the following Formulas (G1) to (G3). In the Formulas (G2) and (G3), $G^1$ may be the same or different with each other.

-$G^1$- (G1)

-$G^1$-$G^1$- (G2)

-$G^1$-$G^1$-$G^1$- (G3)

$G^1$ is independently a divalent group derived from one selected from a group consisting of compounds represented by the following Formulas (A-1) to (A-20) and Formulas (B-1) to (B-42) Hereinafter, a group consisting of compounds represented by Formulas (A-1) to (A-20) or (B-1) to (B-42) is referred to as A group or B group occasionally.

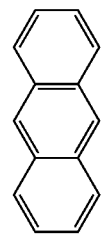

(A-1)

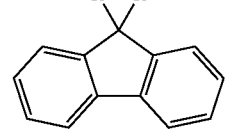

(A-2)

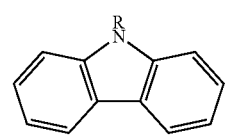

(A-3)

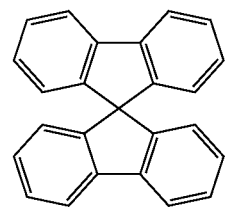

(A-4)

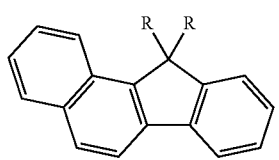
(A-5)
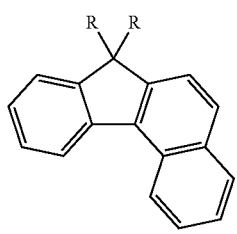
(A-6)
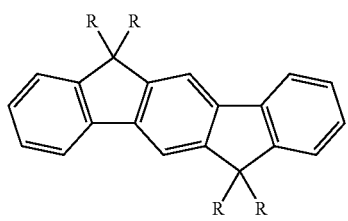
(A-7)
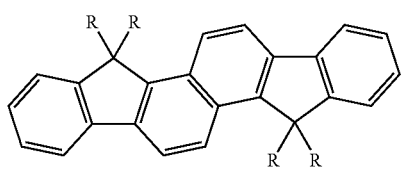
(A-8)
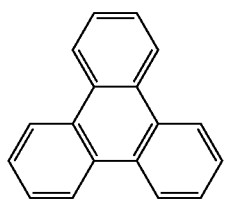
(A-9)
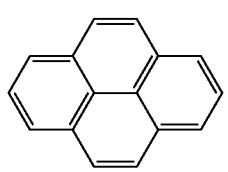
(A-10)
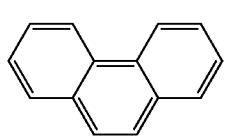
(A-11)
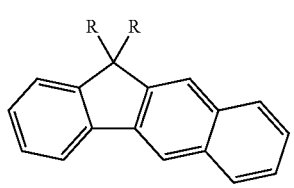
(A-12)
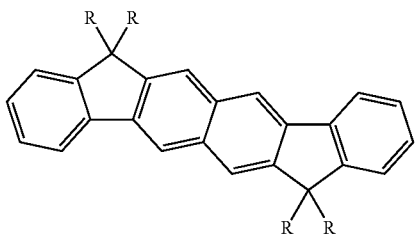
(A-13)
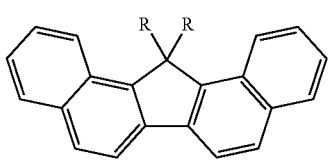
(A-14)
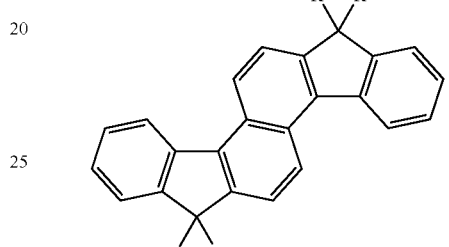
(A-15)
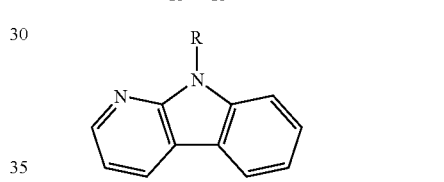
(A-16)
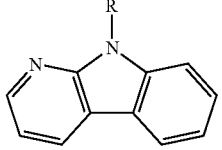
(A-17)
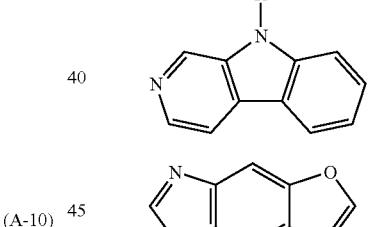
(A-18)
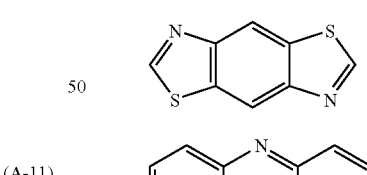
(A-19)
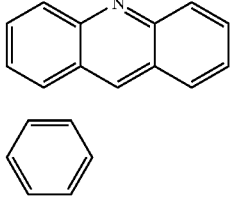
(A-20)
(B-1)
(B-2)

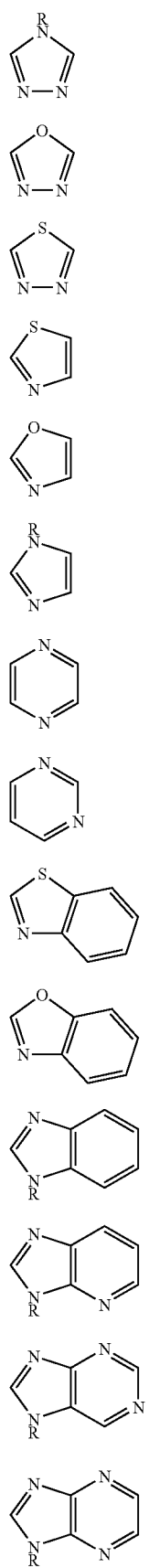
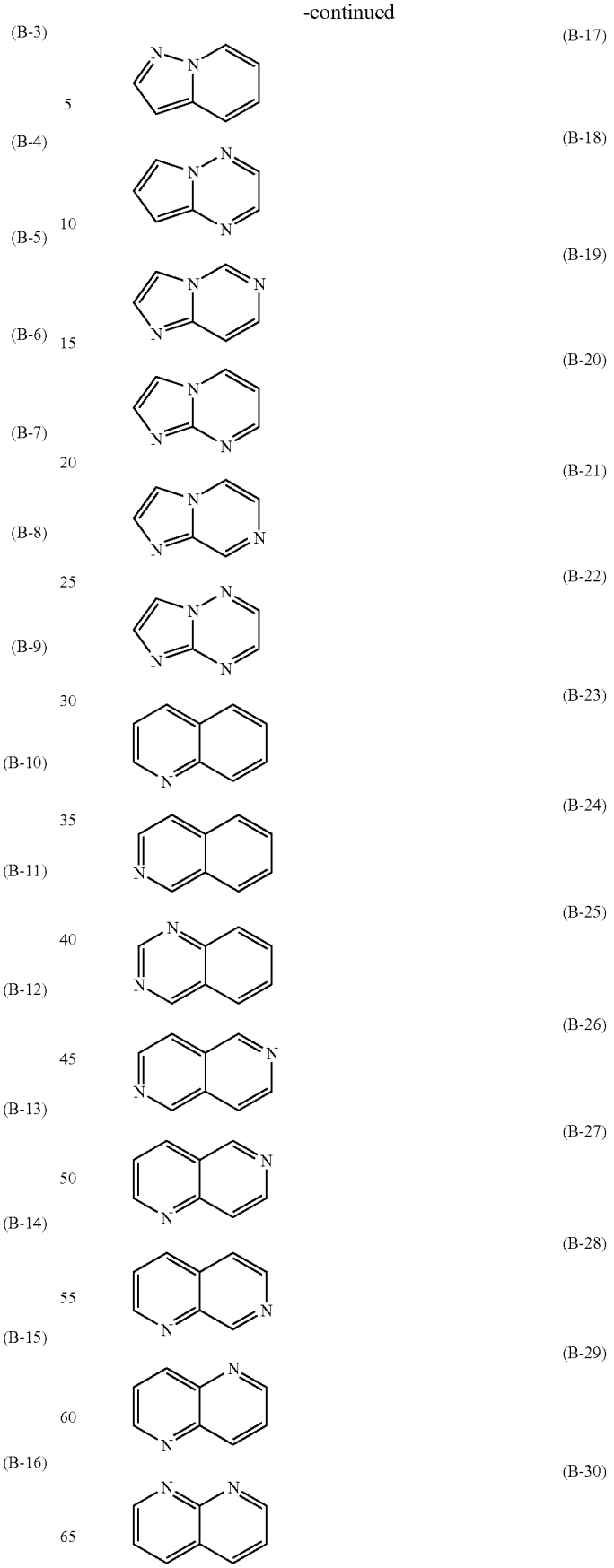

-continued

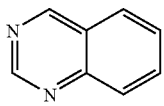 (B-31)

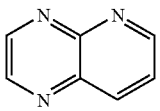 (B-32)

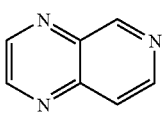 (B-33)

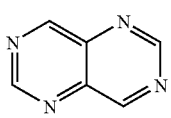 (B-34)

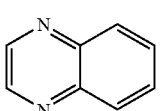 (B-35)

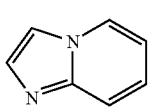 (B-36)

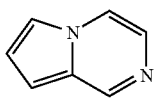 (B-37)

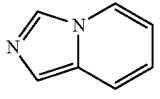 (B-38)

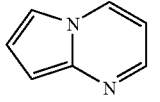 (B-39)

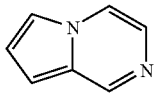 (B-40)

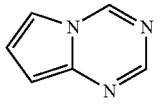 (B-41)

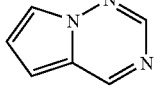 (B-42)

R is independently hydrogen, methyl, ethyl, hexyl, cyclohexyl, phenyl, 1-naphthyl, or 2-naphthyl.

A divalent group derived from one selected from a group consisting of compounds represented by Formulas (A-1) to (A-20) and Formulas (B-1) to (B-42) may have a substituent on a position other than an atom having a free valency. A specific example of the substituent is phenyl, 2-biphenylyl, 3-biphenylyl, 4-biphenylyl, 1-naphthyl, 2-naphthyl, methyl, t-butyl, or cyclohexyl.

<Compound in which n is 3>

A compound in which n is 3 is represented by the following Formula (3) in detail:

(3)

[Structure showing tris(2,3'-bipyridyl) compound with G linker and substituents $R^{17}$ through $R^{28}$]

One of $R^{17}$ to $R^{20}$ is a free valency linked with G, and others are hydrogen. In this case, $R^{17}$, $R^{18}$, or $R^{19}$ preferably bonds with G. One of $R^{21}$ to $R^{24}$ is a free valency linked with G, and others are hydrogen. In this case, $R^{21}$, $R^{22}$, or $R^{23}$ preferably bonds with G. One of $R^{25}$ to $R^{28}$ is a free valency linked with G, and others are hydrogen. In this case, $R^{25}$, $R^{26}$, or $R^{27}$ preferably bonds with G. Three groups of 2,3'-bipyridyl may be the same or different with each other, preferably, the same.

G is a link represented by the following Formula (G4) or (G5). In the Formula (G5), $G^1$ may be the same or different with each other, preferably, the same.

(G4)

$$\diagdown_{G^{2A}}\diagup$$
$$|$$

(G5)

$$\diagdown_{G^1}\diagdown_{G^{2B}}\diagup^{G^1}$$
$$|$$
$$G^1$$
$$|$$

$G^1$ is independently a divalent group derived from one selected from a group consisting of compounds in the A group and the B group as described above.

$G^{2A}$ is one selected from a group consisting of trivalent groups represented by the following Formulas (E-1) to (E-10), and $G^{2B}$ is boron, nitrogen, a phosphoryl group, or one selected from a group consisting of trivalent groups represented by the Formulas (E-1) to (E-10).

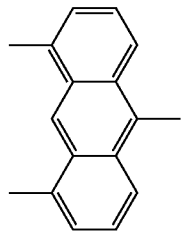 (E-1)

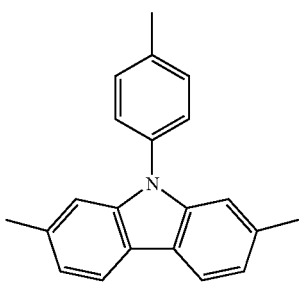
(E-2)

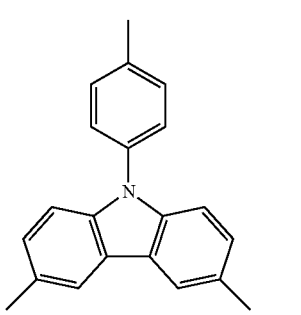
(E-3)

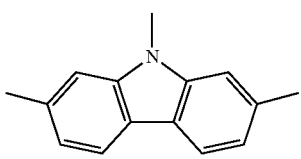
(E-4)

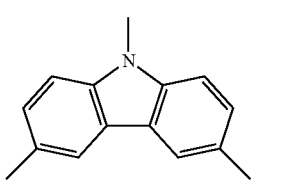
(E-5)

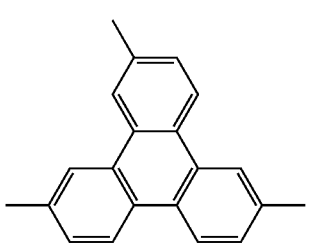
(E-6)

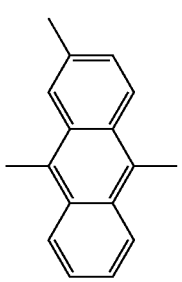
(E-7)

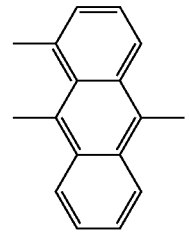
(E-8)

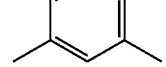
(E-9)

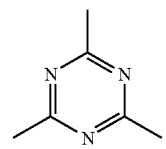
(E-10)

<Compound in which n is 4>

A compound in which n is 4 is represented by the following Formula (4) in detail:

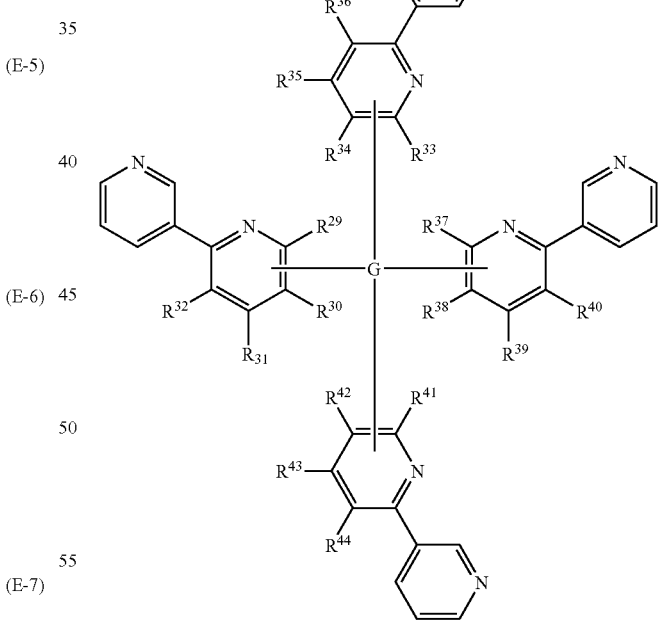
(4)

One of $R^{29}$ to $R^{32}$ is a free valency linked with G, and others are hydrogen. In this case, $R^{29}$, $R^{30}$, or $R^{31}$ preferably bonds with G. One of $R^{33}$ to $R^{36}$ is a free valency linked with G, and others are hydrogen. In this case, $R^{33}$, $R^{34}$, or $R^{35}$ preferably bonds with G. One of $R^{37}$ to $R^{40}$ is a free valency linked with G, and others are hydrogen. In this case, $R^{37}$, $R^{38}$, or $R^{39}$ preferably bonds with G. One of $R^{41}$ to $R^{44}$ is a free valency linked with G, and others are hydrogen. In this case, $R^{41}$, $R^{42}$, or $R^{43}$ preferably bonds with G. Four groups of 2,3'-bipyridyl may be the same or different with each other, preferably, the same.

G is a link represented by the following Formula (G6) or (G7). In the Formula (G7), G1 may be the same or different with each other, preferably, the same.

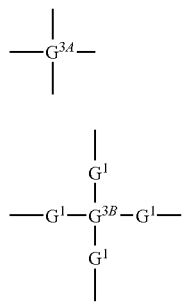
(G6)

(G7)

$G^1$ is independently a divalent group derived from one selected from a group consisting of compounds in the A group and the B group as described above.

$G^{3A}$ is one selected from a group consisting of tetravalent groups represented by the following Formulas (F-1) to (F-8), and $G^{3B}$ is carbon, silicon, or one selected from a group consisting of tetravalent groups represented by the Formulas (F-1) to (F-8).

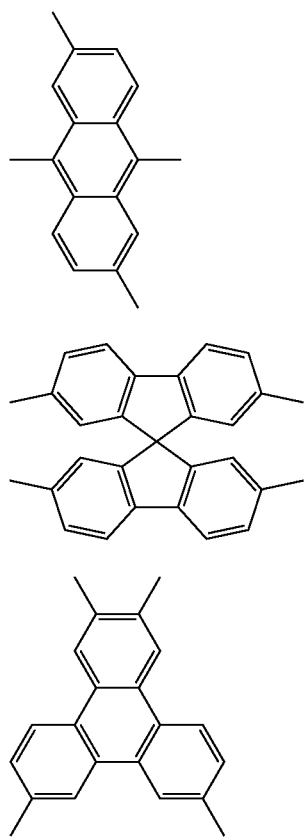

(F-1)

(F-2)

(F-3)

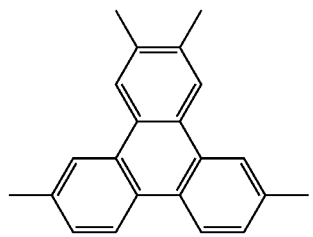
(F-4)

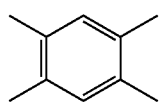
(F-5)

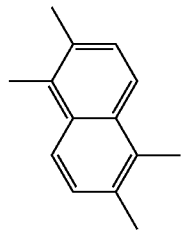
(F-6)

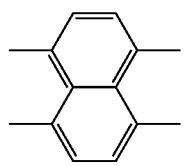
(F-7)

(F-8)

<More Detailed Explanation of Compound in which n is 2>

A preferable compound in which n is 2 is represented by the following Formulas (2-1) to (2-7):

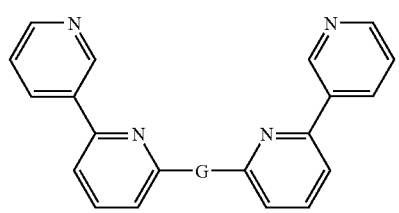
(2-1)

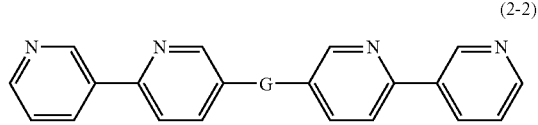
(2-2)

(2-3)
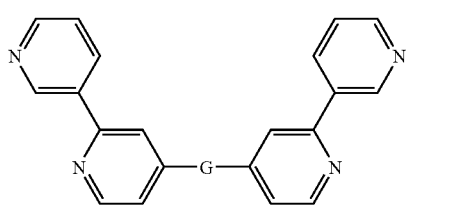

(2-4)
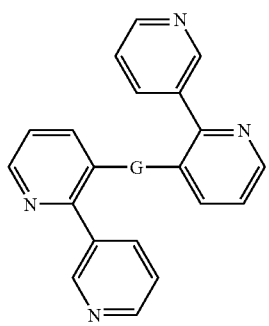

(2-5)
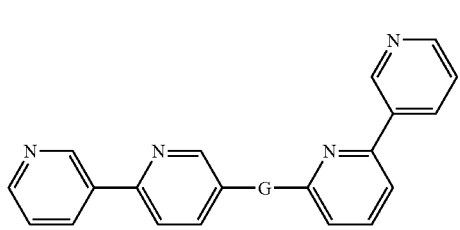

(2-6)
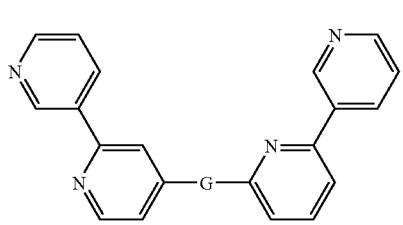

(2-7)
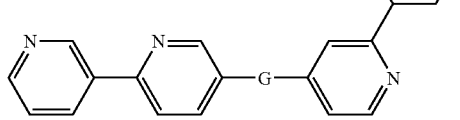

In the Formulas (2-1) to (2-7), a compound represented by Formulas (2-1), (2-2), and (2-3) is preferable, and a compound represented by Formulas (2-1) and (2-2) is more preferable. In the Formulas (2-1) to (2-7), G is most preferably a link represented by Formula (G1), more preferably, a link represented by Formula (G3), preferably, a link represented by Formula (G2).

In Formulas (2-1) to (2-4), when G is a link represented by Formula (G1), $G^1$ is preferably a divalent group derived from one selected from a group consisting of compounds in the above A group, more preferably, a divalent group derived from one selected from a group consisting of compounds represented by (A-1) to (A-10) in the A group, further preferably, one selected from a group consisting of divalent groups represented by (C-1) to (C-15):

(C-1)
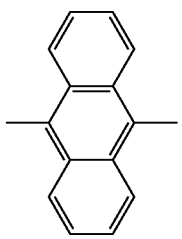

(C-2)
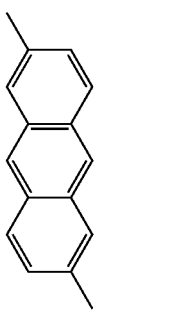

(C-3)
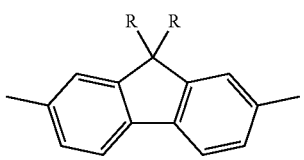

(C-4)
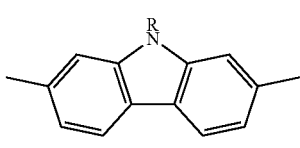

(C-5)
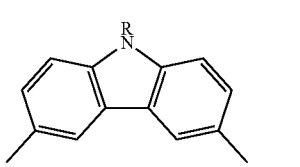

(C-6)
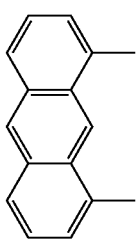

(C-7)
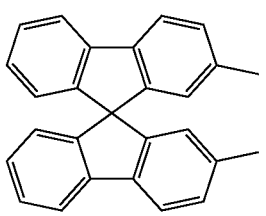

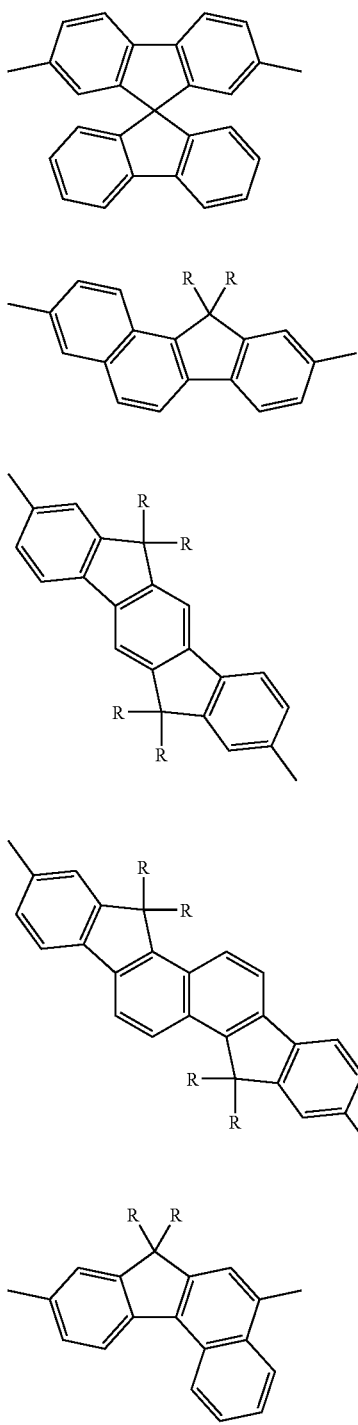

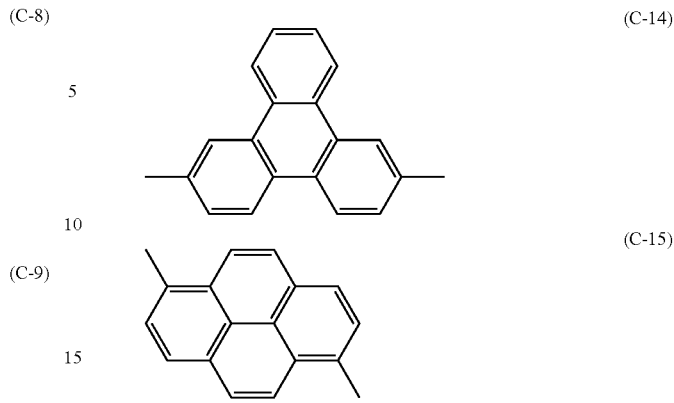

R is independently hydrogen, methyl, ethyl, hexyl, cyclohexyl, phenyl, 1-naphthyl, or 2-naphthyl. A divalent group represented by the Formulas (C-1) to (C-15) may have a substituent on a position other than an atom having a free valency. A specific example of the substituent is phenyl, 2-biphenylyl, 3-biphenylyl, 4-biphenylyl, 1-naphthyl, 2-naphthyl, methyl, t-butyl, or cyclohexyl.

In Formulas (2-1) to (2-4), when G is a link represented by Formula (G2), $G^1$ is preferably a same divalent group derived from one selected from a group consisting of compounds in the A group and the B group as described above, more preferably, a same divalent group derived from one selected from a group consisting of compounds represented by (A-1) to (A-10), further preferably, a same group selected from a group consisting of divalent groups represented by the above (C-1) to (C-15).

In Formulas (2-1) to (2-4), when G is a link represented by Formula (G3), more specifically, G is preferably a link represented by the following Formulas (G3-1) to (G3-3):

$$-G^{1B}-G^{1B}-G^{1B}- \quad (G3\text{-}1)$$

$$-G^{1A}-G^{1B}-G^{1A}- \quad (G3\text{-}2)$$

$$-G^{1B}-G^{1A}-G^{1B}- \quad (G3\text{-}3)$$

$G^{1A}$ is independently a divalent group derived from one selected from a group consisting of compounds in the above A group, and $G^{1B}$ is independently a divalent group derived from one selected from a group consisting of compounds in the above B group.

In Formulas (2-1) to (2-4), when G is a link represented by Formula (G3-1), $G^{1B}$ is preferably a same group selected from a group consisting of divalent groups represented by the following Formulas (D-1) to (D-15):

-continued

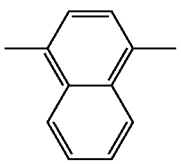 (D-3)

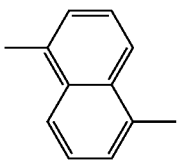 (D-4)

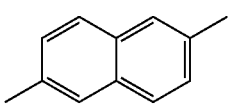 (D-5)

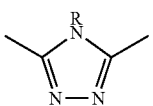 (D-6)

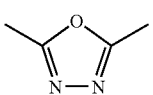 (D-7)

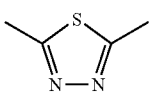 (D-8)

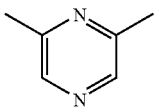 (D-9)

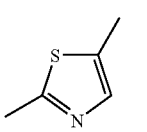 (D-10)

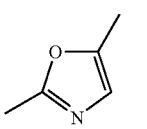 (D-11)

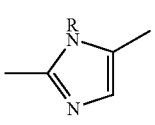 (D-12)

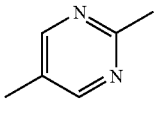 (D-13)

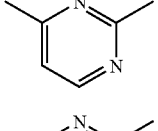 (D-14)

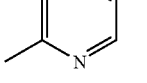 (D-15)

R is independently hydrogen, methyl, ethyl, hexyl, cyclohexyl, phenyl, 1-naphthyl, or 2-naphthyl. A divalent group represented by Formulas (D-1) to (D-15) may have a substituent on a position other than an atom having a free valency. A specific example of the substituent is phenyl, 2-biphenylyl, 3-biphenylyl, 4-biphenylyl, 1-naphthyl, 2-naphthyl, methyl, t-butyl, or cyclohexyl.

In Formulas (2-1) to (2-4), when G is a link represented by Formula (G3-2), $G^{1A}$ is preferably a same group selected from a group consisting of divalent groups represented by the above Formulas (C-1) to (C-5), and $G^{1B}$ is preferably one selected from a group consisting of divalent groups represented by the above Formulas (D-1) to (D-15).

In Formulas (2-1) to (2-4), when G is a link represented by Formula (G3-3), $G^{1A}$ is preferably one selected from a group consisting of divalent groups represented by the above Formulas (C-1) to (C-5), and $G^{1B}$ is preferably a same group selected from a group consisting of divalent groups represented by the above Formulas (D-1) to (D-15).

In Formulas (2-1) to (2-4), when G is a link represented by Formula (G3-1), more specifically, G is more preferably a link represented by Formula (G3-4):

$$G^{1B2}\text{-}G^{1B1}\text{-}G^{1B2}\text{-} \qquad (G3\text{-}4)$$

$G^{1B1}$ is one selected from a group consisting of divalent groups represented by the above Formulas (D-1) to (D-9), and $G^{1B2}$ is a same group selected from a group consisting of divalent groups represented by the above Formulas (D-1) to (D-15).

In Formulas (2-5) to (2-7), G is preferably a link represented by Formula (G1). When G is a link represented by Formula (G1), $G^1$ is preferably a divalent group derived from one selected from a group consisting of compounds in the above A group, more preferably, a divalent group derived from one selected from a group consisting of compounds represented by (A-1) to (A-10) in the above A group, further preferably, one selected from a group consisting of divalent groups represented by the following Formulas (C-1) to (C-15):

(C-1)

(C-2)

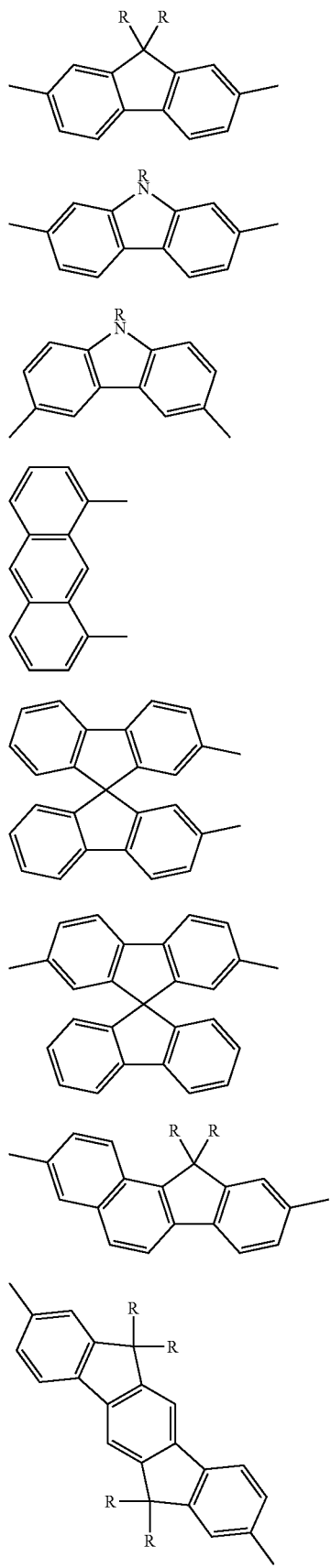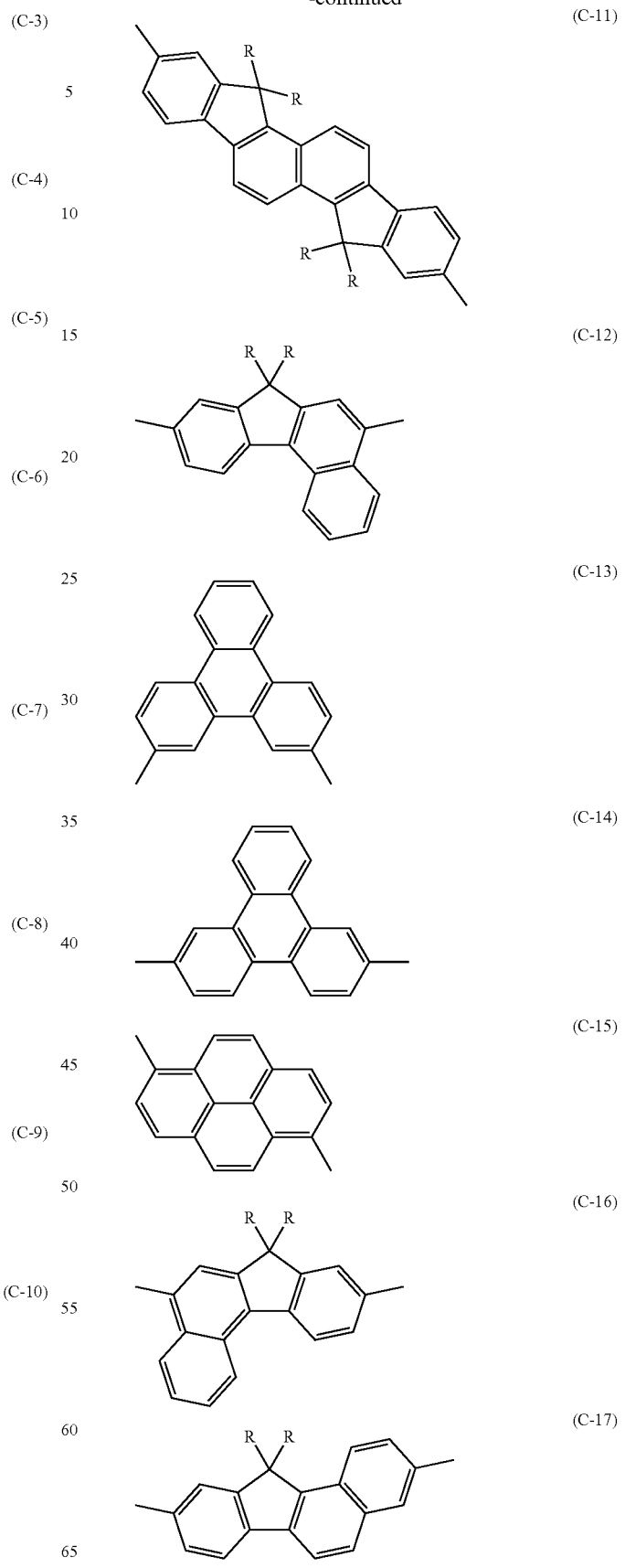

R is independently hydrogen, methyl, ethyl, hexyl, cyclohexyl, phenyl, 1-naphthyl, or 2-naphthyl. A divalent group represented by Formulas (C-1) to (C-17) may have a substituent on a position other than an atom having a free valency. A specific example of the substituent is phenyl, 2-biphenylyl, 3-biphenylyl, 4-biphenylyl, 1-naphthyl, 2-naphthyl, methyl, t-butyl, or cyclohexyl.

<Specific Example of Compound>

A specific example of a compound of the present invention is shown by the Formulas as listed below. However, the present invention is not limited by disclosure of a specific structure of the specific examples below.

<Specific Example of Compound Represented by Formula (2-1)>

A specific example of a compound represented by Formula (2-1) is shown by the following Formulas (2-1-1) to (2-1-39). A preferable compound among the compounds below is shown by Formulas (2-1-1) to (2-1-25), (2-1-40), and (2-1-41). A more preferable compound is shown by Formulas (2-1-1) to (2-1-13), (2-1-40), and (2-1-41). A further preferable compound is shown by Formulas (2-1-1), (2-1-5) to (2-1-8), (2-1-11), (2-1-40), and (2-1-41).

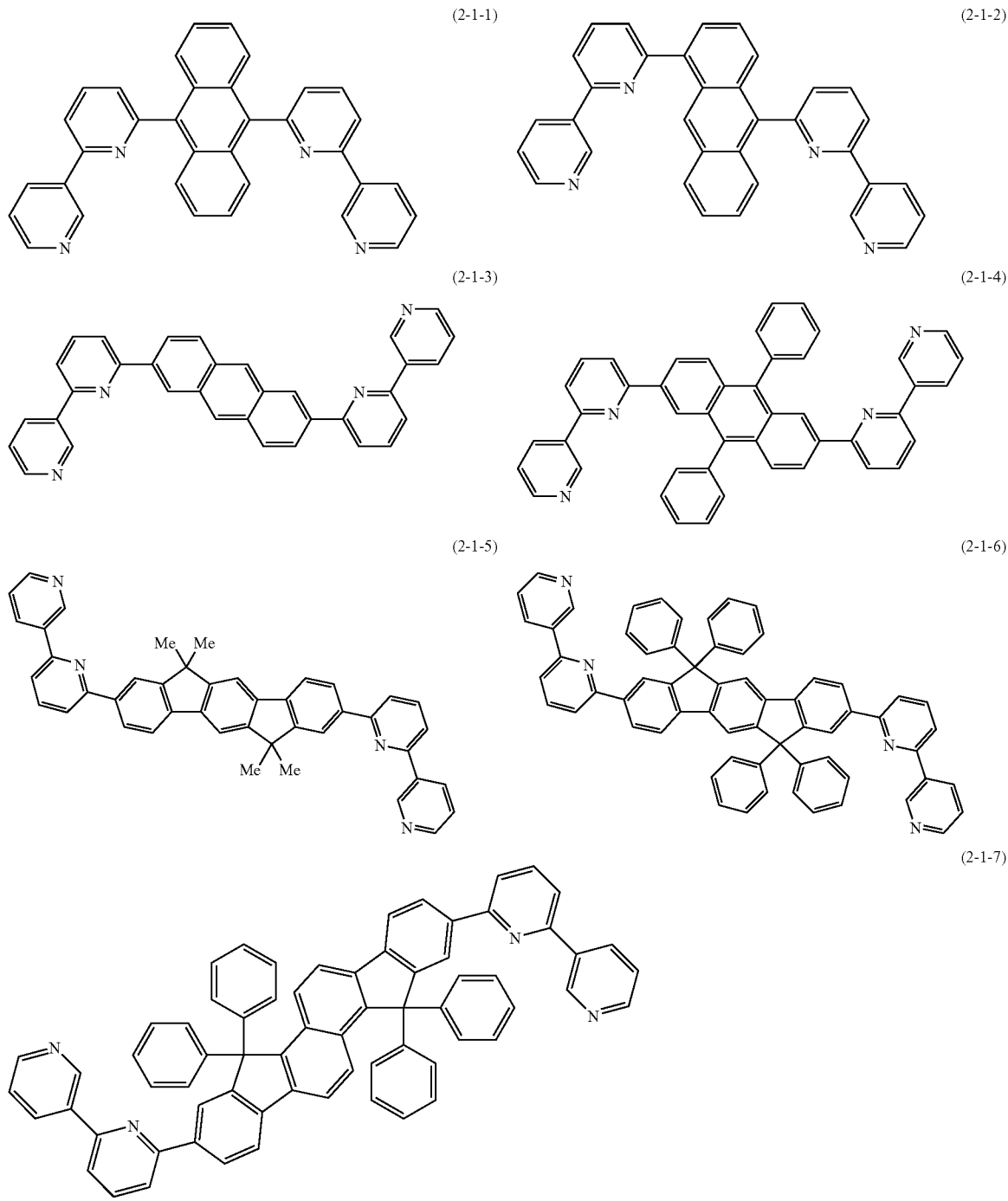

-continued
(2-1-8)
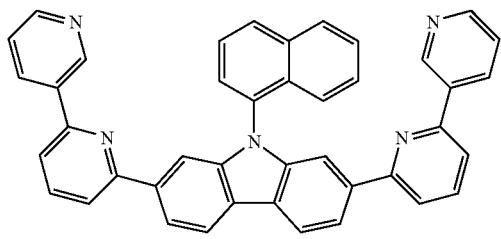
(2-1-9)
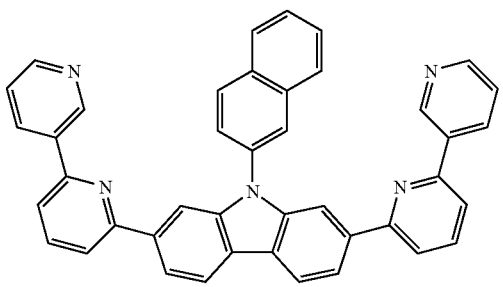
(2-1-10)
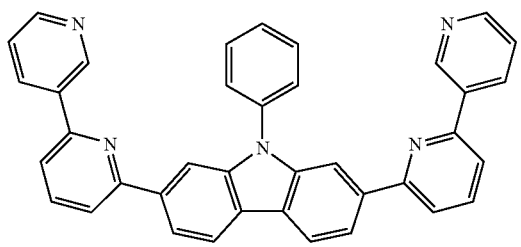
(2-1-11)
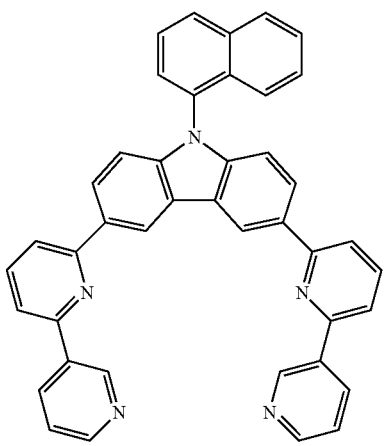
(2-1-12)
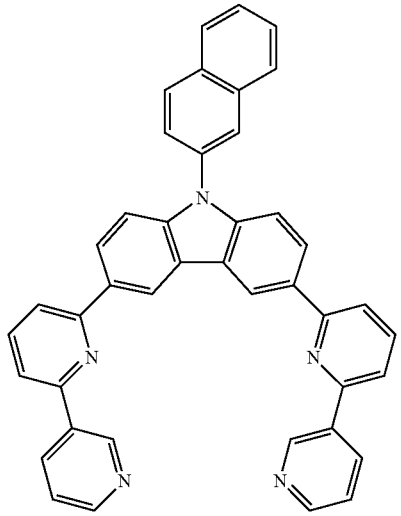
(2-1-13)
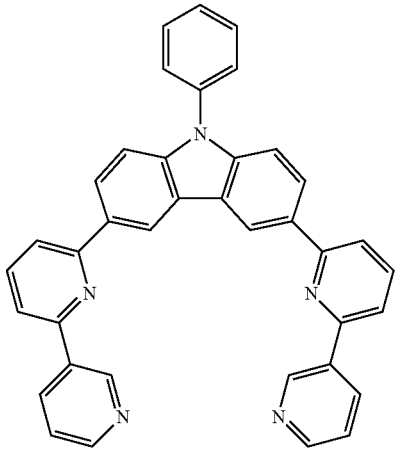
(2-1-14)
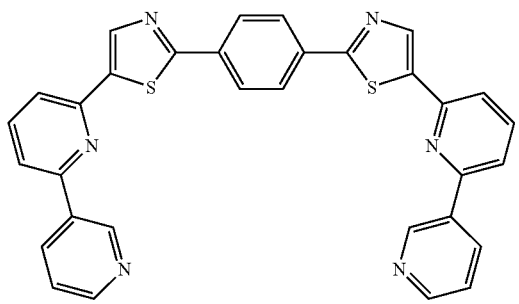
(2-1-15)
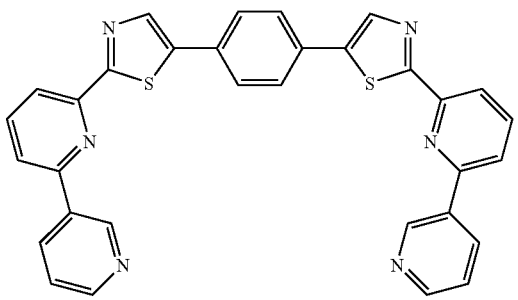

-continued
(2-1-16)
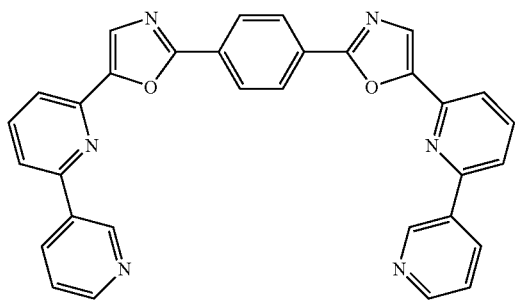
(2-1-17)
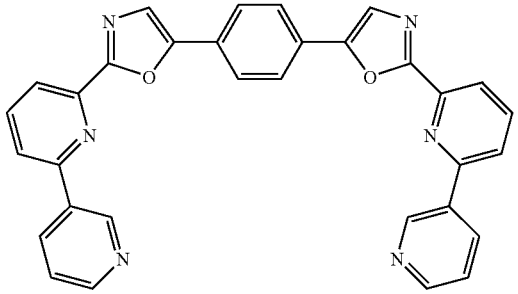
(2-1-18)
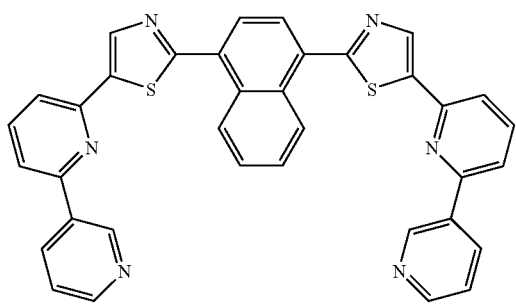
(2-1-19)
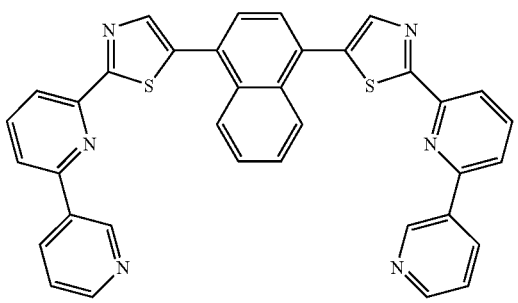
(2-1-20)
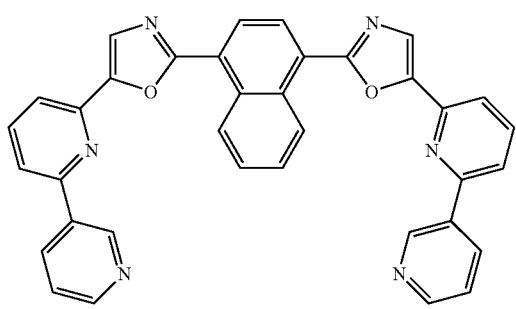
(2-1-21)
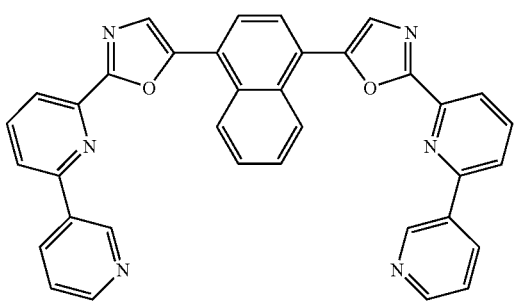
(2-1-22)
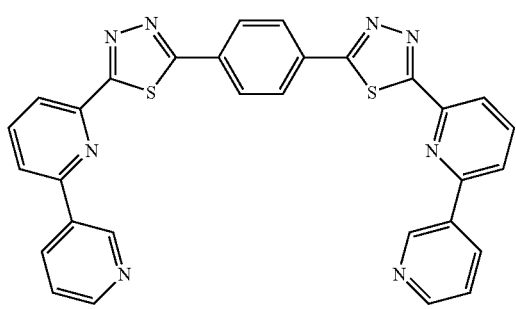
(2-1-23)
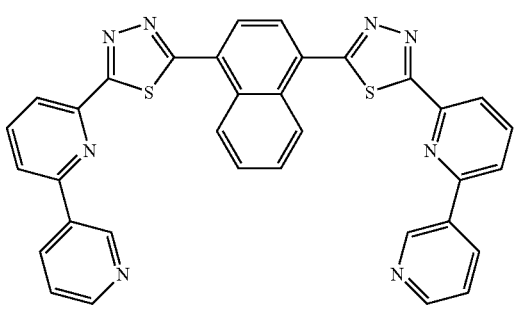
(2-1-24)
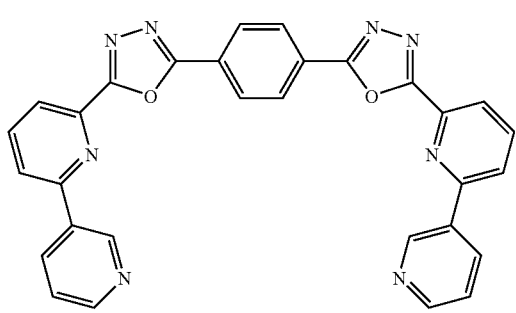
(2-1-25)
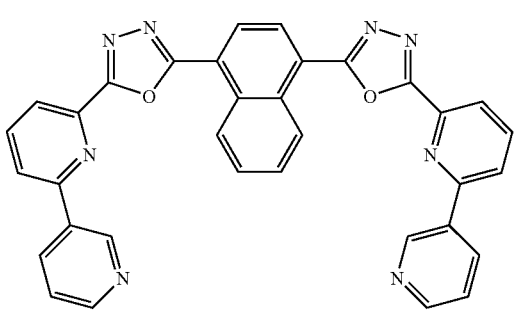

-continued
(2-1-26)
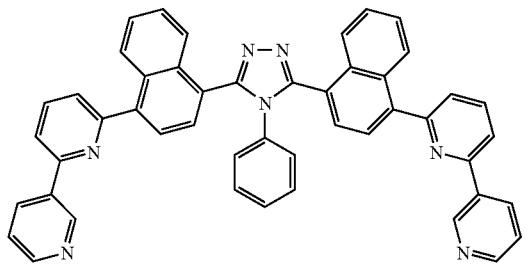
(2-1-27)
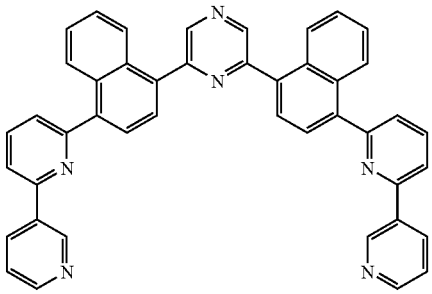
(2-1-28)
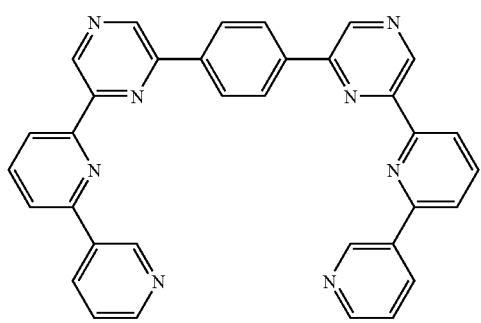
(2-1-29)
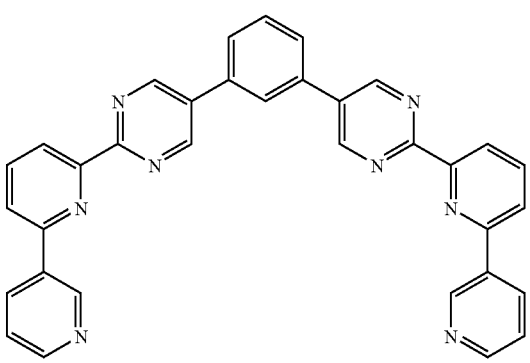
(2-1-30)
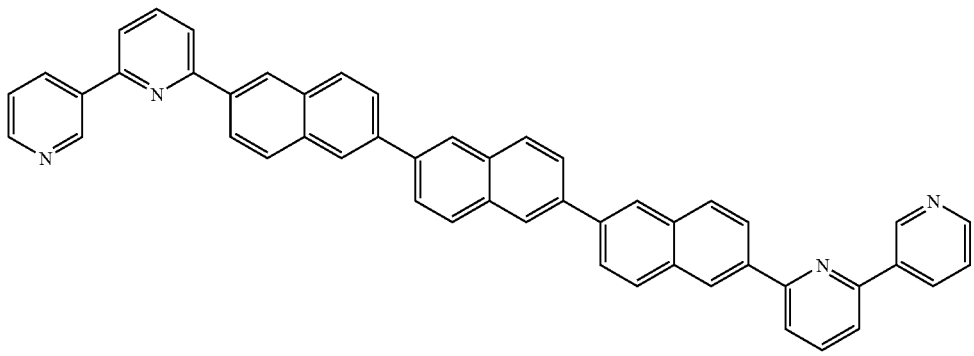
(2-1-31)
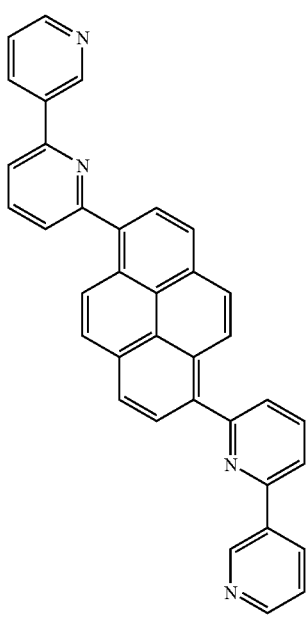

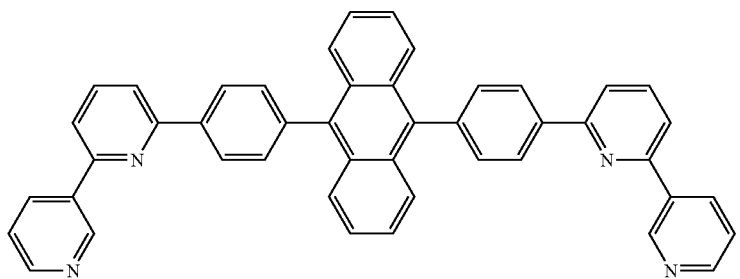
(2-1-32)
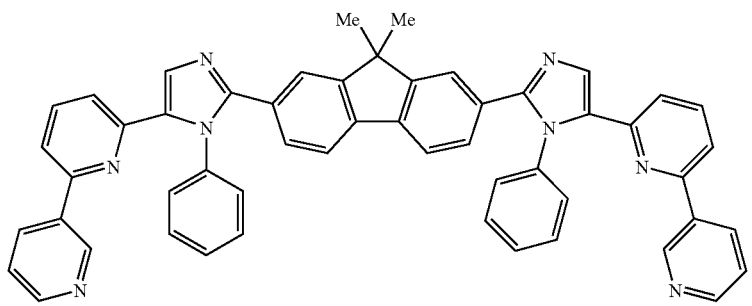
(2-1-33)
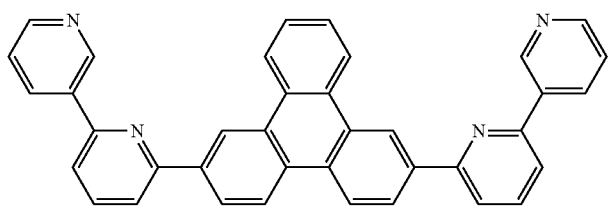
(2-1-34)
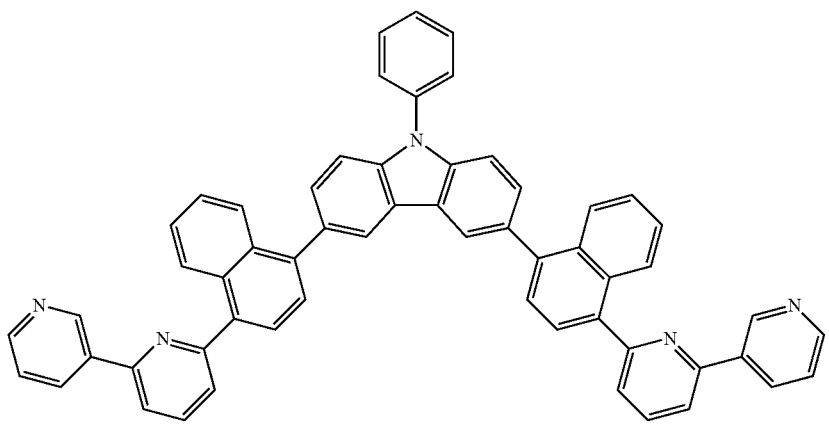
(2-1-35)
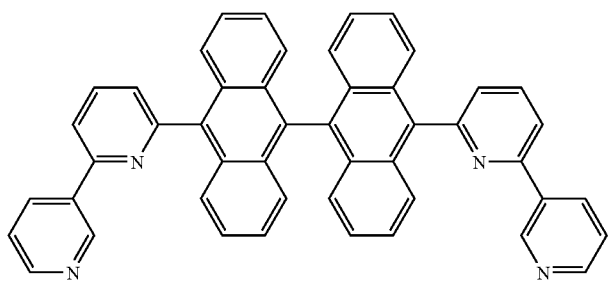
(2-1-36)

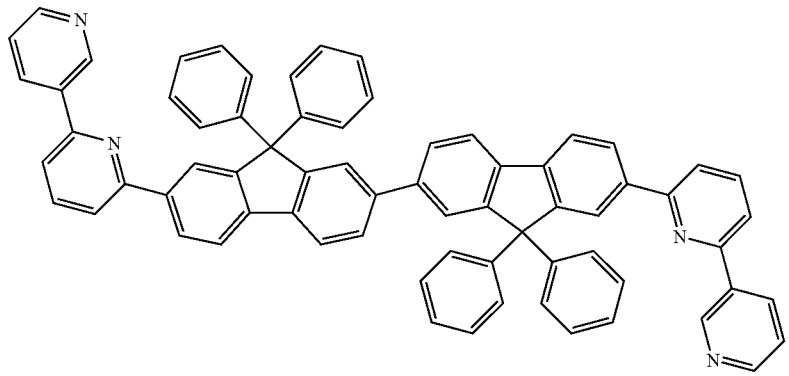
(2-1-37)
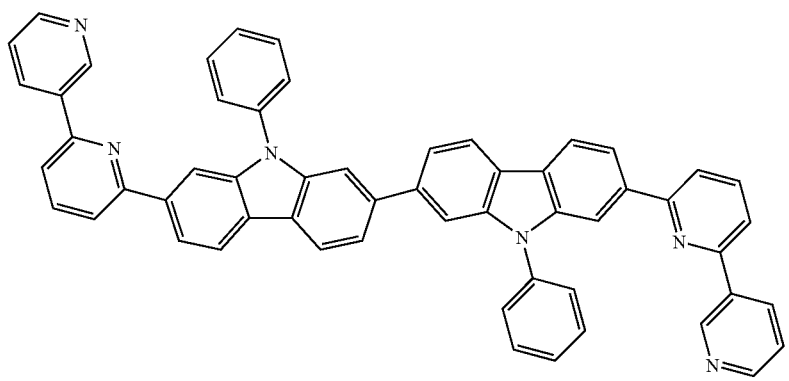
(2-1-38)
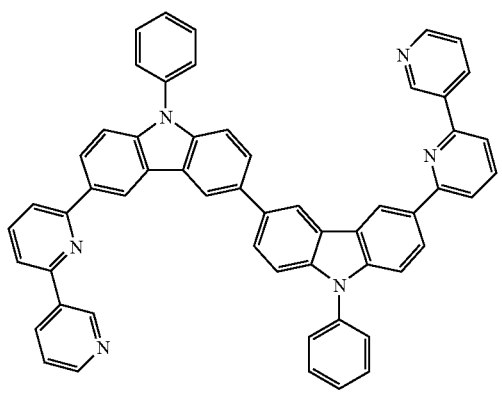
(2-1-39)
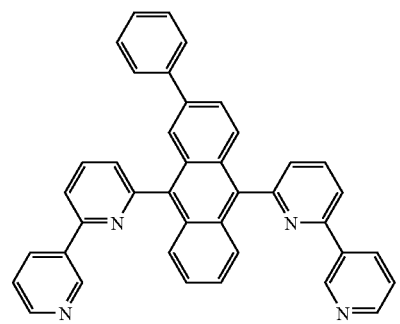
(2-1-40)
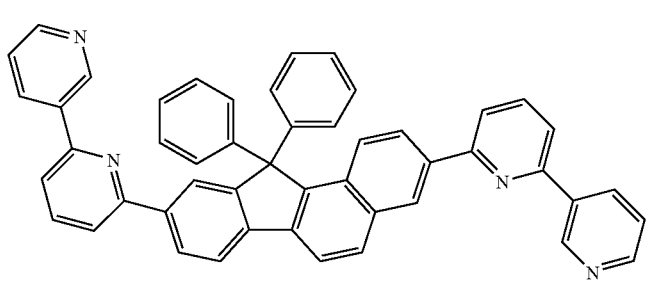
(2-1-41)

<Specific Example of Compound Represented by Formula (2-2)>
A specific example of a compound represented by Formula (2-2) is shown by the following Formulas (2-2-1) to (2-2-28).
A preferable compound among the compounds below is shown by Formulas (2-2-1) to (2-2-11), (2-2-22), (2-2-25) to (2-2-27), (2-2-29), and (2-2-30). A more preferable compound is shown by Formulas (2-2-1) to (2-2-3), (2-2-5), (2-2-6), (2-2-9), (2-2-29), and (2-2-30).
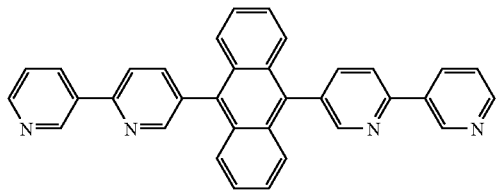
(2-2-1)
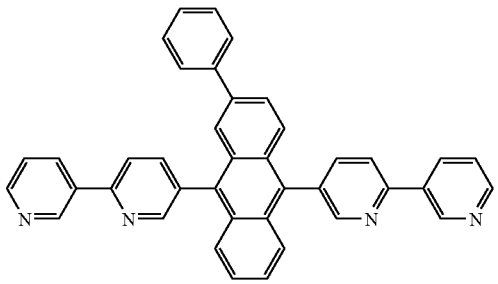
(2-2-2)
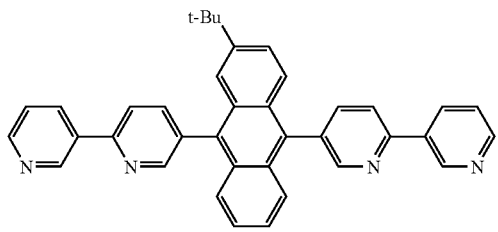
(2-2-3)
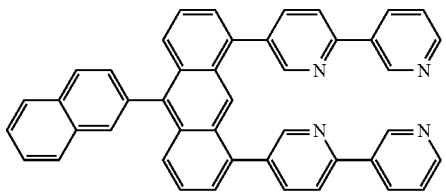
(2-2-4)
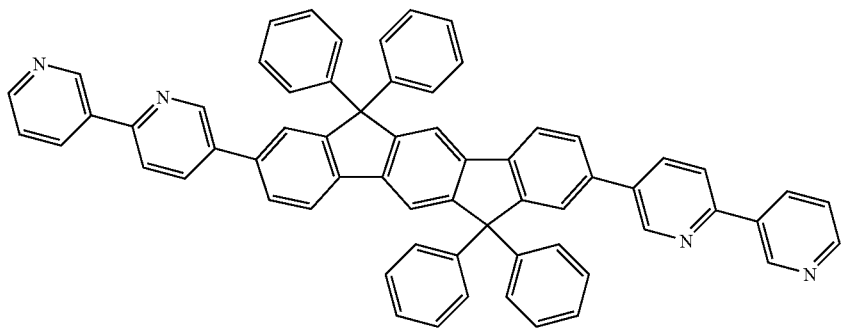
(2-2-5)
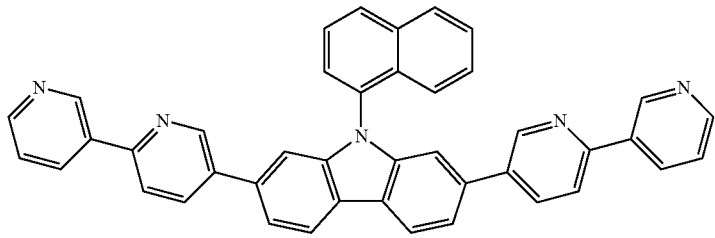
(2-2-6)
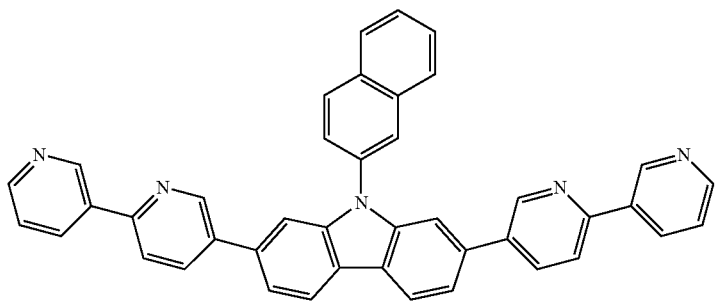
(2-2-7)

(2-2-8)
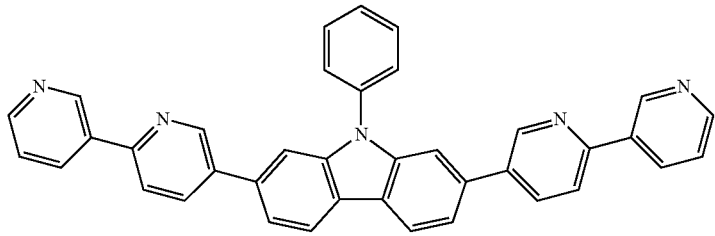
(2-2-9) (2-2-10)
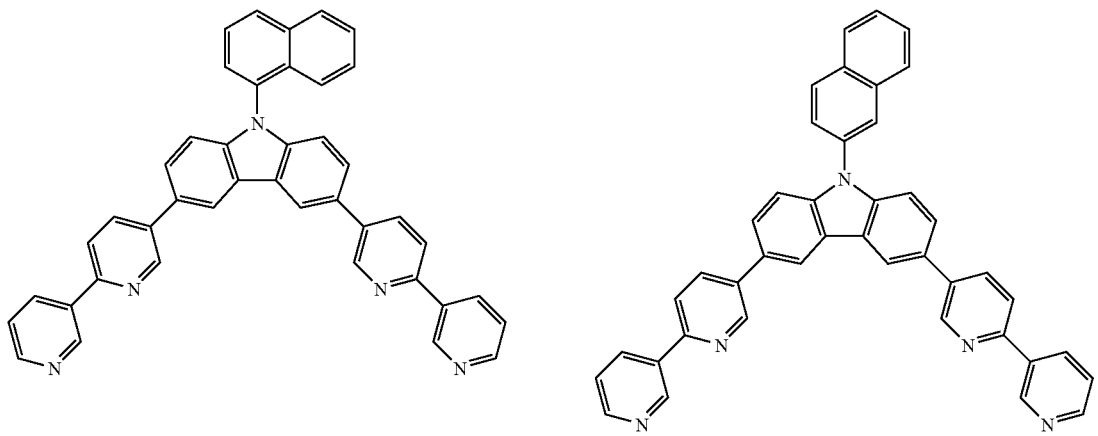
(2-2-11) (2-2-12)
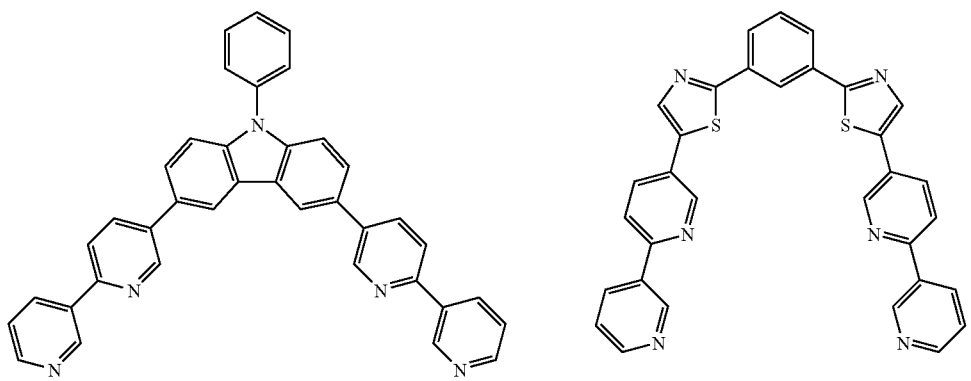
(2-2-13) (2-2-14)
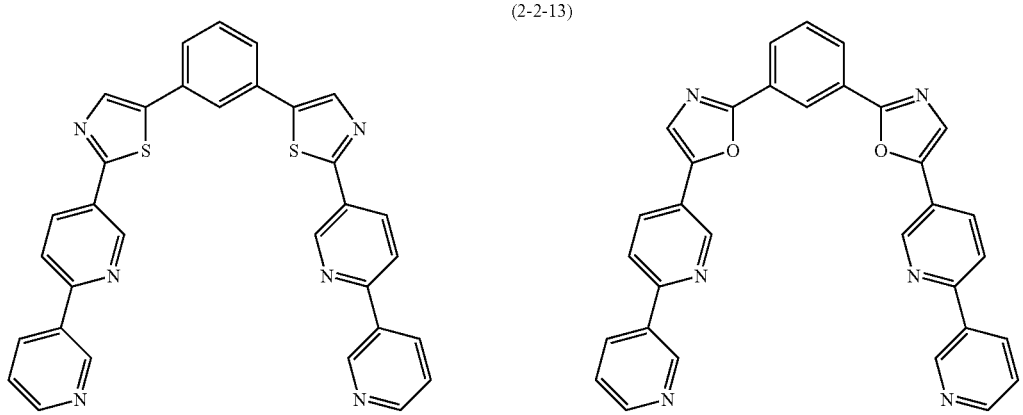

-continued
(2-2-15)
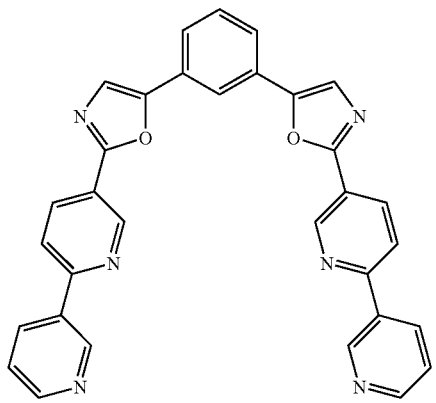
(2-2-16)
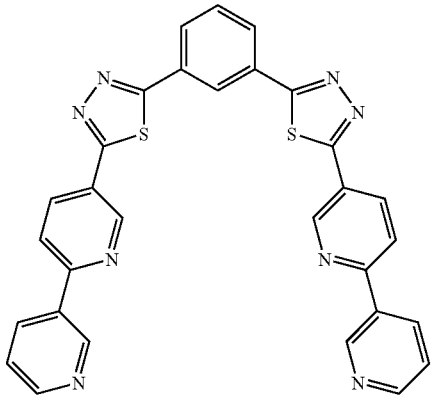
(2-2-17)
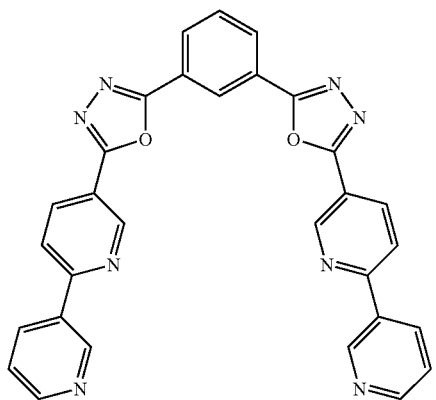
(2-2-18)
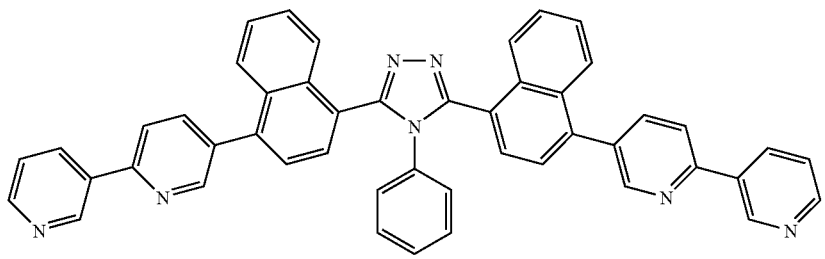
(2-2-19)
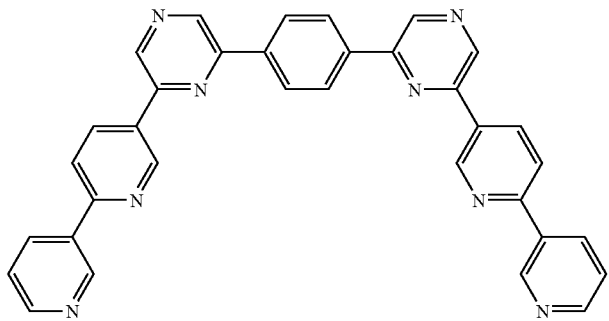

(2-2-20)
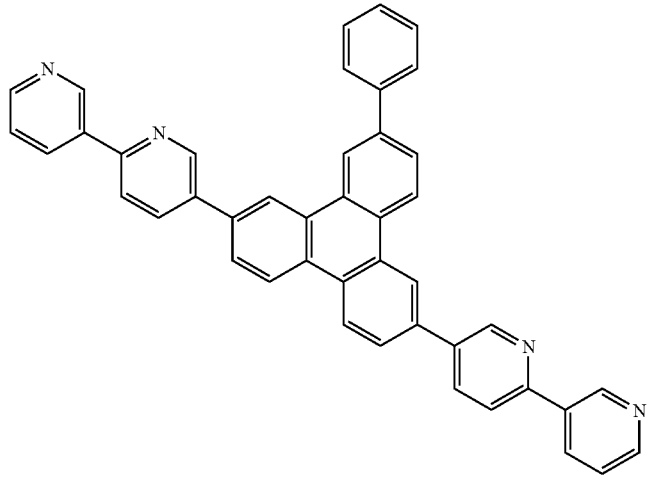
(2-2-21)
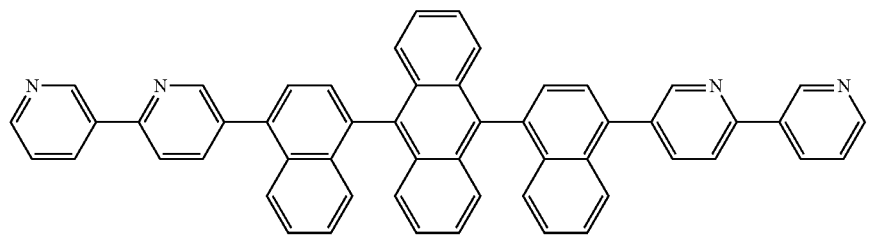
(2-2-22)
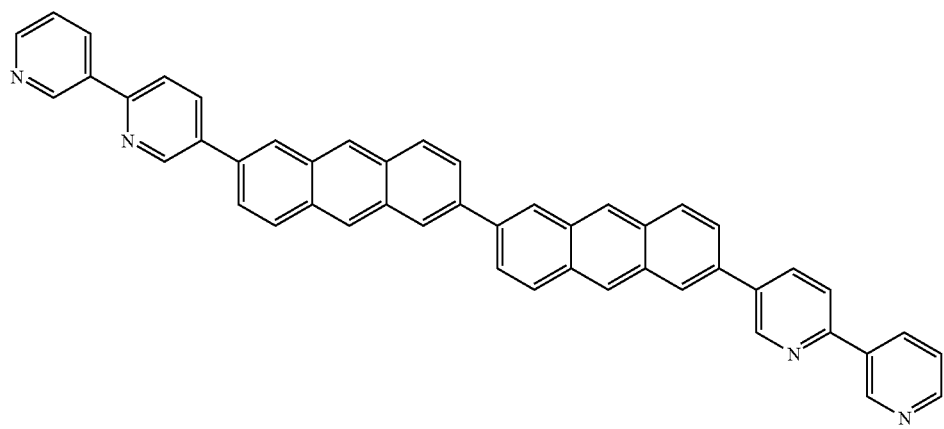
(2-2-23)
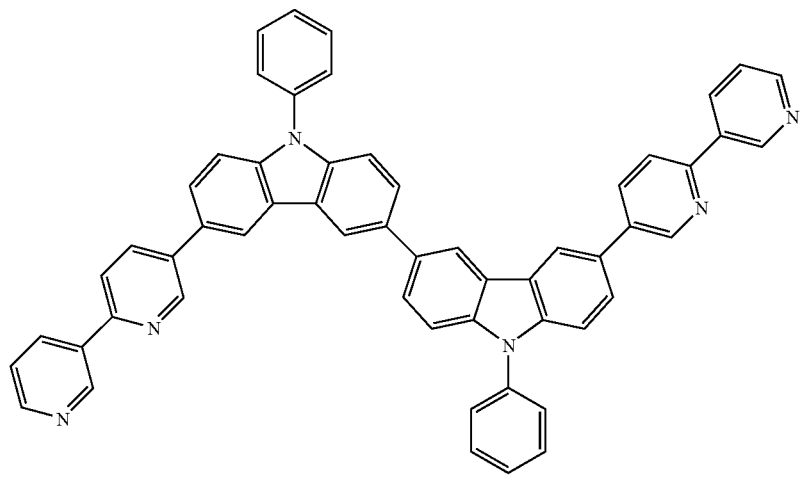

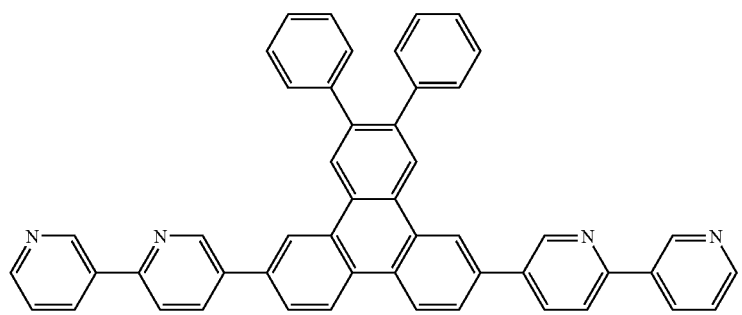
(2-2-24)
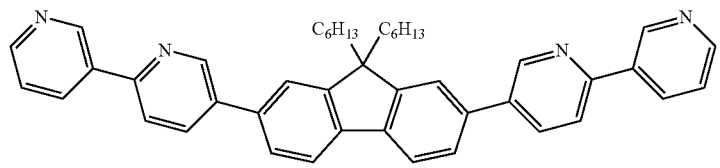
(2-2-25)
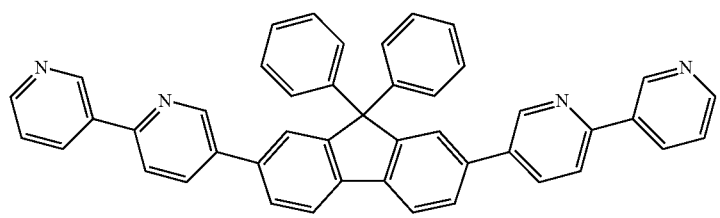
(2-2-26)
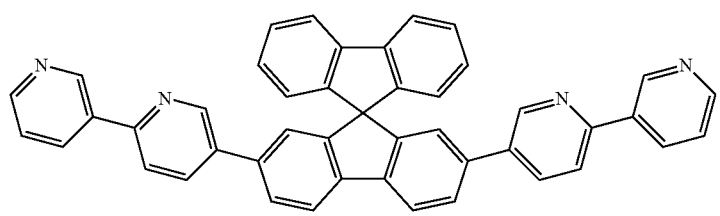
(2-2-27)
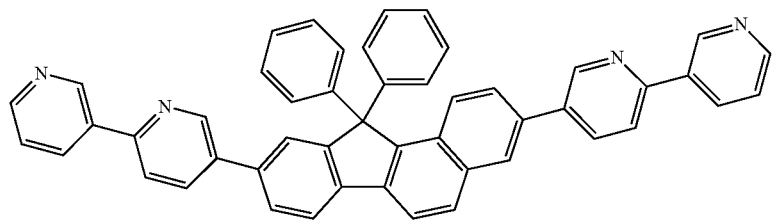
(2-2-28)
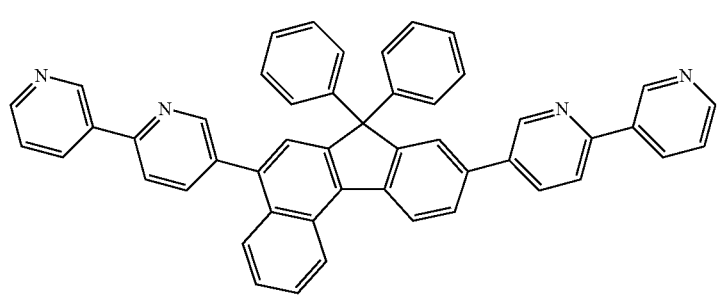
(2-2-29)
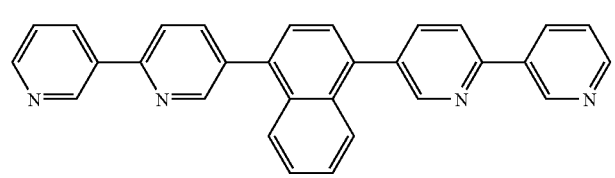
(2-2-30)

<Specific Example of Compound Represented by Formula (2-3)>
A specific example of a compound represented by Formula (2-3) is shown by the following Formulas (2-3-1) to (2-3-14).
(2-3-1)
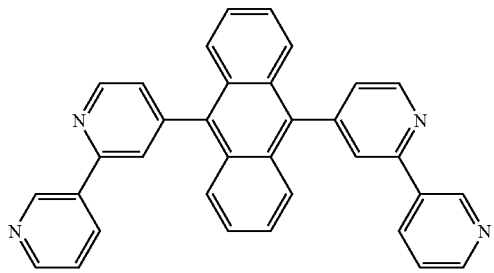
(2-3-2)
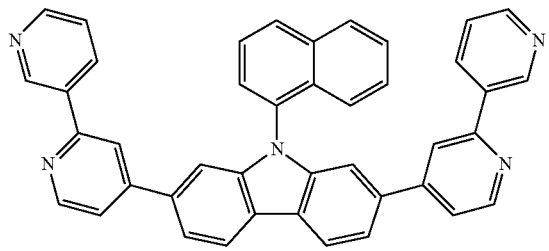
(2-3-3)
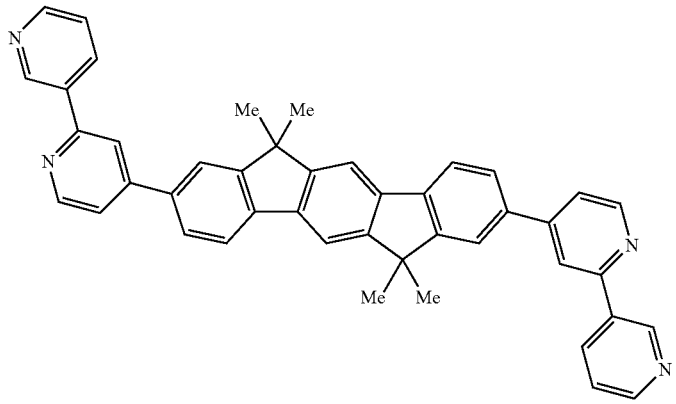
(2-3-4)
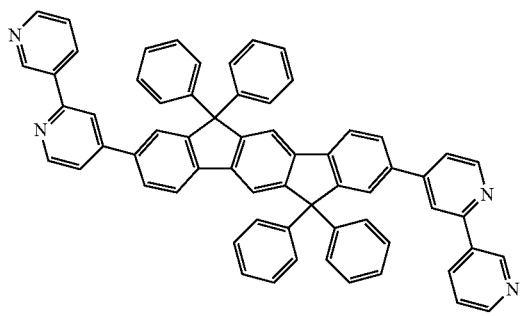
(2-3-5)
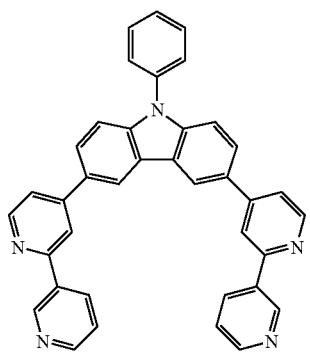
(2-3-6)
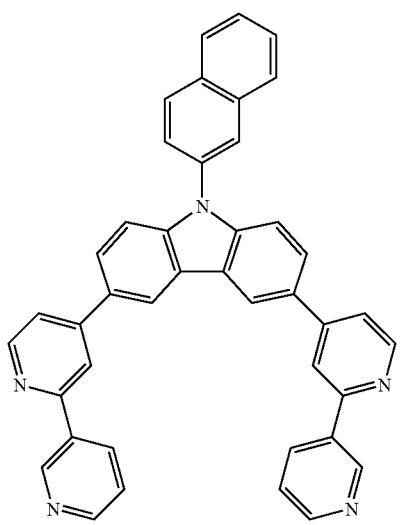
(2-3-7)
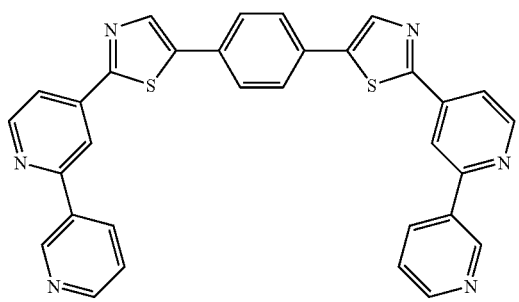

-continued
(2-3-8)
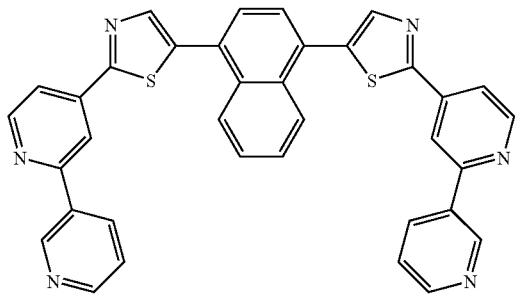
(2-3-9)
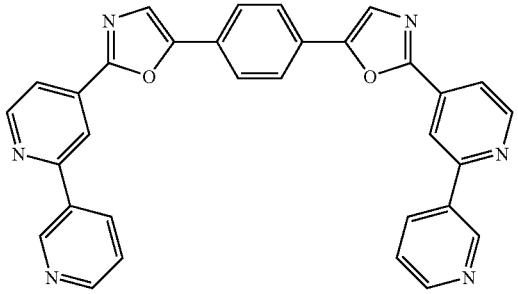
(2-3-10)
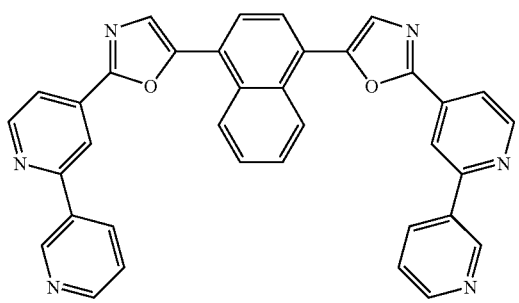
(2-3-11)
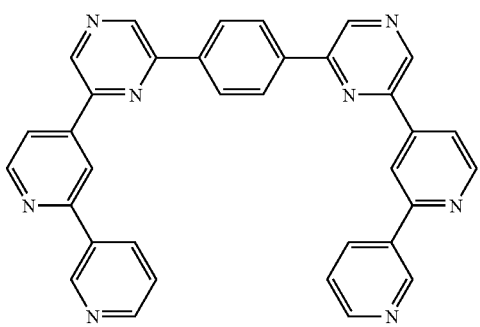
(2-3-12)
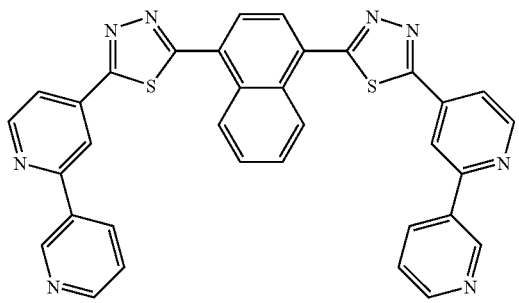
(2-3-13)
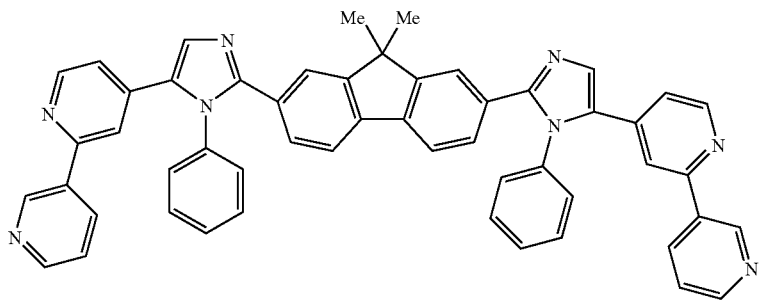
(2-3-14)
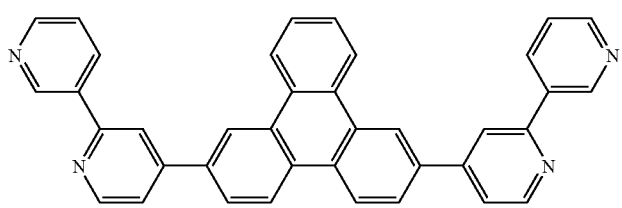

<Specific Example of Compound Represented by Formula (2-4)>
A specific example of a compound represented by Formula (2-4) is shown by the following Formulas (2-4-1) to (2-4-5):
(2-4-1)
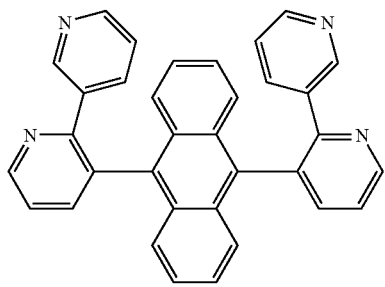
(2-4-2)
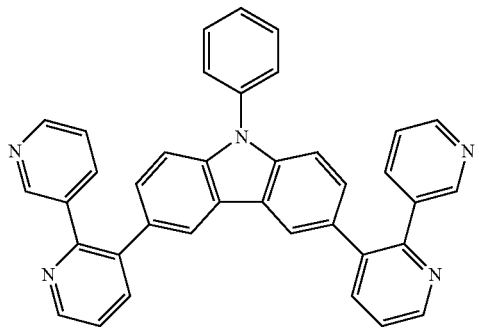
(2-4-3)
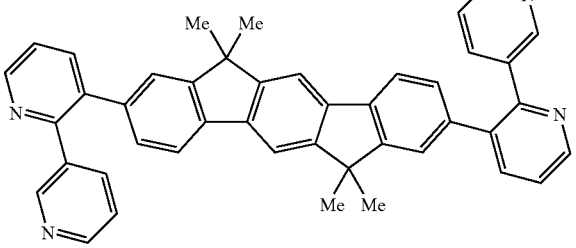
(2-4-4)
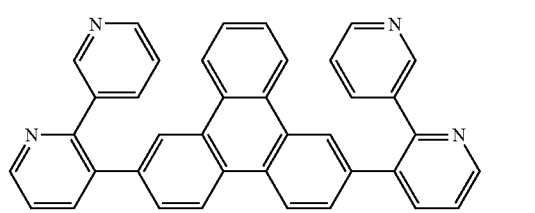
(2-4-5)
<Specific Example of Compound Represented by Formula (2-5)>
A specific example of a compound represented by Formula (2-5) is shown by the following Formulas (2-5-1) to (2-5-5):
(2-5-1)
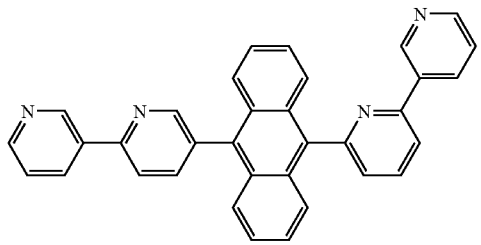
(2-5-2)
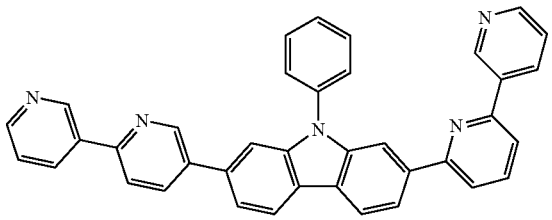
(2-5-3)
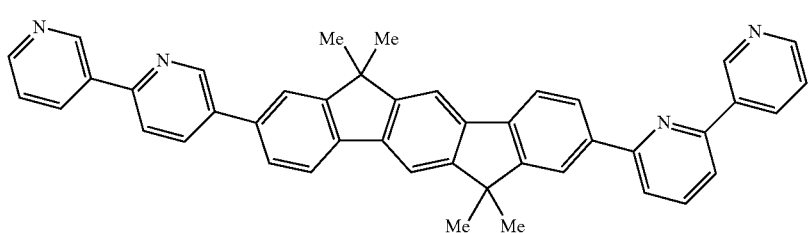

(2-5-4) 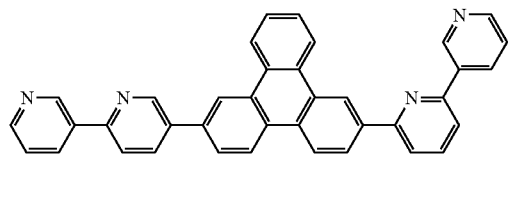
(2-5-5) 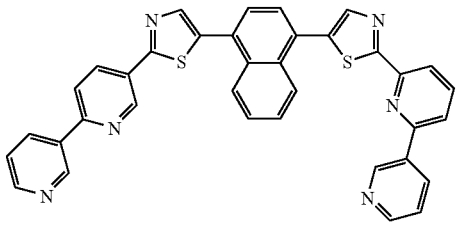
<Specific Example of Compound Represented by Formula (2-6)>
A specific example of a compound represented by Formula (2-6) is shown by the following Formulas (2-6-1) to (2-6-5):
(2-6-1) 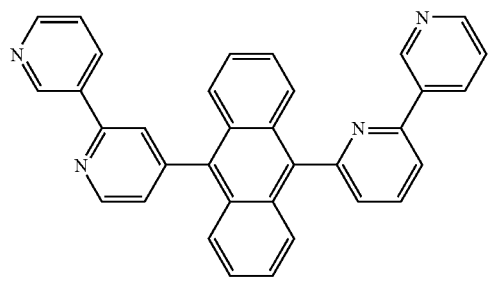
(2-6-2) 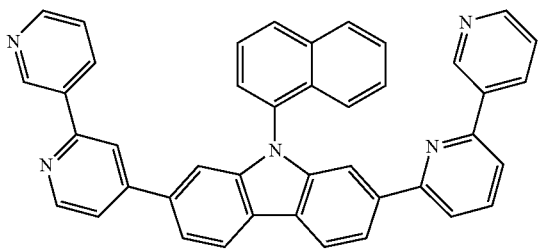
(2-6-3) 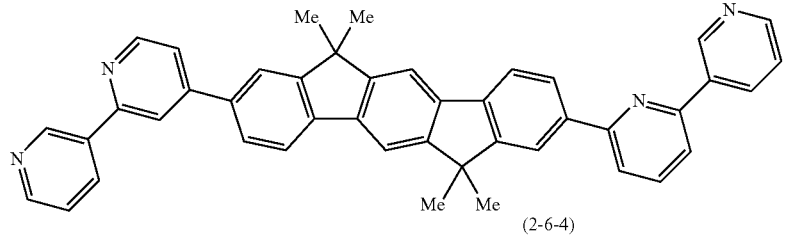
(2-6-4) 
(2-6-5) 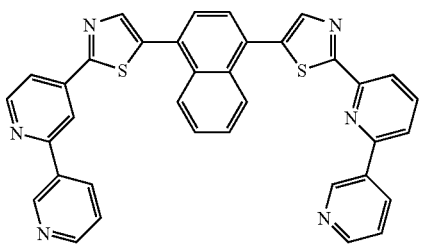
<Specific Example of Compound Represented by Formula (2-7)>
A specific example of a compound represented by Formula (2-7) is shown by the following Formulas (2-7-1) to (2-7-5):
(2-7-1) 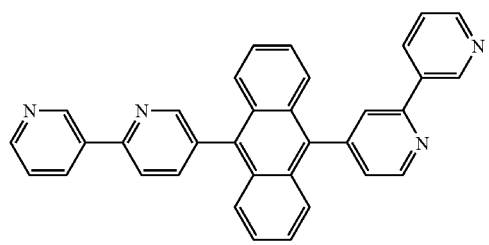
(2-7-2) 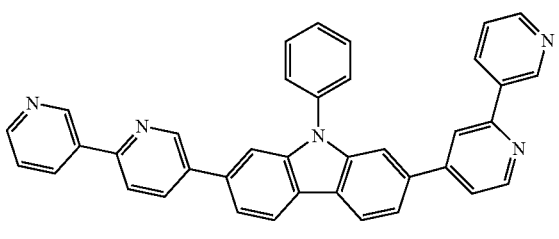

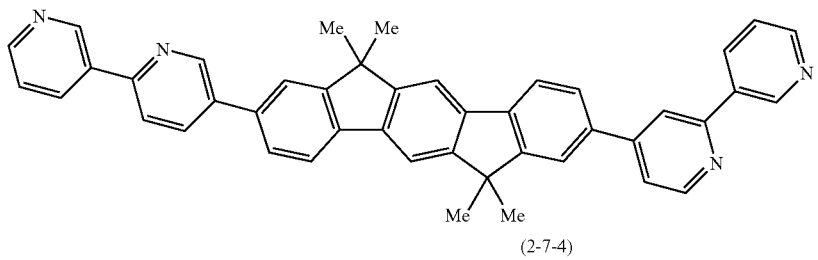
(2-7-3)
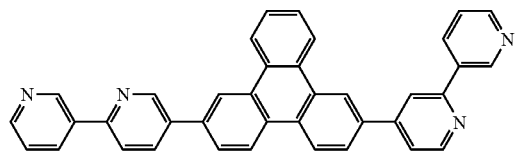
(2-7-4)
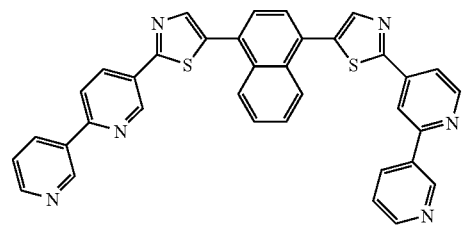
(2-7-5)
<Specific Example of Compound Represented by Formula (3)>
A specific example of a compound represented by Formula (3) is shown by the following Formulas (3-1) to (3-6):
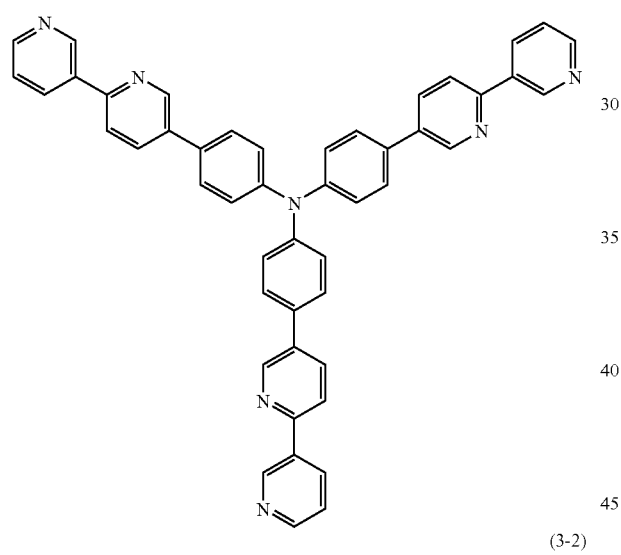
(3-1)
(3-2)
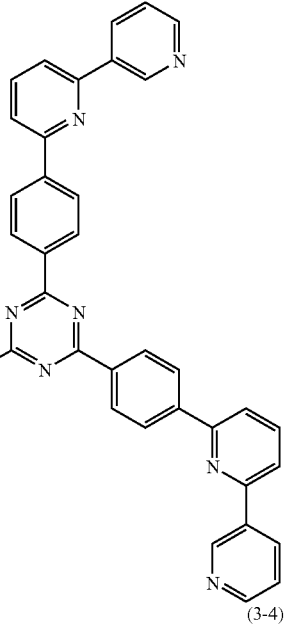
-continued
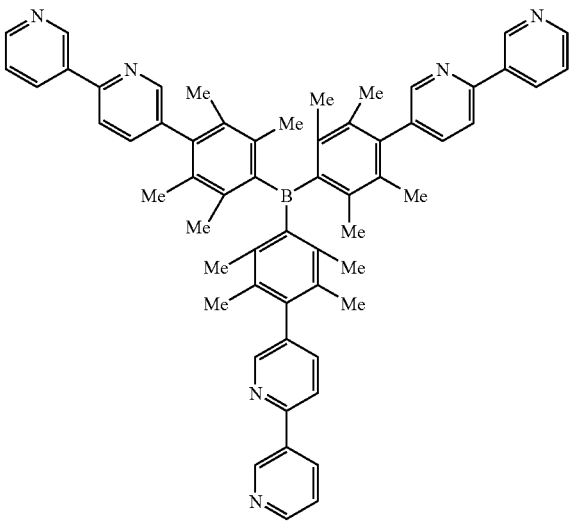
(3-3)
(3-4)

-continued (3-5)

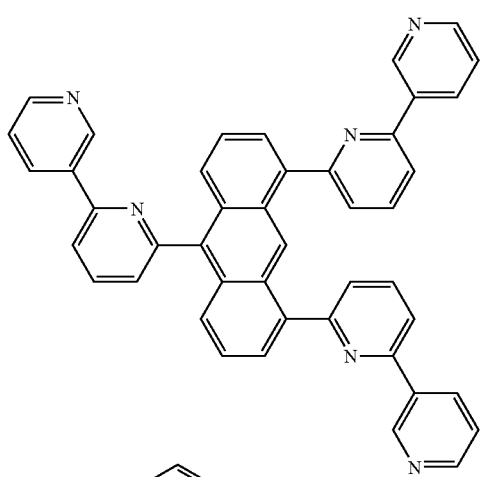

(3-6)

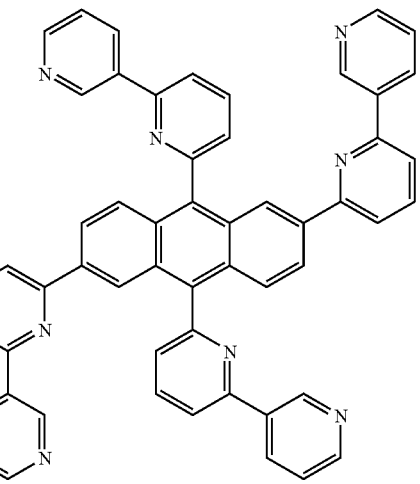

-continued (4-2)

(4-3)

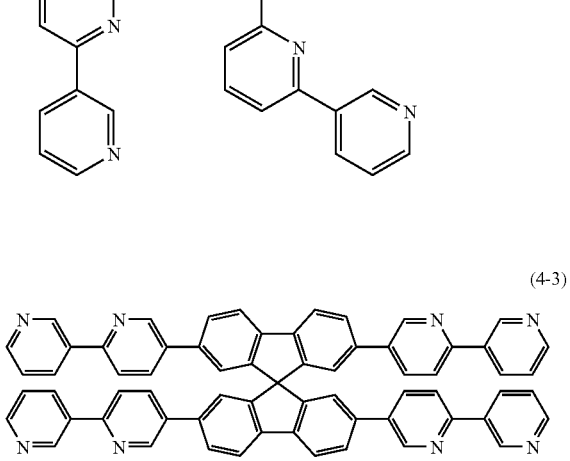

(4-4)

A specific example of a compound represented by Formula (4) is shown by the following Formulas (4-1) to (4-4):

(4-1)

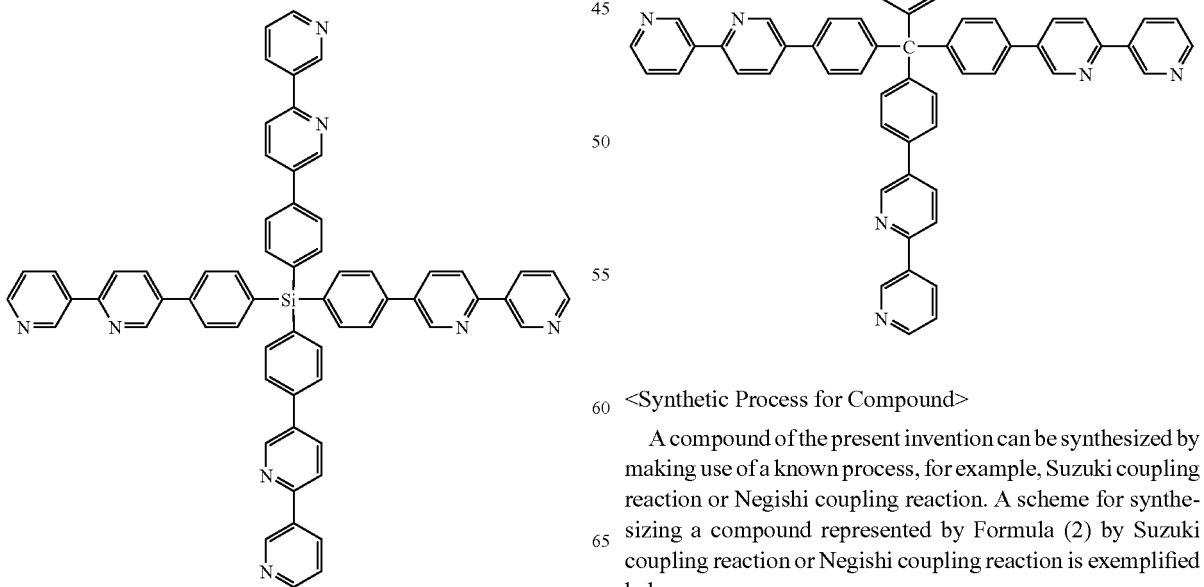

<Synthetic Process for Compound>

A compound of the present invention can be synthesized by making use of a known process, for example, Suzuki coupling reaction or Negishi coupling reaction. A scheme for synthesizing a compound represented by Formula (2) by Suzuki coupling reaction or Negishi coupling reaction is exemplified below.

Scheme 1: Suzuki coupling

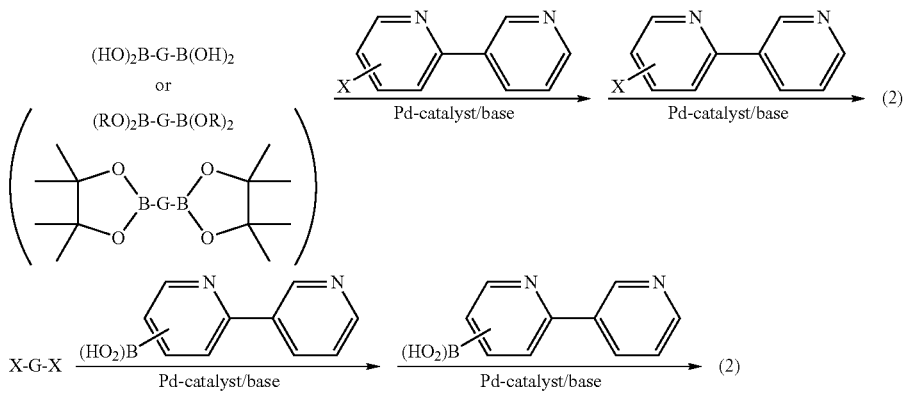

wherein G is a divalent group or a ring having two free valencies, and X is chlorine, bromine, iodine, or triflate (trifluoromethanesulfonate).

Scheme 2: Negishi coupling

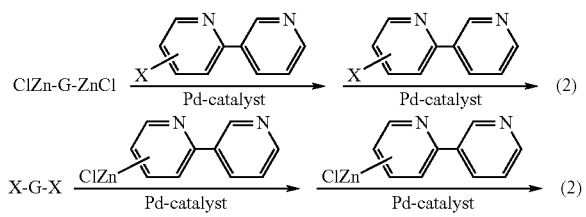

wherein G is a divalent group or a ring having two free valencies, and X is chlorine, bromine, iodine, or triflate (trifluoromethanesulfonate).

Scheme 1 shows a process of allowing 2,3'-bipyridine having a reactive group to react with G in which two places are converted to boronic acid or boronate in two steps under the presence of a palladium catalyst and a base, and a process of allowing boronic acid of 2,3'-bipyridine to react with G having reactive groups in two places in two steps under the presence of a palladium catalyst and a base. When a same group of 2,3'-bipyridyl is introduced into G, 2,3'-bipyridine having a reactive group at a molar ratio of two times as large as G may be allowed to react at one time in the upper process, and boronic acid of 2,3'-bipyridine at a molar ratio of two times as large as G may be allowed to react at one time in the lower process.

Scheme 2 shows a process of allowing 2,3'-bipyridine having a reactive group to react with G in which two places are converted to a zinc complex in two steps under the presence of a palladium catalyst, and a process of allowing a zinc complex of 2,3'-bipyridine to react with G having reactive groups in two places in two steps under the presence of a palladium catalyst. When a same group of 2,3'-bipyridyl is introduced into G, 2,3'-bipyridine having a reactive group at a molar ratio of two times as large as G may be allowed to react at one time in the upper process, and a zinc complex of 2,3'-bipyridine at a molar ratio of two times as large as G may be allowed to react at one time in the lower process.

When G is a link in which plural divalent groups are linked, or plural rings having two free valencies are linked, or a divalent group and a ring having two free valencies are combined, for example, when a link is represented by Formula -$G^1$-$G^1$-, a 2,3'-bipyridyl group may be linked to $G^1$ as a simple substance by using the above coupling reaction, respectively, and then an intended compound may be synthesized by linking $G^1$ with each other by a known coupling reaction. Even during the above coupling reaction, Suzuki coupling reaction or Negishi coupling reaction is preferably used.

Moreover, when $G^1$ is a heteroring such as oxadiazole, such a process can be also used as synthesizing through an intramolecular cyclization dehydration reaction of hydrazide obtained by allowing hydrazine to react with acid chloride of a ring having a 2,3'-bipyridyl group for both of $G^1$.

A compound represented by Formula (3) or Formula (4) can be also synthesized by combining the above synthetic process suitably. As described above, a synthetic process of a compound of the present invention is exemplified. However, the present invention is not limited by the above exemplified synthetic processes.

A specific example of a palladium catalyst used in Suzuki coupling reaction is $Pd(PPh_3)_4$, $PdCl_2(PPh_3)_2$, $Pd(OAc)_2$, tris(dibenzylideneacetone)dipalladium(0), or tris(dibenzylieneacetone)dipalladium(0) chloroform complex. A phosphine compound may be added, if necessary, to the above palladium compounds in order to accelerate the reaction. A specific example of the phosphine compound is tri(t-butyl)phosphine, tricyclohexyl phosphine, 1-(N,N-dimethylaminomethyl)-2-(di-t-butylphosphino)ferrocene, 1-(N,N-dibutylaminomethyl)-2-(di-t-butylphosphino)ferrocene, 1-(methoxymethyl)-2-(di-t-butylphosphino)ferrocene, 1,1'-bis(di-t-butylphosphino)ferrocene, 2,2'-bis(di-t-butylphosphino)-1,1'-binaphtyl, 2-methoxy-2'-(di-t-butylphosphino)-1,1'-binaphtyl, or 2-dicyclohexylphosphino-2',6'-dimethoxybiphenyl. A specific example of a base used in the above reaction is sodium carbonate, potassium carbonate, cesium carbonate, sodium bicarbonate, sodium hydroxide, potassium hydroxide, barium hydroxide, sodium ethoxide, sodium t-butoxide, sodium acetate, tripotassium phosphate, or potassium fluoride. Furthermore, a specific example of a solvent used in the above reaction is benzene, toluene, xylene, N,N-dimethylformamide, tetrahydrofuran, diethyl ether, t-butylmethyl ether, 1,4-dioxane, methanol, ethanol, or isopropyl alcohol. The solvent can be selected suitably, and may be used alone or as a mixed solvent.

A specific example of a palladium catalyst used in Negishi coupling reaction is $Pd(PPh_3)_4$, $PdCl_2(PPh_3)_2$, $Pd(OAc)_2$, tris(dibenzylideneacetone)dipalladium(0), tris(dibenzylideneacetone)dipalladium(0) chloroform complex, bis(tri-t-butylphosphino)palladium(0), or (1,1'-bis(diphenylphosphino) ferrocene)dichloropalladium(II). Furthermore, a specific example of a solvent used in the reaction is benzene, toluene, xylene, N,N-dimethylformamide, tetrahydrofuran, diethyl ether, t-butylmethyl ether, or 1,4-dioxane. The solvent can be selected suitably, and may be used alone or as a mixed solvent.

When a compound of the present invention is used for an electron injection layer or an electron transport layer in an organic EL device, the organic EL device is stable during applying an electric field, moreover, emission can be obtained at low voltage. The above performances represent that the compound of the present invention is excellent as an electron injection material or an electron transport material of an electroluminescent type device. The electron injection layer referred to in this case means a layer for receiving an electron from a cathode to an organic layer, and the electron transport layer means a layer for transporting an injected electron to an emission layer. Moreover, the electron transport layer can simultaneously serve as the electron injection layer. A material used for each layer is referred to as the electron injection material and the electron transport material, respectively.

<Explanation of Organic EL Device>

The second present invention refers to an organic EL device comprising a compound represented by Formula (1) of the present invention in an electron injection layer or an electron transport layer. The organic EL device of the present invention has low drive voltage and high durability during driving.

An organic EL device of the present invention has structures of various modes. Fundamentally, the device comprises a multilayer structure in which at least a hole transport layer, an emission layer, and an electron transport layer are sandwiched between an anode and a cathode. An example of a specific constitution of a device is (1) anode/hole transport layer/emission layer/electron transport layer/cathode, (2) anode/hole injection layer/hole transport layer/emission layer/electron transport layer/cathode, or (3) anode/hole injection layer/hole transport layer/emission layer/electron transport layer/electron injection layer/cathode.

A compound of the present invention has high electron injection ability and high electron transport ability, and therefore the compound can be used for an electron injection layer or an electron transport layer as a simple substance or in combination with another material. According to an organic EL device of the invention, emission of blue color, green color, red color, and/or white color can be also obtained by combining a hole injection layer, a hole transport layer, and/or an emission layer in which another material is used for an electron transport material of the present invention.

An emission material or a dopant in an emission layer which can be used for an organic EL device of the present invention is an emission material such as a daylight fluorescent material, a fluorescent whitening agent, a laser coloring matter, an organic scintillator, and various kinds of fluorescence analysis reagents described in "Optical Functional Materials" Polymer Functional Material Series (1991), p. 236, edited by the Society of Polymer Science, Japan, and published by Kyoritsu Shuppan Co., Ltd., a dopant material described in p. 155 to 156, and an emission material of a phosphor, phosphorescent material described in p. 170 to 172 of "Organic EL Materials and Displays" (2001), edited by J. Kido, and published by CMC Co., Ltd.

A compound which can be used as an emission material or a dopant in an emission layer is a polycyclic aromatic compound, a hetero aromatic compound, an organic metal complex, a coloring matter, a polymeric emission material, a styryl derivative, an aromatic amine derivative, a coumarin derivative, a borane derivative, an oxazine derivative, a compound having a spiro ring, an oxadiazole derivative, and/or a fluorene derivative. An example of the polycyclic aromatic compound is anthracene derivative, phenanthrene derivative, naphthacene derivative, pyrene derivative, chrysene derivative, perylene derivative, coronene derivative, or rubrene derivative. An example of the hetero aromatic compound is oxadiazole derivative having a dialkylamino group or a diarylamino group, pyrazoloquinoline derivative, pyridine derivative, pyran derivative, phenanthroline derivative, silole derivative, thiophene derivative having a triphenylamino group, or quinacridone derivative. An example of the organic metal complex is a complex of zinc, aluminum, beryllium, europium, terbium, dysprosium, iridium, platinum, osmium, and gold with quinolinol derivative, benzoxazole derivative, benzothiazole derivative, oxadiazole derivative, thiadiazole derivative, benzimidazole derivative, pyrrole derivative, pyridine derivative, and phenanthroline derivative. A coloring matter may be exemplified by xanthene derivative, polymethine derivative, porphyrin derivative, coumarin derivative, dicyanomethylenepyran derivative, dicyanomethylenethiopyran derivative, oxobenzanthracene derivative, carbostyryl derivative, perylene derivative, benzoxazole derivative, benzothiazole derivative, and benzimidazole derivative. An example of the polymeric emission material is polyparaphenylvinylene derivative, polythiophene derivative, polyvinylcarbazole derivative, polysilane derivative, polyfluorene derivative, and polyparaphenylene derivative. An example of the styryl derivative is amine-containing styryl derivative and styrylarylene derivative.

Another electron transport material used for an organic EL device of the present invention can be optionally selected from compounds which can be used as an electron transport compound in a photoconductive material, or compounds which can be used for an electron transport layer and an electron injection layer of the organic EL device.

A specific example of the above electron transport material is quinolinol base metal complex, 2,2'-bipyridyl derivative, phenanthroline derivative, diphenylquinone derivative, perylene derivative, oxadiazole derivative, thiophene derivative, triazole derivative, thiadiazole derivative, metal complex of oxine derivative, quinoxaline derivative, polymer of quinoxaline derivative, benzazole derivative compound, gallium complex, pyrazol derivative, perfluorated phenylene derivative, triazine derivative, pyrazine derivative, benzoquinoline derivative, imidazopyridine derivative, and borane derivative.

For a hole injection material and a hole transport material used for an organic EL device of the present invention, an optional material can be used by selecting from compounds conventionally used as a charge transport material for a hole in a photoconductive material, and publicly known materials used for a hole injection layer and a hole transport layer of the organic EL device. A specific example thereof is carbazole derivative, triarylamine derivative, and phthalocyanine derivative.

Each layer constituting an organic EL device of the present invention can be formed by making a thin film from a material constituting each layer by a vapor deposition method, a spin cast method, or a cast method. Thickness of the thus formed each layer can be set up suitably according to properties of the material without any particular limitation. The thickness is usually in a range of 2 nm to 5000 nm. As a method for forming a thin film from an emission material, the vapor deposition method is preferably adopted because a uniform film can be easily obtained and a pinhole is difficult to generate. When the thin film is formed by using the vapor deposition method, deposition conditions thereof change depending on kinds of emission materials of the present invention. In general, the deposition conditions are preferably set up suitably in a range of 50 to 400° C. as a boat heating temperature, $10^{-6}$ to $10^{-3}$ Pa as a degree of vacuum, 0.01 to 50 nm/second as a deposit rate, −150 to +300° C. as a substrate temperature, and 5 nm to 5 μm as thickness.

An organic EL device of the present invention is preferably supported on a substrate in any of the structures described above. The substrate may be any one as long as the substrate has mechanical strength, heat stability, and transparency, and a glass and a transparent plastic film can be used. A metal, an alloy, an electroconductive compound, and a mixture thereof each having a work function larger than 4 eV can be used for an anode material. A specific example thereof is a metal such as gold, CuI, indium tin oxide (hereafter abbreviated as ITO), $SnO_2$, or ZnO.

A metal, an alloy, an electroconductive compound, or a mixture thereof each having a work function smaller than 4 eV can be used for a cathode material. A specific example thereof is aluminum, calcium, magnesium, lithium, magnesium alloy, or aluminum alloy. A specific example of the alloy is aluminum/lithium fluoride, aluminum/lithium, magnesium/silver, or magnesium/indium. At least one of electrodes has preferably a light transmittance set to 10% or more in order to efficiently take out emission from an organic EL device. The electrode is preferably controlled to have a sheet resistance of several hundreds of Ω/square or less. Thickness is set depending on properties of an electrode material in a range of, usually, 10 nm to 1 μm, preferably, 10 nm to 400 nm. Such the electrode can be produced by forming a thin film using the electrode substance described above by a vapor deposition or sputtering method.

Next, as one example of a method for preparing an organic EL device by using an emission material of the present invention, a method for preparing an organic EL device comprising the anode/hole injection layer/hole transport layer/emission layer/electron transport material of the present invention/cathode each described above is explained. A thin film of an anode material is formed on a suitable substrate by a vapor deposition method to prepare an anode, and then thin films of a hole injection layer and a hole transport layer are formed on the above anode. A thin film of the emission layer is formed thereon. A thin film is formed on the above emission layer by depositing the electron transport material of the present invention, and the thin film is used as the electron transport layer. Furthermore, a thin film comprising a cathode material by a vapor deposition method is formed to prepare the cathode, and thus an intended organic EL device is obtained. In preparing the organic EL device described above, the organic EL device can be also prepared in the order of the cathode, the electron transport layer, the emission layer, the hole transport layer, the hole injection layer, and the anode by reversing a preparation order.

When direct current voltage is applied to the thus obtained organic EL device, the voltage may be applied by setting polarity of an anode as plus and a cathode as minus. When a degree of 2 to 40 V is applied, emission can be observed from a transparent or translucent electrode side (anode or cathode, and both). Moreover, the organic EL device emits also when alternating current voltage is applied. A waveform of alternating current to be applied may be optional.

In the following, the present invention is explained in more detail based on Example.

Example 1

Synthetic Example 1

Synthesis of Compound of Formula (2-2-1)

Synthesis of 9,10-bis(4,4,5,5-tetramethyl-1,3,2-dioxaborolanyl)anthracene

Into a flask, 5.38 g of 9,10-dibromoanthracene, 10 g of bis(pinacolate)diboron, 784 mg of [1,1'-bis(diphenylphosphino)ferrocene]palladium(II) dichloride, 9.4 g of potassium acetate, and 100 ml of dimethylsulfoxide were put, and the solution was stirred at 100° C. for 16 hours under argon atmosphere. After heating, the reaction liquid was concentrated in an evaporator, and the concentrates were purified by silica gel column chromatography, and thus 4.38 g of 9,10-bis(4,4,5,5-tetramethyl-1,3,2-dioxaborolanyl)anthracene was obtained.

Synthesis of 5-bromo-2,3'-bipyridine

Into a 1 l flask, 20 g of 3-pyridine boronic acid, 50 g of 2,5-dibromopyridine, 5.5 g of $Pd(PPh_3)_4$, 33.9 g of sodium carbonate, 500 ml of toluene, 150 ml of ethanol, and 150 ml of pure water were put, and the solution was stirred at reflux temperature for 3.5 hours. After heating, the reaction liquid was cooled to room temperature and the organic layer was extracted. The organic layer was concentrated in an evaporator, the concentrates were purified by column chromatography, then, recrystallized in heptane, and thus 27 g of 5-bromo-2,3'-bipyridine was obtained.

Synthesis of 9,10-bis(2,3'-bipyridine-5-yl)anthracene

Into a flask, 2.53 g of 9,10-bis(4,4,5,5-tetramethyl-1,3,2-dioxaborolanyl)anthracene, 2 g of 5-bromo-2,31-bipyridine, 960 mg of $Pd(PPh_3)_4$, 3.81 g of tripotassium phosphate, 60 ml of dioxane, and 15 ml of pure water were put, and the solution was stirred at reflux temperature for 3 days under argon atmosphere. After heating, the reaction liquid was cooled to room temperature, pure water was added, and then the organic layer was extracted. The organic layer was concentrated in an evaporator, the concentrates were purified by column chromatography, yellow powders which were concentrated again and obtained were washed by toluene, and thus 800 mg of 9,10-bis(2,3'-bipyridine-5-yl)anthracene was obtained.

1H-NMR ($CDCl_3$) δ 7.4-7.6 (m, 6H), 7.2-7.3 (m, 4H), 8.0 (d, 4H), 8.5 (s, 2H), 8.8 (d, 4H), 9.4 (s, 2H).

Example 2

Synthetic Example 2

Synthesis of Compound of Formula (2-2-2)

Synthesis of 2-phenylanthracene

Into a flask, 5.00 g of 2-chloroanthracene, 4.3 g of phenylboronic acid, 538 mg of tris(dibenzylieneacetone)dipalladium(0), 494 mg of tricyclohexyl phosphine, 9.98 g of tripotassium phosphate, and 75 ml of toluene were put, and the solution was stirred at reflux temperature for 2 hours under argon atmosphere. After heating, 1.5 liter of toluene was added to the reaction liquid, the liquid was cooled to room temperature and then filtrated, and thus the filtrates were purified by silica gel column chromatography. The filtrates were concentrated in an evaporator, the concentrates were recrystallized in toluene, and thus 5.0 g of 2-phenylanthracene was obtained.

Synthesis of 9,10-dibromo-2-phenylanthracene

In a flask under nitrogen atmosphere, 3.32 g of 2-phenylanthracene was dissolved in 400 ml of dichloromethane. In the flask, a solution in which 5.00 g of bromine was dissolved in 30 ml of carbon tetrachloride was dropped over 15 minutes. After dropping, the solution was stirred at room temperature for 2 hours, and the reaction was terminated using a sodium thiosulfate aqueous solution. The organic layer was extracted by a separating funnel, and concentrated in an evaporator. The concentrates were recrystallized in 50 ml of toluene, and thus 4.4 g of 9,10-dibromo-2-phenylanthracene was obtained.

Synthesis of 9,10-bis(4,4,5,5-tetramethyl-1,3,2-dioxaborolanyl)-2-phenylanthracene Into a flask, 10.0 g of 9,10-dibromo-2-phenylanthracene, 14.8 g of bis(pinacolate)diboron, 838 mg of bis(dibenzylieneacetone)palladium(0), 1.02 g of tricyclohexyl phosphine, 7.15 g of potassium acetate, and 50 ml of 1,4-dioxane were put, and the solution was stirred at reflux temperature for 8 hours under argon atmosphere. After heating, toluene was added to the reaction liquid, the reaction liquid was cooled to room temperature and then filtrated, and thus the filtrates were concentrated in an evaporator. The concentrates were purified by silica gel column chromatography, and then recrystallized in a tetrahydrofuran/heptane mixed solution, and thus 8.3 g of 9,10-bis(4,4,5,5-tetramethyl-1,3,2-dioxaborolanyl)-2-phenylanthracene was obtained.

Synthesis of 6-bromo-2,3'-bipyridine

Under nitrogen atmosphere, 6.32 g of 3-bromopyridine was dissolved in 400 ml of dehydrated toluene. The solution was cooled at −78° C. and 17 ml of 2.6M normal-butyllithium was dropped. After 0.5 hours, 12.6 g of zinc chloride tetramethylethylenediamine, and 200 ml of dehydrated THF were added. The solution was heated to room temperature, 10.63 g of 2,6-dibromopyridine and 0.6 g of Pd(PPh$_3$)$_4$ were added, and the solution was stirred for 24 hours. The reaction liquid was washed by an ammonium chloride aqueous solution, and the organic layer was concentrated in an evaporator. The concentrates were purified by column chromatography, and thus 4.2 g of 6-bromo-2,3'-bipyridine was obtained.

Synthesis of 9,10-bis(2,3'-bipyridine-5-yl)-2-phenylanthracene

Into a flask, 2.00 g of 9,10-bis(4,4,5,5-tetramethyl-1,3,2-dioxaborolanyl)-2-phenylanthracene, 2.04 g of 5-bromo-2,3'-bipyridine, 181 mg of tris(dibenzylieneacetone)dipalladium(0), 167 mg of tricyclohexyl phosphine, 3.35 g of tripotassium phosphate, and 75 ml of toluene were put, and the solution was stirred at reflux temperature for 24 hours under argon atmosphere. After heating, the reaction liquid was cooled to room temperature, and filtered by cerite. The filtrates were concentrated in an evaporator, and the concentrates were purified by silica gel column chromatography, yellow powders which were concentrated again and obtained were washed by toluene, and thus 800 mg of 9,10-bis(2,3'-bipyridine-5-yl)-2-phenylanthracene was obtained.

1H-NMR (CDCl$_3$) δ 7.2-8.2 (m, 18H), 8.5 (m, 2H), 8.7 (s, 2H), 8.9 (s, 2H), 9.4 (s, 2H)

Example 3

Synthetic Example 3

Synthesis of Compound of Formula (2-1-40)

Synthesis of 9,10-bis(2,3'-bipyridine-6-yl)-2-phenylanthracene

Into a flask, 1.5 g of 9,10-bis(4,4,5,5-tetramethyl-1,3,2-dioxaborolanyl)-2-phenylanthracene, 1.9 g of 6-bromo-2,3'-bipyridine, 201 mg of tris(dibenzylieneacetone)dipalladium(0), 187 mg of tricyclohexyl phosphine, 4.7 g of tripotassium phosphate, and 50 ml of toluene were put, and the solution was stirred at reflux temperature for 9 hours under argon atmosphere. After heating, the reaction liquid was cooled to room temperature, and washed by a saturated sodium chloride aqueous solution. The organic layer was concentrated in an evaporator, and the concentrates were purified by activated alumina column chromatography, and further recrystallized in ethyl acetate and toluene, and thus 670 mg of 9,10-bis(2,3'-bipyridine-6-yl)-2-phenylanthracene was obtained.

1H-NMR (CDCl$_3$) δ 7.3-7.4 (m, 7H), 7.5-7.7 (m, 7H), 7.8 (m, 1H), 7.9 (s, 1H), 8.0 (m, 2H), 8.1 (m, 2H), 8.4 (m, 2H), 8.6 (m, 2H), 9.3 (s, 2H)

Example 4

Synthetic Example 4

Synthesis of Compound of Formula (2-2-9)

Synthesis of 3,6-dibromo-9-naphthalene-1-yl-carbazole

Into a flask, 10.00 g of 3,6-dibromo-9H-carbazole, 4.1 ml of 1-fluoronaphthalene, 12.06 g of cesium carbonate, and 300 ml of dimethylsulfoxide were put, and the solution was stirred at 145° C. for 36 hours under nitrogen atmosphere. After heating, the reaction liquid was cooled to room temperature and then filtrated, and the filtrates were concentrated by a vacuum pump. The concentrates were purified by silica gel column chromatography, and then washed by methanol, and thus 5.5 g of 3,6-dibromo-9-naphthalene-1-yl-carbazole was obtained.

Synthesis of 3,6-bis(4,4,5,5-tetramethyl-1,3,2-dioxaborolanyl)-9-naphthalene-1-yl-carbazole Into a flask, 2.00 g of 3,6-dibromo-9-naphthalene-1-yl-carbazole, 2.46 g of bis(pinacolate)diboron, 304 mg of bis(dibenzylieneacetone)palladium(0), 358 mg of tricyclohexyl phosphine, 1.30 g of potassium acetate, and 30 ml of 1,4-dioxane were put, and the solution was stirred at reflux temperature for 7 hours under argon atmosphere. After heating, toluene was added to the reaction liquid, the reaction liquid was cooled to room temperature and then filtrated, and thus the filtrates were concentrated in an evaporator. The concentrates were purified by silica gel column chromatography, and thus 820 mg of 3,6-bis(4,4,5,5-tetramethyl-1,3,2-dioxaborolanyl)-9-naphthalene-1-yl-carbazole was obtained.

Synthesis of 3,6-bis(2,3'-bipyridine-5-yl)-9-naphthalene-1-yl-carbazole

Into a flask, 1.50 g of 3,6-bis(4,4,5,5-tetramethyl-1,3,2-dioxaborolanyl)-9-naphthalene-1-yl-carbazole, 1.32 g of 5-bromo-2,3'-bipyridine, 194 mg of Pd(PPh$_3$)$_4$, 2.40 g of tripotassium phosphate, 25 ml of 1,4-dioxane, and 5 ml of water were put, and the solution was stirred at reflux temperature for 10 hours under argon atmosphere. After heating, the reaction liquid was cooled to room temperature, and washed by a saturated sodium chloride aqueous solution. The organic layer was concentrated in an evaporator, and the concentrates were washed by methanol. After washing, the concentrates were purified by silica gel column chromatography, recrystallized in a chloroform/ethyl acetate mixed solvent, and thus 475 mg of 3,6-bis(2,3'-bipyridine-5-yl)-9-naphthalene-1-yl-carbazole was obtained.

1H-NMR (CDCl$_3$) δ 7.1 (d, 2H), 7.3-7.5 (m, 4H), 7.6 (t, 1H), 7.6-7.8 (m, 4H), 7.9 (d, 2H), 8.0-8.2 (m, 4H), 8.4 (d, 2H), 8.5 (s, 2H), 8.6 (d, 2H), 9.1 (s, 2H) 9.3 (s, 2H)

Example 5

Synthetic Example 5

Synthesis of Compound of Formula (2-2-29)

Synthesis of 5,9-bis(4,4,5,5-tetramethyl-1,3,2-dioxaborolanyl)-7,7-diphenylbenzo[c]fluorine Into a flask, 13.1 g of 5,9-bis(trifluoromethanesulfonyloxy)-7,7-diphenylbenzo[c]fluorene, 11.2 g of bis(pinacolate)diboron, 1.2 g of bis(dibenzylieneacetone)palladium(0), 1.4 g of tricyclohexyl phosphine, 6.5 g of potassium acetate, and 300 ml of 1,4-dioxane were put, and the solution was stirred at 80° C. for 4.5 hours under argon atmosphere. After heating, the reaction liquid was concentrated in an evaporator. The concentrates were purified by silica gel column chromatography, and then washed by ethanol, and thus 9.8 g of 5,9-bis(4,4,5,5-tetramethyl-1,3,2-dioxaborolanyl)-7,7-diphenylbenzo[c]fluorene was obtained.

Synthesis of 5,9-bis(2,3'-bipyridine-5-yl)-7,7-diphenylbenzo[c]fluorine

Into a flask, 2.0 g of 5,9-bis(4,4,5,5-tetramethyl-1,3,2-dioxaborolanyl)-7,7-diphenylbenzo[c]fluorene, 1.65 g of 5-bromo-2,3'-bipyridine, 222 mg of Pd(PPh$_3$)$_4$, 2.72 g of tripotassium phosphate, 25 ml of 1,4-dioxane, and 5 ml of water were put, and the solution was stirred at reflux temperature for 7.5 hours under argon atmosphere. After heating, the reaction liquid was cooled to room temperature, and washed by a saturated sodium chloride aqueous solution. The organic layer was concentrated in an evaporator, and the concentrates were purified by silica gel column chromatography. The concentrates were recrystallized in a chloroform/ethyl acetate mixed solvent, and thus 345 mg of 5,9-bis(2,3'-bipyridine-5-yl)-7,7-diphenylbenzo[c]fluorene was obtained.

1H-NMR (CDCl$_3$) δ 7.3 (m, 10H), 7.4 (m, 2H), 7.5 (m, 2H), 7.7-8.0 (m, 8H), 7.9 (m, 2H), 8.5 (d, 1H), 8.6 (m, 2H), 8.8 (s, 1H), 8.9 (d, 1H), 9.0 (s, 1H), 9.3 (s, 1H), 9.4 (s, 1H)

Example 6

Synthetic Example 6

Synthesis of Compound of Formula (2-2-25)

Synthesis of 2,7-bis(2,3'-bipyridine-5-yl)-9,9-dihexylfluorene

Into a flask, 0.6 g of 9,9-dihexyl-fluorene-2,7-diboronic acid, 0.5 g of 5-bromo-2,3'-bipyridine, 115 mg of Pd(PPh$_3$)$_4$, 1.27 g of tripotassium phosphate, and 20 ml of toluene were put, and the solution was stirred at reflux temperature for 6.5 hours under argon atmosphere. After heating, the reaction liquid was cooled to room temperature, and washed by a saturated sodium chloride aqueous solution. The organic layer was concentrated in an evaporator, and the concentrates were purified by activated alumina column chromatography. The concentrates were recrystallized in a heptane/ethyl acetate mixed solvent, and thus 150 mg of 2,7-bis(2,3'-bipyridine-5-yl)-9,9-dihexylfluorene was obtained.

1H-NMR (CDCl$_3$) δ 0.7 (m, 10H), 1.1 (m, 12H), 2.0 (m, 4H), 7.4 (m, 2H), 7.6 (m, 4H), 7.8 (m, 4H), 8.0 (m, 2H), 8.4 (m, 2H), 8.6 (m, 2H), 9.0 (s, 2H), 9.2 (s, 2H)

Example 7

Synthetic Example 7

Synthesis of Compound of Formula (2-2-30)

Synthesis of 1,4-bis(2,3'-bipyridine-5-yl)-naphthalene

Into a flask, 2.2 g of 1,4-bis(4,4,5,5-tetramethyl-1,3,2-dioxaborolanyl)-naphthalene, 2.8 g of 5-bromo-2,3'-bipyridine, 450 mg of tris(dibenzylieneacetone)dipalladium(0), 280 mg of tricyclohexyl phosphine 9.6 g of tripotassium phosphate, and 50 ml of toluene were put, and the solution was stirred at reflux temperature for 16 hours under argon atmosphere. After heating, the reaction liquid was cooled to room temperature, and washed by a saturated sodium chloride aqueous solution. The organic layer was concentrated in an evaporator, and the concentrates were purified by activated alumina column chromatography. The concentrates were further washed by ethyl acetate, and then recrystallized in toluene, and thus 250 mg of 1,4-bis(2,3'-bipyridine-5-yl)-naphthalene was obtained.

1H-NMR (CDCl$_3$) δ 7.4-7.6 (m, 6H), 7.9-8.1 (m, 6H), 8.4 (m, 2H), 8.7 (m, 2H), 8.9 (s, 2H), 9.3 (s, 2H)

Example 8

Synthetic Example 8

Synthesis of Compound of Formula (2-1-1)

Synthesis of 9,10-bis(2,3'-bipyridine-6-yl)-anthracene

Into a flask, 1.56 g of 9,10-bis(4,4,5,5-tetramethyl-1,3,2-dioxaborolanyl)anthracene, 1.86 g of 6-bromo-2,3'-bipyridine, 198 mg of tris(dibenzylieneacetone)dipalladium(0), 182 mg of tricyclohexyl phosphine, 4.6 g of tripotassium phosphate, and 60 ml of toluene were put, and the solution was stirred at reflux temperature for 12 hours under argon atmosphere. After heating, the reaction liquid was cooled to room temperature, and washed by water. The organic layer was concentrated in an evaporator, and the concentrates were purified by activated alumina column chromatography, and thus 960 mg of 9,10-bis(2,3'-bipyridine-6-yl)anthracene was obtained.

1H-NMR (CDCl$_3$) δ 7.2-7.8 (m, 12H), 7.9-8.1 (m, 4H), 8.4 (s, 2H), 8.6 (s, 2H), 9.3 (s, 2H)

Example 9

Synthetic Example 9

Synthesis of Compound of Formula (2-1-41)

Synthesis of 3,9-bis(4,4,5,5-tetramethyl-1,3,2-dioxaborolanyl)-11,11-diphenylbenzo[α]fluorine Into a flask, 5.2 g of 3,9-bis(trifluoromethanesulfonyloxy)-11,11-diphenylbenzo[α]fluorene, 4.6 g of bis(pinacolate)diboron, 0.48 g of bis(dibenzylieneacetone)palladium(0), 0.56 g of tricyclohexyl phosphine, 2.6 g of potassium acetate, and 100 ml of 1,4-dioxane were put, and the solution was stirred at 80° C. for 3.5 hours under argon atmosphere. After heating, the reaction liquid was cooled to room temperature, and ethyl acetate was added, and then the reaction liquid was filtrated. Obtained solid was purified by silica gel column chromatography, and thus 2.0 g of 3,9-bis(4,4,5,5-tetramethyl-1,3,2-dioxaborolanyl)-11,11-diphenylbenzo[α]fluorene was obtained.

Synthesis of 3,9-bis(2,3'-bipyridine-6-yl)-11,11-diphenylbenzo[α]fluorine

Into a flask, 1.8 g of 3,9-bis(4,4,5,5-tetramethyl-1,3,2-dioxaborolanyl)-11,11-diphenylbenzo[α]fluorene, 1.60 g of 6-bromo-2,3'-bipyridine, 215 mg of Pd(PPh$_3$)$_4$, 2.63 g of tripotassium phosphate, 25 ml of 1,4-dioxane, and 5 ml of water were put, and the solution was stirred at reflux temperature for 4.5 hours under argon atmosphere. After heating, the reaction liquid was cooled to room temperature, and washed by water. Then, the reaction liquid was washed by methanol, and then purified by activated alumina column chromatography, furthermore, recrystallized in N,N-dimethylformamide and chlorobenzene, and thus 142 mg of 3,9-bis(2,3'-bipyridine-6-yl)-11,11-diphenylbenzo[α]fluorene was obtained.

1H-NMR (CDCl$_3$) δ 7.3-7.4 (m, 6H), 7.4 (m, 6H), 7.55 (d, 1H), 7.65 (d, 1H), 7.7 (s, 1H), 7.8 (d, 1H), 7.85 (d, 1H) 7.9 (d, 1H), 7.95 (d, 1H) 8.0 (d, 1H), 8.0-8.1 (m, 3H), 8.2 (s, 1H), 8.3-8.4 (m, 2H), 8.6-8.7 (m, 2H), 8.9 (s, 1H), 9.0 (s, 1H), 9.2 (s, 1H), 9.25 (s, 1H)

Example 10

Synthetic Example 10

Synthesis of Compound of Formula (2-1-42)

Synthesis of 2,7-bis(4,4,5,5-tetramethyl-1,3,2-dioxaborolanyl)triphenylene

Into a flask, 2 g of 1,2-bis(3-methoxyphenyl)benzene was put, and allowed to dissolve in 100 ml of dichloromethane under nitrogen atmosphere. In the solution, 3.25 g of iron(III) chloride was added, and the solution was stirred at room temperature for 56.5 hours. Methanol was added to terminate the reaction, and then the solution was washed by water. The organic layer was purified by silica gel column chromatography, and then recrystallized in a toluene/heptane mixed solvent, and thus 1.4 g of 2,7-dimethoxytriphenylene was obtained. Obtained 2,7-dimethoxytriphenylene was converted to 2,7-dihydroxytriphenylene by boron tribromide, and allowed to react with trifluoromethanesulfonyl chloride, and converted to 2,7-bis(trifluoromethanesulfonyloxy)triphenylene. The product was allowed react with bis(pinacolate)diboron, and thus 2,7-bis(4,4,5,5-tetramethyl-1,3,2-dioxaborolanyl)triphenylene was synthesized.

Synthesis of 2,7-bis(2,3'-bipyridine-6-yl)triphenylene

Into a flask, 0.4 g of 2,7-bis(4,4,5,5-tetramethyl-1,3,2-dioxaborolanyl)triphenylene, 0.43 g of 6-bromo-2,3'-bipyridine, 58 mg of Pd(PPh$_3$)$_4$, 353 mg of sodium carbonate, 15 ml of toluene, 5 ml of ethanol, and 5 ml of water were put, and the solution was stirred at reflux temperature for 14.5 hours under argon atmosphere. After heating, the reaction liquid was cooled to room temperature, and water was added. The solution was extracted by dichloromethane, and the organic layer was concentrated in an evaporator. The concentrates were purified by activated alumina column chromatography, recrystallized in chlorobenzene, and thus 96 mg of 2,7-bis(2,3'-bipyridine-6-yl)triphenylene was obtained.

1H-NMR (CDCl$_3$) δ 7.5 (m, 2H), 7.7-7.8 (m, 4H), 7.9-8.0 (m, 4H), 8.45 (d, 2H), 8.55 (d, 2H), 8.7 (m, 2H), 8.8-9.0 (m, 4H), 9.4-9.6 (m, 4H)

Another emission material of the present invention can be synthesized through selecting a raw material compound suitably by a method corresponding to the synthetic example described above.

Example 11

A 25 mm×75 mm×1.1 mm glass substrate (manufactured by Tokyo Sanyo Vacuum Co., Ltd.) on which ITO was deposited at a thickness of 150 nm was used as a transparent substrate. The transparent substrate was fixed to a substrate holder of a commercial deposition system (manufactured by Sinku Kiko Co., Ltd.), and a molybdenum-made boat source for deposition containing copper phthalocyanine, a molybdenum-made boat source for deposition containing N,N'-diphenyl-N,N'-dinaphthyl-4,41-diaminobiphenyl (hereinafter abbreviated as NPD), a molybdenum-made boat source for deposition containing tris(8-hydroxyquinoline)aluminum (hereinafter abbreviated as ALQ), a molybdenum-made boat source for deposition containing the compound (2-2-1) synthesized in Example 1, a molybdenum-made boat source for deposition containing lithium fluoride, and a tungsten-made boat source for deposition containing aluminum were mounted. A vacuum chamber was decompressed to 1×10$^{-3}$ Pa, the boat source for deposition containing copper phthalocyanine was heated, and copper phthalocyanine was deposited to become a thickness of 20 nm to form a hole injection layer, next, the boat source for deposition containing NPD was heated, and NPD was deposited to become a thickness of 30 nm to form a hole transport layer. Next, the molybdenum-made boat source for deposition containing ALQ was heated, and ALQ was deposited to become a thickness of 35 nm to form an emission layer. Next, the boat source for deposition containing the compound (2-2-1) was heated, and the compound (2-2-1) was deposited to become a thickness of 15 nm to form an electron transport layer. The above deposit rate was 0.1 to 0.2 nm/second. Then, the boat source for deposition containing lithium fluoride was heated, and lithium fluoride was deposited to become a thickness of 0.5 nm at a deposit rate of 0.003-0.01 nm/second, then, the boat source for deposition containing aluminum was heated, and aluminum was deposited to become a thickness of 100 nm at a deposit rate of 0.2 to 0.5 nm/second, and thus an organic EL device was obtained. When direct current voltage was applied by using an ITO electrode as an anode, and a lithium fluoride/aluminum electrode as a cathode, emission of green color having a wavelength of approximately 520 nm was obtained. Moreover, when a constant current drive test was carried out at current density for obtaining an initial luminance of 1000 cd/m$^2$, luminance after elapse of approximately 60 hours was 906 cd/m$^2$.

When a direct current voltage of approximately 6 V was applied, an electric current of approximately 149 mA/cm$^2$ flowed, and thus emission of green color having a luminance of approximately 4300 cd/m$^2$, and a wavelength of 520 nm was obtained.

Example 12

A 25 mm×75 mm×1.1 mm glass substrate (manufactured by Tokyo Sanyo Vacuum Co., Ltd.) on which ITO was deposited at a thickness of 150 nm was used as a transparent substrate. The transparent substrate was fixed to a substrate holder of a commercial deposition system (manufactured by Sinku Kiko Co., Ltd.), and a molybdenum-made boat source for deposition containing copper phthalocyanine, a molybdenum-made boat source for deposition containing N,N'-diphenyl-N,N'-dinaphthyl-4,4'-diaminobiphenyl (hereinafter abbreviated as NPD), a molybdenum-made boat source for deposition containing the following compound (A): 9-phenyl-10-[6-(1,1';3,1")terphenyl-5'-yl]naphthalene-2-yl]anthracene, a molybdenum-made boat source for deposition containing the following styrylamine derivative (B): N,N,N',N'-tetra(4-biphenylyl)-4,4'-diaminostilbene, a molybdenum-made boat source for deposition containing the compound (2-2-1), a molybdenum-made boat source for deposition containing lithium fluoride, and a tungsten-made boat source for deposition containing aluminum were mounted.

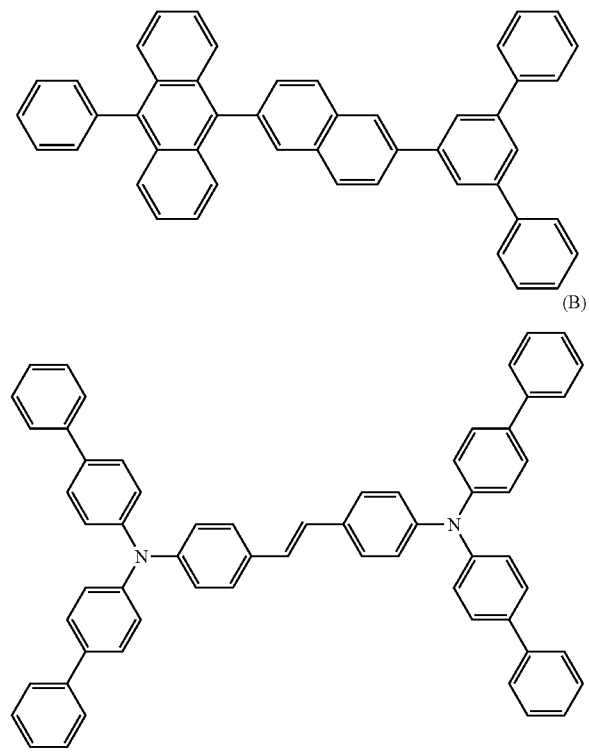

A vacuum chamber was decompressed to 1×10$^{-3}$ Pa, the boat source for deposition containing copper phthalocyanine was heated, and copper phthalocyanine was deposited to become a thickness of 20 nm to form a hole injection layer, next, the boat source for deposition containing NPD was heated, and NPD was deposited to become a thickness of 30 nm to form a hole transport layer. Next, the molybdenum-made boat source for deposition containing the compound (A) and the molybdenum-made boat source for deposition containing the compound (B) were simultaneously heated, and the compounds (A) and (B) were deposited to become a thickness of 30 nm to form an emission layer. A deposit rate was adjusted such that a weight ratio of the compound (A) and the compound (B) may become approximately 95 to 5. Next, the boat source for deposition containing the compound (2-2-1) was heated, and the compound (2-2-1) was deposited to become a thickness of 20 nm to form an electron transport layer. The above deposit rate was 0.001 to 3.0 nm/second. Then, the boat source for deposition containing lithium fluoride was heated, and lithium fluoride was deposited to become a thickness of 0.5 nm at a deposit rate of 0.003 to 0.01 nm/second, then, the boat source for deposition containing aluminum was heated, and aluminum was deposited to become a thickness of 100 nm at a deposit rate of 0.1 to 1.0 nm/second, and thus an organic EL device was obtained. When direct current voltage was applied by using an ITO electrode as an anode, and a lithium fluoride/aluminum electrode as a cathode, emission of blue color having a wavelength of approximately 455 nm was obtained. Moreover, a constant current drive test was carried out at current density for obtaining an initial luminance of 1000 cd/m$^2$. Drive test start voltage was 4.75 V, and luminance after elapse of 80 hours was 931 cd/m$^2$.

Example 13

An organic EL device was obtained in a manner similar to Example 12 except that a compound (2-2-2) was used instead of the compound (2-2-1). An ITO electrode was used as an anode, and a lithium fluoride/aluminum electrode as a cathode, and then a constant current drive test was carried out at current density for obtaining an initial luminance of 1000 cd/m$^2$. Drive test start voltage was 5.53 V, and luminance after elapse of 80 hours was 849 cd/m$^2$.

Example 14

An organic EL device was obtained in a manner similar to Example 12 except that a compound (2-1-40) was used instead of the compound (2-2-1). An ITO electrode was used as an anode, and a lithium fluoride/aluminum electrode as a cathode, and then a constant current drive test was carried out at current density for obtaining an initial luminance of 1000 cd/m$^2$. Drive test start voltage was 4.92 V, and luminance after elapse of 80 hours was 881 cd/m$^2$.

Example 15

An organic EL device was obtained in a manner similar to Example 12 except that a compound (2-2-9) was used instead of the compound (2-2-1). An ITO electrode was used as an anode, and a lithium fluoride/aluminum electrode as a cathode, and then a constant current drive test was carried out at current density for obtaining an initial luminance of 1000 cd/m$^2$. Drive test start voltage was 5.72 V, and luminance after elapse of 25 hours was 767 cd/m$^2$.

Example 16

An organic EL device was obtained in a manner similar to Example 12 except that a compound (2-2-29) was used instead of the compound (2-2-1). An ITO electrode was used as an anode, and a lithium fluoride/aluminum electrode as a cathode, and then a constant current drive test was carried out at current density for obtaining an initial luminance of 1000 cd/m². Drive test start voltage was 4.62 V, and luminance after elapse of 80 hours was 617 cd/m².

Example 17

An organic EL device was obtained in a manner similar to Example 12 except that a compound (2-2-25) was used instead of the compound (2-2-1). An ITO electrode was used as an anode, and a lithium fluoride/aluminum electrode as a cathode, and then a constant current drive test was carried out at current density for obtaining an initial luminance of 1000 cd/m². Drive test start voltage was 4.54 V, and luminance after elapse of 80 hours was 680 cd/m².

Example 18

An organic EL device was obtained in a manner similar to Example 12 except that a compound (2-2-30) was used instead of the compound (2-2-1). An ITO electrode was used as an anode, and a lithium fluoride/aluminum electrode as a cathode, and then a constant current drive test was carried out at current density for obtaining an initial luminance of 1000 cd/m². Drive test start voltage was 4.80 V, and luminance after elapse of 80 hours was 700 cd/m².

Example 19

An organic EL device was obtained in a manner similar to Example 12 except that a compound (2-1-1) was used instead of the compound (2-2-1). An ITO electrode was used as an anode, and a lithium fluoride/aluminum electrode as a cathode, and then a constant current drive test was carried out at current density for obtaining an initial luminance of 1000 cd/m². Drive test start voltage was 4.34 V, and luminance after elapse of 25 hours was 885 cd/m².

Comparative Example 1

An organic EL device was obtained in a manner similar to Example 11 except that the following compound (C) (the compound II-4 described in Patent document 1) was used instead of the compound (2-2-1). An ITO electrode was used as an anode, and a lithium fluoride/aluminum electrode as a cathode, and then a constant current drive test was carried out at current density for obtaining an initial luminance of 1000 cd/m², luminance after elapse of approximately 60 hours was 884 cd/m². When a direct current voltage of approximately 6 V was applied, an electric current of approximately 121 mA/cm² flowed, and emission of green color having a luminance of approximately 3920 cd/cm², and a wavelength of 520 nm was obtained.

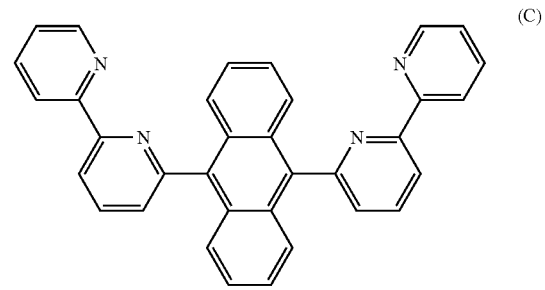

(C)

Comparative Example 2

An organic EL device was obtained in a manner similar to Example 12 except that the compound (C) was used instead of the compound (2-2-1). An ITO electrode was used as an anode, and a lithium fluoride/aluminum electrode as a cathode, and then a constant current drive test was carried out at current density for obtaining an initial luminance of 1000 cd/m². Drive test start voltage was 3.71 V, luminance after elapse of 25 hours was 699 cd/m², and luminance after elapse of 80 hours was 496 cd/m².

Comparative Example 3

An organic EL device was obtained in a manner similar to Example 12 except that tris(8-quinolinol)aluminum ($Alq_3$) was used instead of the compound (2-2-1). An ITO electrode was used as an anode, and a lithium fluoride/aluminum electrode as a cathode, and then a constant current drive test was carried out at current density for obtaining an initial luminance of 1000 cd/m². Drive test start voltage was 6.36 V, and luminance after elapse of 80 hours was 830 cd/m².

INDUSTRIAL APPLICABILITY

According to a preferable embodiment of the present invention, an organic EL device which is further better in performance of drive voltage and life of a device can be provided. In particular, drive voltage and life of a device for emission of blue color can be improved, and therefore a high performance display unit including the above improved performance can be provided.

What is claimed is:

1. A compound represented by the following Formula (2-2):

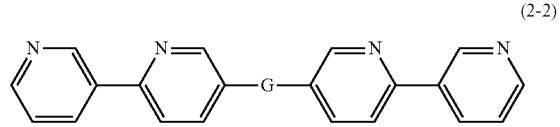

(2-2)

wherein G is a divalent group derived from one compound selected from the group consisting of compounds represented by the following Formulas (A-1) to (A-20) and Formulas (B-1) to (B-42):

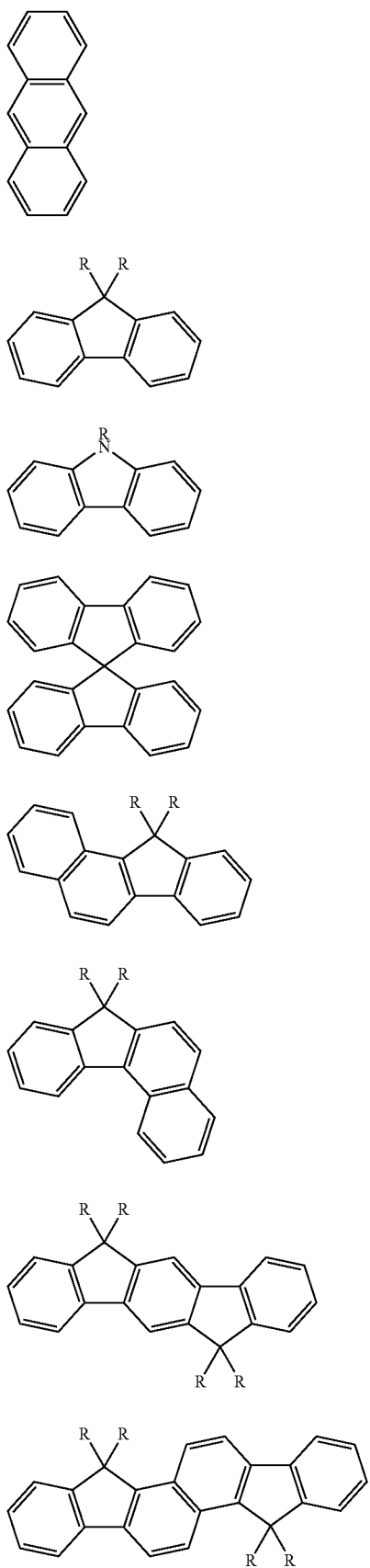
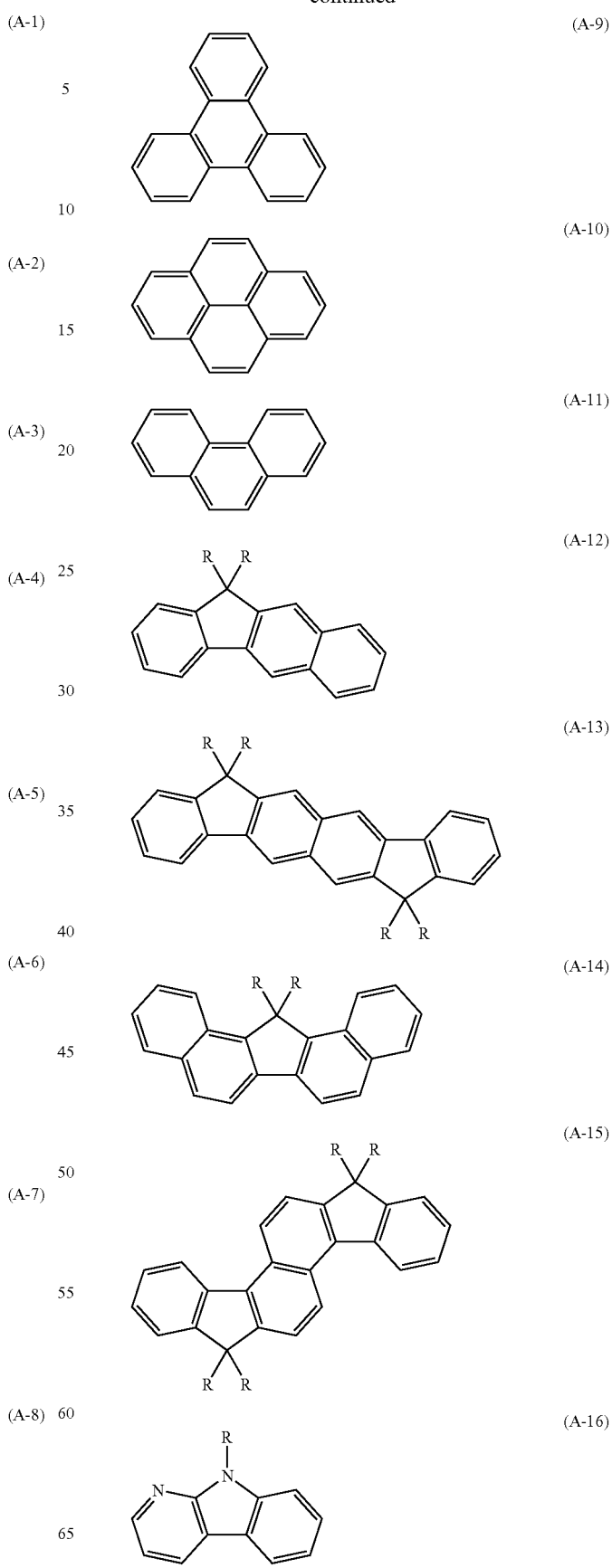

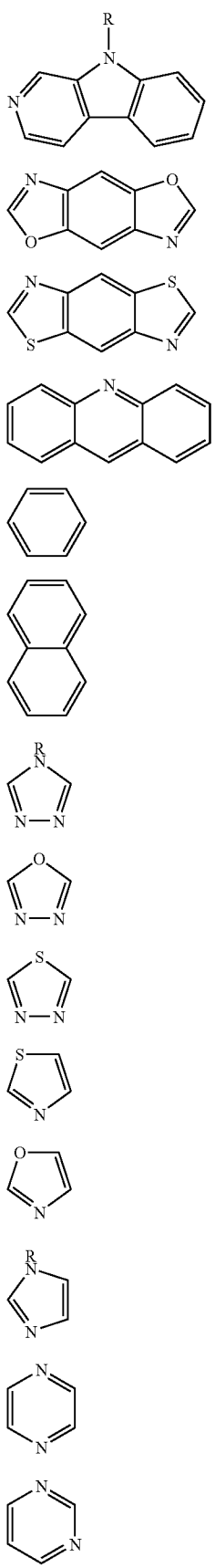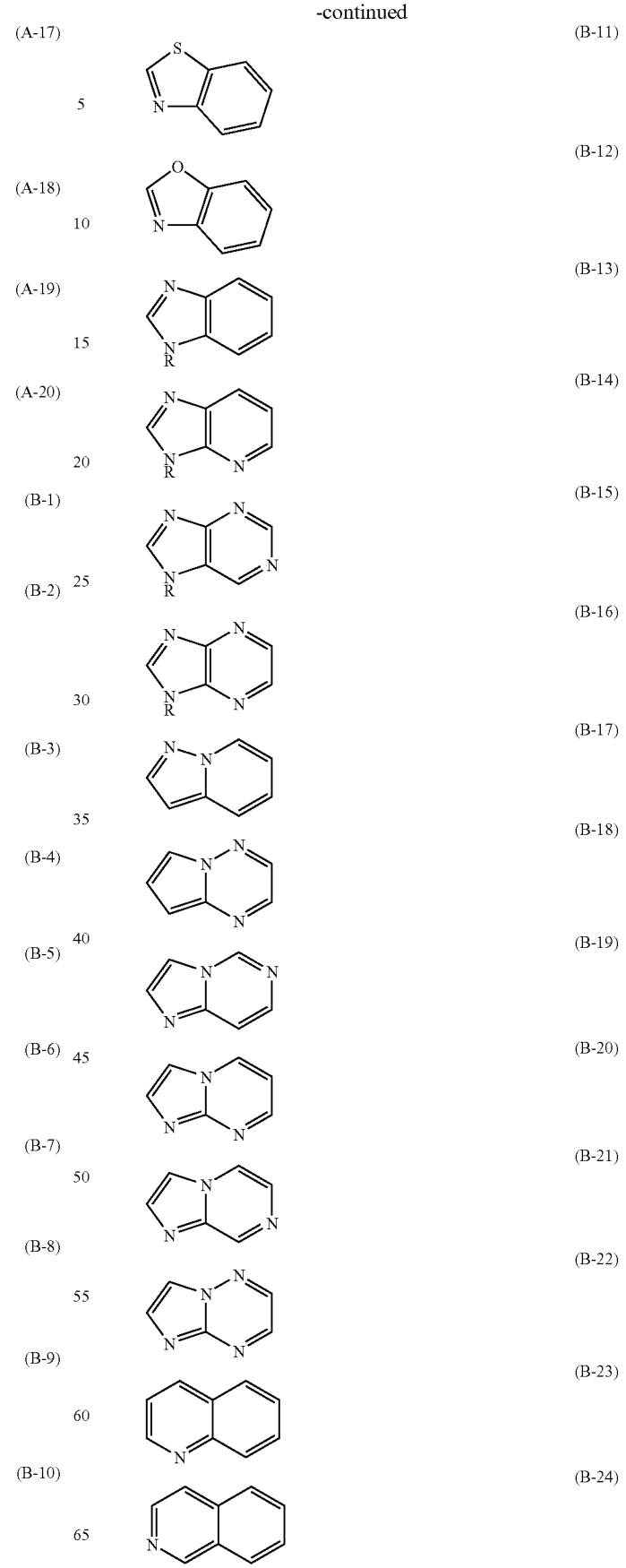

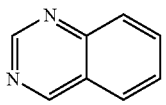
(B-25)

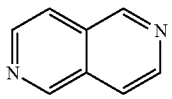
(B-26)

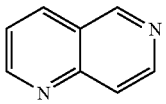
(B-27)

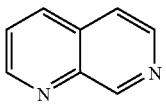
(B-28)

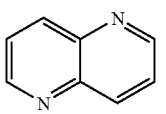
(B-29)

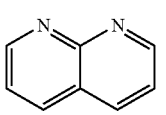
(B-30)

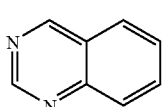
(B-31)

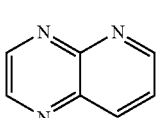
(B-32)

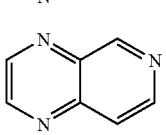
(B-33)

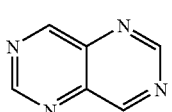
(B-34)

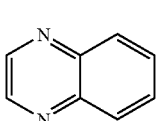
(B-35)

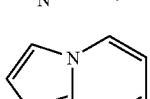
(B-36)

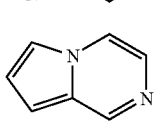
(B-37)

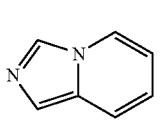
(B-38)

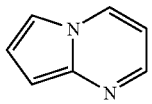
(B-39)

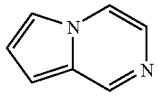
(B-40)

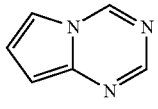
(B-41)

(B-42)

wherein each R is independently hydrogen, methyl, ethyl, hexyl, cyclohexyl, phenyl, 1-naphthyl, or 2-naphthyl; and a divalent group derived from one compound selected from the group consisting of compounds represented by Formulas (A-1) to (A-20) and Formulas (B-1) to (B-42) may have a substituent on a position other than an atom having a free valency.

2. The compound as described in claim 1, wherein G is a divalent group derived from one compound selected from the group consisting of compounds represented by the Formulas (A-1) to (A-20), and the divalent group may have a substituent.

3. The compound as described in claim 1, wherein G is a divalent group derived from one compound selected from the group consisting of compounds represented by the Formulas (A-1) to (A-10), and the divalent group may have a substituent.

4. The compound as described in claim 1, wherein G is one group selected from the group consisting of divalent groups represented by the following Formulas (C-1) to (C-15):

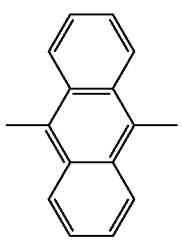
(C-1)

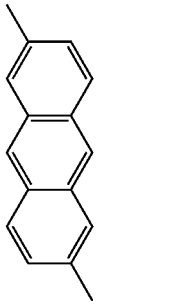
(C-2)

-continued

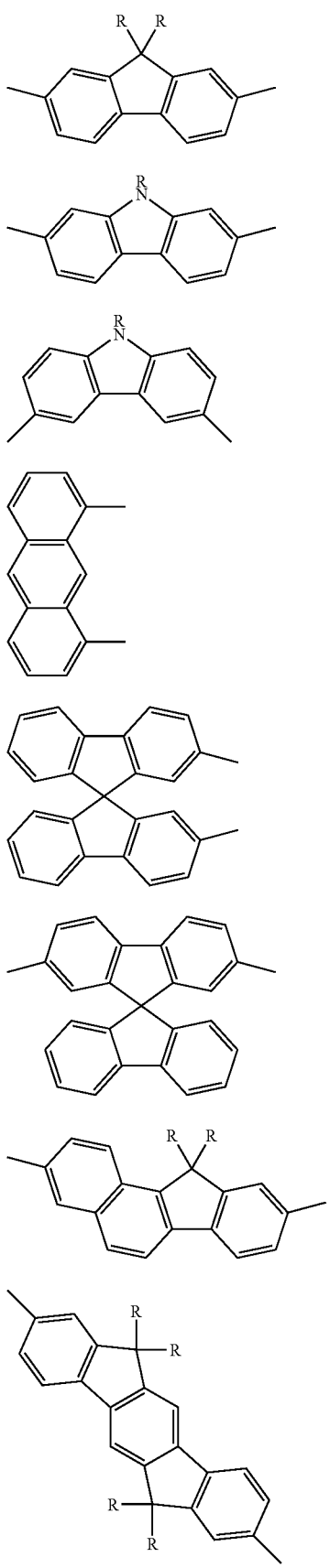

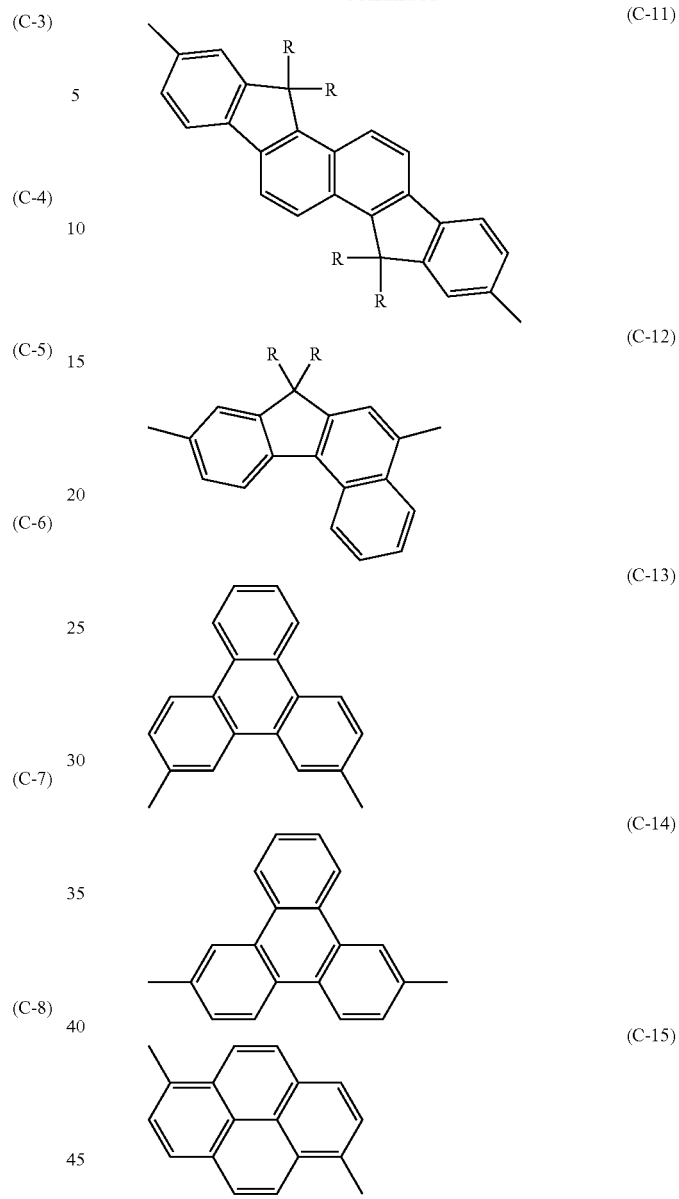

wherein each R is independently hydrogen, methyl, ethyl, hexyl, cyclohexyl, phenyl, 1-naphthyl, or 2-naphthyl; and a divalent group represented by Formulas (C-1) to (C-15) may have a substituent on a position other than an atom having a free valency.

5. The compound as described in claim 1, wherein G is 2-phenylanthracene-9,10-diyl.

6. An organic electroluminescent device comprising the compound as described in claim 1.

7. An organic electroluminescent device comprising at least a hole transport layer, an emission layer, and an electron transport layer sandwiched between an anode and a cathode on a substrate, wherein the above electron transport layer comprises the compound as described in claim 1.

8. An organic electroluminescent device comprising the compound as described in claim 2.

9. An organic electroluminescent device comprising the compound as described in claim 3.

10. An organic electroluminescent device comprising the compound as described in claim 4.

11. An organic electroluminescent device comprising the compound as described in claim 5.

12. An organic electroluminescent device comprising at least a hole transport layer, an emission layer, and an electron transport layer sandwiched between an anode and a cathode on a substrate, wherein the above electron transport layer comprises the compound as described in claim 2.

13. An organic electroluminescent device comprising at least a hole transport layer, an emission layer, and an electron transport layer sandwiched between an anode and a cathode on a substrate, wherein the above electron transport layer comprises the compound as described in claim 3.

14. An organic electroluminescent device comprising at least a hole transport layer, an emission layer, and an electron transport layer sandwiched between an anode and a cathode on a substrate, wherein the above electron transport layer comprises the compound as described in claim 4.

15. An organic electroluminescent device comprising at least a hole transport layer, an emission layer, and an electron transport layer sandwiched between an anode and a cathode on a substrate, wherein the above electron transport layer comprises the compound as described in claim 5.

* * * * *